United States Patent
Griffin et al.

(10) Patent No.: US 7,723,307 B2
(45) Date of Patent: May 25, 2010

(54) AMINO ACID DERIVATIVES AND PHARMACEUTICAL USES THEREOF

(75) Inventors: Martin Griffin, Nottingham (GB); Ian G. Coutts, Nottingham (GB); Robert E. Saint, Nottingham (GB)

(73) Assignee: Aston University, Birmingham (GB)

( * ) Notice: Subject to any disclaimer, the term of this patent is extended or adjusted under 35 U.S.C. 154(b) by 474 days.

(21) Appl. No.: 10/561,425

(22) PCT Filed: Jun. 16, 2004

(86) PCT No.: PCT/GB2004/002569

§ 371 (c)(1),
(2), (4) Date: Nov. 19, 2007

(87) PCT Pub. No.: WO2004/113363

PCT Pub. Date: Dec. 29, 2004

(65) Prior Publication Data

US 2008/0200511 A1    Aug. 21, 2008

(30) Foreign Application Priority Data

Jun. 19, 2003    (GB) ................................. 0314262.7

(51) Int. Cl.
*A61K 38/05* (2006.01)
*C07K 5/06* (2006.01)

(52) U.S. Cl. .................... 514/19; 546/226; 546/245; 548/314.7; 548/316.4; 548/531; 560/148

(58) Field of Classification Search ........................ None
See application file for complete search history.

(56) References Cited

U.S. PATENT DOCUMENTS 4,912,120 A    3/1990    Castelhano et al.
(Continued)

FOREIGN PATENT DOCUMENTS

EP    0411701    2/1991

EP    0411895    2/1991
(Continued)

OTHER PUBLICATIONS

Abo-Zenah et al., "Tissue Transglutaminase (tTg): A Role in Human Allograft Nephropathy." 2001, *J. Am. Soc. Nephrol.* 12, 4454A.
(Continued)

*Primary Examiner*—Jeffrey E Russel
(74) *Attorney, Agent, or Firm*—Morrison & Foerster LLP

(57) ABSTRACT

Novel Amino Acid Derivatives and Pharmaceutical Uses Thereof Provided are novel compounds of Formula I:

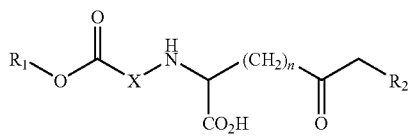

wherein 'X' represents an amino acid group, 'n' is an integer between 1 and 4, '$R_1$' represents benzyl, t-butyl or 9-fluorenylmethyl and '$R_2$' represents a tetramethylmercaptoimidazole derivative or —$S^+R_3R_4$, wherein $R_3$ and $R_4$ each independently represent lower alkyl, or a pharmaceutically and/or veterinarily acceptable derivative thereof. Further provided are pharmaceutical formulations of the compounds and the use thereof in the preparation of a medicament for inhibiting diseases in which transglutaminase has been implicated. Advantageously, the medicament is for treating fibrosis, scarring and/or cancer. Additionally provided are methods, of inhibiting autoimmune diseases such as coeliac disease, neurodegeneration and chronic inflammatory diseases (e.g. of the joints including rheumatoid arthritis and osteoarthritis in a subject) and a method for preventing or treating rejection of a transplanted organ.

39 Claims, 30 Drawing Sheets

U.S. PATENT DOCUMENTS

| | | | |
|---|---|---|---|
| 4,968,713 | A | 11/1990 | Baldwin et al. |
| 5,726,051 | A | 3/1998 | Fraij et al. |

FOREIGN PATENT DOCUMENTS

| | | |
|---|---|---|
| EP | 0771565 | 5/1997 |
| EP | 0927716 | 7/1999 |
| WO | WO 98/54093 | 12/1998 |

OTHER PUBLICATIONS

Achyuthan, K.E. & Greenberg, C.S., "Identification of a Guanosine Triphosphate-binding Site on Guinea Pig Liver Transglutaminase" 1987, *J. Biol. Chem.* 262, 1901-1906.

Achyuthan, K.E. et al., "Immunochemical analyses of human plasma fibronectin-cytosolic transglutaminase interactions" 1995, *J. Immunol. Methods* 180, 67-79.

Aeschlimann & Thomazy, "Protein Crosslinking in Assembly and Remodelling of Extracellular Matrices: The Role of Transglutaminases" 2000, *Connective Tissue Research* 41(1):1-27.

Akimov et al., "Tissue Transglutaminase Is an Integrin-binding Adhesion Coreceptor for Fibronectin" 2000, *J. Cell. Biol.* 148(4):825-838.

Amendola et al., "Tissue transglutaminase in AIDS" 2002, *J. Immunol. Methods* 265:145-159.

Antonjuk, D.J. et al., "Synthesis of Monoamides of Methotrexate from L-Glutamic Acid Monoamide t-Butyl Esters" 1984, *J. Chem. Soc. Perkin Trans.* 1 1989-2003.

Ariens et al., "Role of factor XIII in fibrin clot formation and effects of genetic polymorphisms" 2002, *Blood* 100(3):743-754.

Blas, J. et al., "Solid phase synthesis of glutamic acid derivatives via nucleophilic ring opening of N-Boc pyroglutamate with heteronucleophiles" 2000 *Tetrahedron Lett.* 41:4567-4571.

Citron et al., "Intron-Exon Swapping of Transglutaminase mRNA and Neuronal Tau Aggregation in Alzheimer's Disease" 2001 *J. Biol. Chem.* 276(5):3295-3301.

Coutts & Saint "The Reaction of Lithium Trimethylsilyldiazomethane with Pyroglutamates—a Facile Synthesis of 6-Diazo-5-oxo-norleucine and Derivatives" 1998 *Tetrahedron Lett.* 39:3243-3246.

Dubbink H.J. et al., "Human Prostate-Specific Transglutaminase: A New Prostatic Marker with a Unique Distribution Pattern" 1999 *Lab. Invest.* 79(2):141-150.

Folk & Cole, "Mechanism of Action of Guinea Pig Liver Transglutaminase" 1966, *J. Biol. Chem* 241(23):5518-5525.

Folk & Gross, "Mechanism of Action of Guinea Pig Liver Transglutaminase" 1971, *J. Biol. Chem.* 246(21):6683-6691.

Folkman J. "Angiogenesis in cancer, vascular, rheumatoid and other disease" 1995, *Nat. Med.* 1:27-31.

Freund et al., "Transglutaminase Inhibition by 2-[(2-Oxopropyl)thio]imidazolium Derivatives: Mechanism of Factor XIIIA Inactivation" 1994 *Biochemistry* 33:10109-10119.

Guadry C.A. et al., "Tissue Transglutaminase Is an Important Player at the Surface of Human Endothelial Cells: Evidence for Its Externalization and Its Colocalization with the $\beta_1$ Integrin" 1999 *Exp. Cell Res.* 252:104-113.

Gentile V. et al., "Isolation and Characterization of cDNA Clones to Mouse Macrophage and Human Endothelial Cell Tissue Transglutaminases" 1991, *J. Biol. Chem.* 266(1):478-483.

Gorman and Folk, "Structural Features of Glutamine Substrates for Transglutaminases" 1984 *J. Biol. Chem.* 259(14):9007-9010.

Greenberg C.S., et al., "Transglutaminases: multifunctional cross-linking enzymes that stabilize tissues" 1991 *FASEB J.* 5:3071-3077.

Greenberg C.S., et al., "The Transglutaminase in Vascular Cells and Tissues Could Provide an Alternate Pathway for Fibrin Stablization" 1987, *Blood* 70(3):702-709.

Griffin et al., "Transglutaminases: Nature's biological glues" 2002 *Biochem. J.*, 368:377-396.

Griffin & Wilson "Detection of ∈(y-glutamyl) lysine" 1984 *Mol. Cell. Biochem.* 58:37-49.

Gross et al., "Alkyl Isocyanates as Active Site-directed Inactivators of Guinea Pig Liver Transglutaminase" 1975 *J. Biol. Chem.* 250(19):7693-7699.

Gross & Folk "Mapping of the Active Sites of Transglutaminases" 1973 *J. Biol. Chem.* 248(18):6534-6540.

Gross & Folk "Mapping of the Active Sites of Transglutaminases" 1973 *J. Biol. Chem.* 248(4):1301-1306.

Haroon et al., "Tissue transglutaminase is expressed, active, and directly involved in rat dermal wound healing and angiogenesis" 1999 *FASEB J.* 13:1787-1795.

Hopkins et al., "Inactivation of y-Amimobutryic Acid Aminotransferase By Various Amine Buffers" 1992 *J. Enzyme Inhibition* 6:195-199.

Johnson et al. "Interleukin-1 Induces Pro-Mineralizing Activity of Cartilage Tissue Transglutaminase and Factor XIIIa" 2001 *Am. J. Pathol.* 159(1):149-163.

Johnson et al., "Transglutaminase Transcription and Antigen Translocation in Experimental Renal Scarring" 1999 *J. Am. Soc. Neph.* 10:2146-2157.

Johnson et al., "The Role of Transglutaminase in the Rat Subtotal Nephrectomy Model of Renal Fibrosis" 1997 *J. Clin. Invest.* 99(12):2950-2960.

Jones R. A., et al., "Reduced expression of tissue transglutaminase in a human endothelial cell line leads to changes in cell spreading, cell adhesion and reduced polymerisation of fibronectin" 1997 *J. Cell. Sci.* 110:2461-2472.

Kinsella, M.G. & Wight, T.N. "Formation of High Molecular Weight Dermatan Sulfate Proteoglycan in Bovine Aortic Endothelial Cell Cultures" 1990 *J. Biol. Chem.* 265(29):17891-17898.

Kuhn and Kratz "Synthesis of Imidazol-2-ylidenes by Reduction of Imidazole-2(3H)-thiones" 1993 *Synthesis* 561-562.

Lee et al., "Development of Selective Inhibitors of Transglutaminase" 1985 *J. Biol. Chem.* 260(27):14689-14694.

Lesort M. et al., "Distinct Nuclear Localization and Activity of Tissue Transglutaminase" 1998 *J. Biol. Chem.* 273(20):11991-11994.

Lorand et al, "A Filter Paper Assay for Transamidating Enzymes Using Radioactive Amine Substrates" 1972 *Anal Biochem* 50:623-631.

Lorand et al., "Amine Specificity in Transpeptidation. Inhibition of Fibrin Cross-Linking" 1968 *Biochemistry* 7:1214-1223.

Lorand et al., "Lysine As Amine Donor in Fibrin CrossLinking" 1966 *Biochem. Biophys. Res. Commun.* 25(6):629-637.

Macedo et al., "Synthesis of Dipeptide-Bound Epoxides and $\chi$, $\beta$-Unsaturated Amides as Potential Irreversible Transglutaminase Inhibitors" 2002 *Bioorganic & Medicinal Chemistry* 10:355-360.

Marrano et al., "Synthesis and Evaluation of Novel Dipeptide-Bound 1,2,4-Thiadiazoles as Irreversible Inhibitors of Guinea Pig Liver Transglutaminase" 2001 *Bioorg. Chem.* 9:3231-3241.

Martinez et al., "Transglutaminase-Mediated Processing of Fibronectin by Endothelial Cell Monolayers" 1994 *Biochemistry* 33:2538-2545.

Marzari et al., "Molecular Dissection of the Tissue Transglutaminase Autoantibody Response in Celiac Disease" 2001 *J. Immunol.* 166:4170-4176.

Mehta "High Levels of Transglutaminase Expression in Doxorubicin-Resistant Human Breast Carcinoma Cells" 1994 *Int. J. Cancer* 58:400-406.

Mehta et al., "Multidrug-Resistant MCF-7 Cells: An Identity Crisis?" 2002 *J. Natl. Caner Inst.* 94(21): 1652-1654.

Mehta et al., "Improved Efficiency and Selectivity in Peptide Synthesis: Use of Triethylsilane as a Carbocation Scavenger in Deprotection of t-Butyl Esters and t-Butoxycarbonyl-Protected sites" 1992 *Tetrahedron Lett.* 33:5441-5444.

Molberg et al., "Role of Tissue Transglutaminase in Celiac Disease" 2000 *J. Pediatr Gastroenterol Nutr.* 30:232-240.

Molina, T.M. et al., "Regioselective Ring Opening of Chiral N-Boc Protected Pyroglutamate and Pyroaminoadipate Ethyl Esters with Heteronucleophiles" 1993 *Tetrahedron* 49(18):3801-3808.

Pliura et al., "Irreversible Inhibition of Transglutaminase by Sulfonium Methylketones: . . . " J. Enzyme Inhibition vol. 6(3):181-194, 1992.

Reinhardt "Inhibition of Clotting Factor XIIIA in Vitro by Specific χ-Halogenmethyl Carbonyl Compounds" 1980 *Appl. Biochem* 2:495-509.

Risau "Mechanisms of angiogenesis" 1997 *Nature* 386:671-674.

Shaw "Peptidyl Sulfonium Salts" 1988 *Biol. Chem.* 263(6):2768-2772.

Skill et al., "Increases in Renal ε-(γ-Glutamyl)-Lysine Crosslinks Result from Compartment-Specific Changes in Tissue Transglutaminase in Early Experimental Diabetic Nephropathy: Pathologic Implications" 2001 *Lab. Invest.* 81(5):705-716.

Thacher, S.M. & Rice, R.H. "Keratinocyte-Specific Transglutaminase of Cultured Human Epidermal Cells: Relation to Cross-Linked Envelope Formation and Terminal Differentiation" 1985 *Cell* 40:685-695.

Van Groningen et al., "Expression of Tissue-Type Transglutaminase Correlates Positively with Metastatic Properties of Human Melanoma Cell Lines" 1995 *Int. J. Cancer* 60:383-387.

Weygand et al., "Synthese des 6-Diazo-5-oxo-L-norleucins und der 7-Diazo-6-oxo-2-L-amino-onanthsaure" 1958 *Chem. Ber.* 91:1037-1040.

10ug of protein/lane

SNc    SNx    SNx + 281    SNx + 283

AMINO ACID DERIVATIVES AND PHARMACEUTICAL USES THEREOF

CROSS REFERENCE TO RELATED APPLICATIONS

This application is the National Stage of International Application No. PCT/GB2004/002569, filed Jun. 16, 2004, which claims the benefit of British Patent Application Ser. No. 2003-0314262.7, filed on Jun. 19, 2003. The contents of both of which are hereby incorporated by reference in their entireties.

The present invention provides compounds and methods for using the same in medicine. In particular, the present invention provides compounds and methods for inhibiting human diseases and/or processes wherein transglutaminase-mediated protein modification occurs, such as fibrosis, scarring and cancer.

Transglutaminases (TGases) are an important class of protein crosslinking enzymes that catalyse protein aggregation reactions in blood coagulation (Greenberg, C. S., et al., 1991, FASEB J. 5, 3071-3077), skin maturation (Thacher, S. M. & Rice, R. H., 1985, Cell 40, 685-695) and the clotting of seminal secretions (Dubbink H. J., et al., 1999, Lab. Invest. 79, 141-150). The most widespread member of the family is the cellular form of the enzyme, tissue transglutaminase (tT-Gase), which is expressed in varying amounts in many cell types. Like the well-characterised plasma TGase (blood coagulation factor XIIIa) (Greenberg, C. S., et al., 1991, FASEB J. 5, 3071-3077) and keratinocyte TGase (Thacher, S. M. & Rice, R. H., 1985, Cell 40, 685-695), tTGases are calcium-dependent enzymes that catalyse the formation of crosslinks proteins via ε(γ-glutamyl) isopeptide bonds and the incorporation of polyamines at certain glutamine residues (Greenberg, C. S., et al., 1991, FASEB J. 5, 3071-3077). However, tTGase is unique in the transglutaminase family of enzymes in that is able to bind and hydrolyze GTP and AIP (Achyuthan, K. E. & Greenberg, C. S., 1987, J. Biol. Chem. 262, 1901-1906), and to bind to fibronectin (Achyuthan, K. E., et al., 1995, J. Immunol. Methods 180, 67-79).

Tissue TGase is predominantly located in the cytosol, although tTGase has also been reported to exist in the nucleus resort, M., et al., 1998, J. Biol. Chem. 273, 11991-11994), at the cell surface and in the extracellular matrix (Martinez, J., et al., 1994, Biochemistry 33, 2538-2545). The enzyme is highly expressed in endothelial cells (Greenberg, C. S., et al., 1987, Blood 20, 702-709) and its activity at the surface of such cells is lo thought to enhance basement membrane stabilisation, cell spreading and cell adhesion (Martinez, J., et al., 1994, Biochemistry 33, 2538-2545; Greenberg, C. S., et al., 1987, Blood 20, 702-709; Kinsella, M. G. & Wight, T. N., 1990, J. Biol. Chem. 265, 17891-17896; Jones, R. A., et al., 1997, J. Cell Sci. 110, 2461-2472; Gaudry C. A., et al., 1999, Exp. Cell Res. 252, 104-113). However, the overall significance of the high amount of enzyme in this cell type and its biological function is poorly understood.

Protein modification mediated by tissue transglutaminases has been implicated in the pathology and aetiology of numerous diseases and processes (see review by Aeschlimann & Thomazy, 2000, Connective Tissue Research 41(1):1-27). For example, tTGase-mediated protein modification has been shown in occur in fibrosis and scarring (Johnson et al., 1999, J. Am. Soc. Neph. 10:2146-2157), neurodegenerative diseases including Huntington's disease and Alzheimer's disease (Citron et al, 1999, J. Biol. Chem. 276:3295-3301), coeliac disease (Marzari et al., 2001, J. Immunol. 166:4170-4176), thrombosis (Ariens et al. 2002, Blood 100, 743-754), cancer (Van Groningen et al., 1995, Int. J. Cancer 60:383-387; Mehta, 1994, J. Cancer 58:400-406; Mehta et al., 2002, J. Natl. Cancer Inst. 94:1652-1654), AIDS (Amendola et al., 2002, J. Immunol. Methods 265:149-159), psoriasis and inflammatory diseases of the joints (Johnson et al., 2001, Am. J. Pathol. 159:149-163). Tissue TGase has also been implicated in a number of diseases involving angiogenesis, such as the development of solid Amours and rheumatoid arthritis (Folkman, J., 1995, Nat. Med. 1, 27-31).

Hence, tTGase represents a potential target in the development of new treatments of such diseases and disorders.

Several classes of transglutaminase inhibitor compounds are known in the art, including competitive amine inhibitors, competitive glutamine inhibitors and irreversible inhibitors. Competitive amine inhibitors include dansylcadaverines (Lorand et al., 1966, Biochem. Biophys. Res. Commun. 25, 629; Lorand et al., 1968, Biochemistry 7, 1214) and N-phenyl-N'-(ω-aminoalkyl)thioureas (Lee et al., 1985, J. Biol. Chem. 260, 14689). Competitive glutamine inhibitors include aliphatic amides (Gross & Folk, 1973, J. Biol. Chem. 248, 1301), dipeptides (Gross & Folk, 1973, J. Biol. Chem. 248, 6534) and polypeptides (Gorman & Folk, 1984, J. Biol. Chem. 259, 9007). Irreversible inhibitors include iodoacetamide (Gross & Folk, 1973, J. Biol. Chem. 248, 6534; Folk & Cole, 1966, J. Biol. Chem. 241, 5518), phenol-containing halomethyl ketones (Folk & Gross, 1971, J. Biol. Chem. 246, 6683), alkyl isocyanates (Gross et al., 1975, J. Biol. Chem. 250, 7693), α-halomethylcarbonyl inhibitors (Reinhardt, 1980, Appl. Biochem. 2, 495), dihydroisoazoles (U.S. Pat. No. 4,912,120), azoles, azolium salts (U.S. Pat. No. 4,968,713, thiadiazoles (Keillor, 2001, Biorg. Med. Chem. 9, 3231), and epoxides (Keillor, 2002, Biorg. Med. Chem. 10, 355).

More recently, Pluira et al. (1992) J. Enzyme Inhibition 6, 181-94 reported irreversible inhibition of transglutaminases by sulfonium methylketones (see also U.S. Pat. No. 4,912, 120).

The present invention seeks to provide novel transglutaminase inhibitor compounds suitable for use as therapeutic agents.

SUMMARY OF THE INVENTION

According to a first aspect of the invention, there is provided a compound of Formula I:

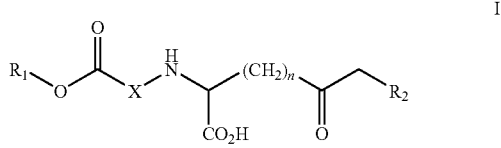

wherein:
'X' represents an amino acid group;
'n' is an integer between 1 and 4;
'R$_1$' represents benzyl, t-butyl or 9-fluorenylmethyl; and
'R$_2$' represents

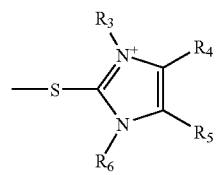

wherein $R_3$, $R_4$, $R_5$ and $R_6$ each independently represent lower alkyl or —$S^+R_7R_8$, wherein $R_7$ and $R_8$ each independently represent lower alkyl or a pharmaceutically and/or veterinarily acceptable derivative thereof.

Advantageously, X is an L-amino acid group.

Preferably, X is selected from the group consisting of phenylalanine, glutamine (including N-substituted derivatives thereof, such as N-substituted piperidinyl and propyl derivatives), isoleucine, alanine, glycine, tyrosine, proline, serine, lysine and glutamic acid. Thus, preferred compounds of the invention include N-benzyloxycarbonyl-L-glutamyl-γ-isopropylamide-6-dimethyl-sulfonium-5-oxo-L-norleucine bromide salt and N-benzyloxycarbonyl-L-glutamyl-γ-piperidinamide-6-dimethylsulfonium-5-oxo-L-norleucine bromide salt.

In a preferred embodiment of the first aspect of the invention, 'n' is 2.

Advantageously, '$R_1$' is benzyl.

Conveniently, '$R_2$' represents

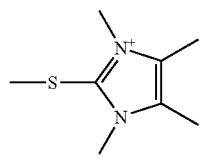

Preferably, '$R_2$' represents —$S^+R_7R_8$, wherein $R_7$ and $R_8$ each independently represent lower alkyl.

The term "lower alkyl" is intended to include linear or branched, cyclic or acyclic, $C_1$-$C_5$ alkyl, which may be saturated or unsaturated. Lower alkyl groups which $R_3$, $R_4$, $R_5$, $R_6$, $R_7$ and/or $R_8$ may represent include $C_1$-$C_4$ alkyl, $C_1$-$C_3$ alkyl, $C_1$-$C_2$ alkyl, $C_2$-$C_5$ alkyl, $C_3$-$C_5$ alkyl, $C_4$-$C_5$ alkyl, $C_2$-$C_4$ alkyl, $C_2$-$C_3$ alkyl and $C_3$-$C_4$ alkyl. Preferred lower alkyl groups which $R_3$, $R_4$, $R_5$, $R_6$, $R_7$ and/or $R_8$ may represent include $C_1$, $C_2$, $C_3$, $C_4$ and $C_5$ alkyl.

Preferably, $R_3$, $R_4$, $R_5$, $R_6$, $R_7$ and/or $R_8$ are —$CH_3$ or —$CHCH_2$. More preferably, $R_3$, $R_4$, $R_5$, $R_6$, $R_7$ and/or $R_8$ are $CH_3$.

In a preferred embodiment of the first aspect of the invention, the compound is selected from the group consisting of:

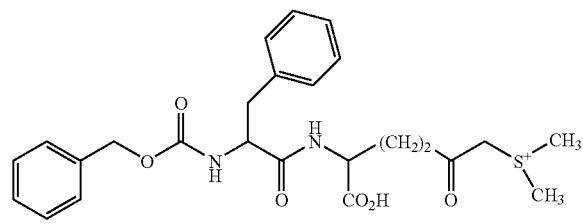

(a) N-Benzyloxycarbonyl-L-phenylalanyl-6-dimethylsulfonium-5-oxo-L-norleucine ("Compound 281")

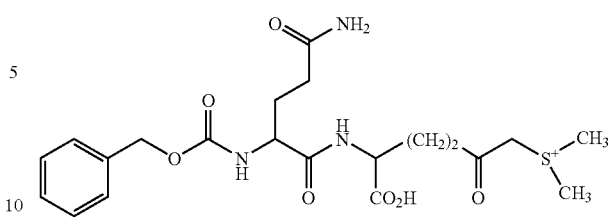

(b) N-Benzyloxycarbonyl-L-glutaminyl-6-dimethylsulfonium-5-oxo-L-norleucine ("Compound 285")

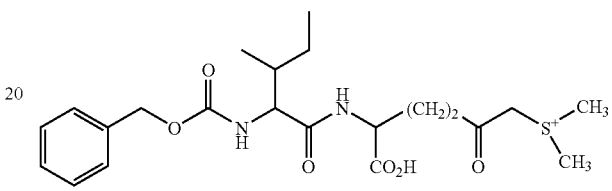

(c) N-Benzyloxycarbonyl-L-isoleucinal-6-dimethylsulfonium-5-oxo-L-norleucine ("Compound 286")

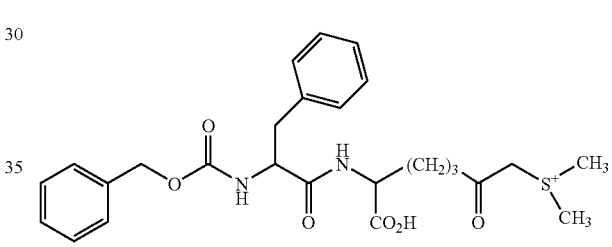

(d) N-Benzyoxycarbonyl-L-phenylalanyl-7-dimethyl-sulfonium-6-oxo-heptanoic acid ("Compound 288")

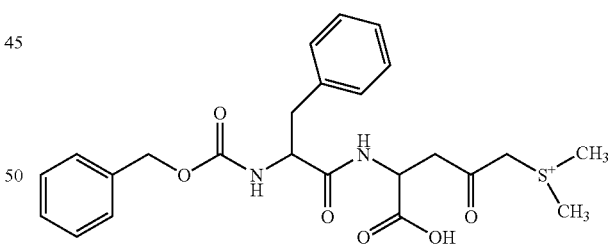

(e) N-Benzyloxycarbonyl-L-phenylalanyl-L-5-dimethylsulfonium-4-oxo-norvaline ("Compound 289")

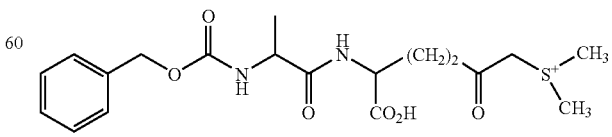

(f) N-Benzyloxycarbonyl-L-alaninal-6-dimethylsulfonium-5-oxo-L-norleucine ("Compound 291")

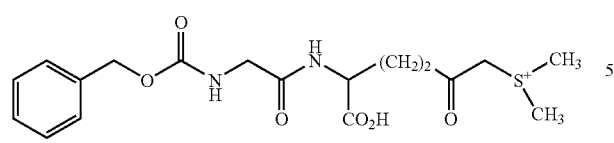

(g) N-Benzyloxycarbonyl-L-glycinal-6-dimethylsulfonium-5-oxo-L-norleucine ("Compound 292")

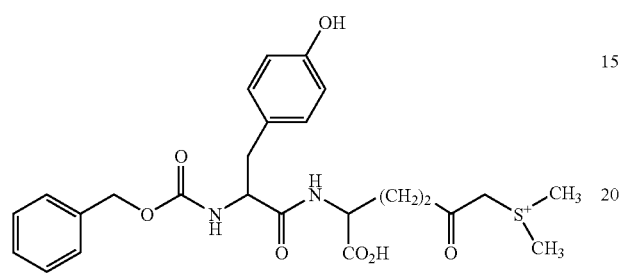

(h) N-Benzyloxycarbonyl-L-tyrosinal-6-dimethylsulfonium-5-oxo-L-norleucine ("Compound 293")

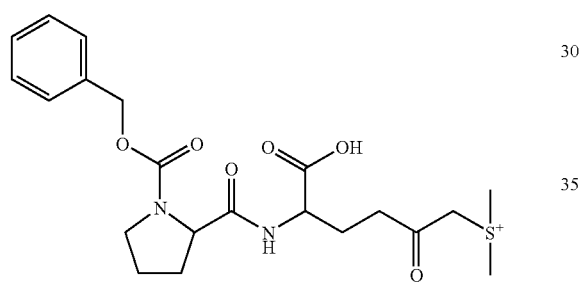

(i) N-Benzyloxycarbonyl-L-prolinyl-6-dimethylsulfonium-5-oxo-L-norleucine ("Compound 294")

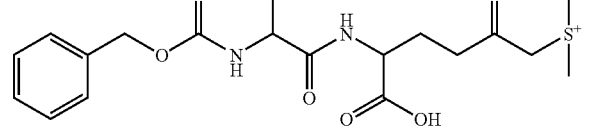

(j) N-Benzyloxycarbonyl-L-serinyl-6-dimethylsulfonium-5-oxo-L-norleucine ("Compound 295")

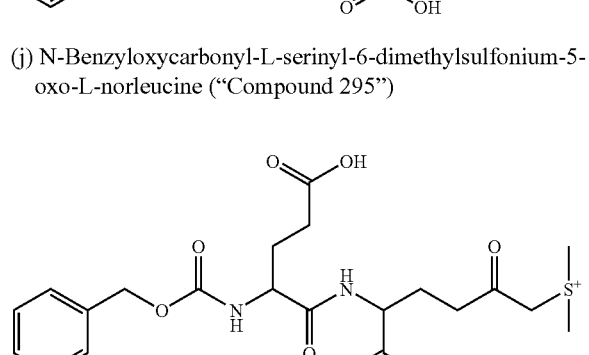

(k) N-Benzyloxycarbonyl-L-glutaminyl-6-dimethylsulfonium-5-oxo-L-norleucine ("Compound 296")

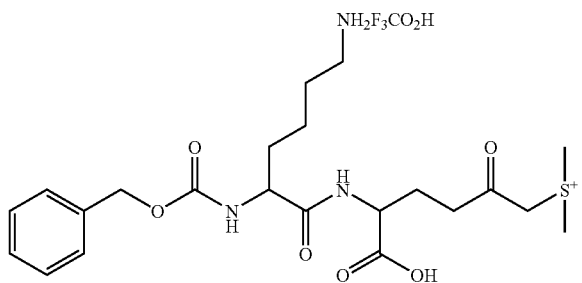

(l) N-α-Benzyloxycarbonyl-N-ε-trifluoroacetate-L-lysinyl-6-dimethylsulfonium-5-oxo-L-norleucine ("Compound 297")

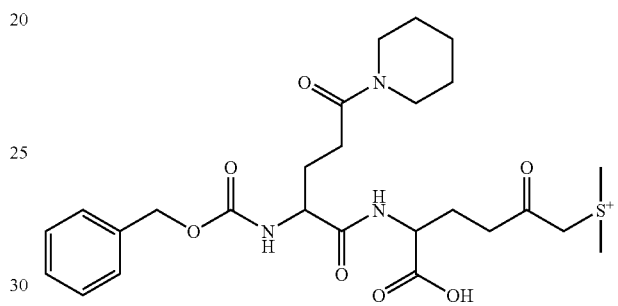

(m) N-α-Benzyloxycarbonyl-γ-piperidinyl-L-glutaminyl-6-dimethylsulfonium-5-oxo-L-norleucine ("Compound 298")

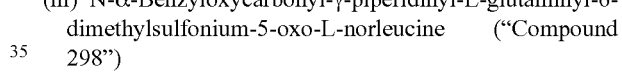

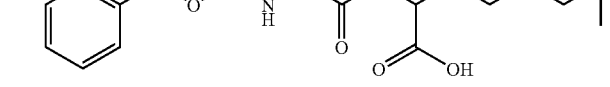

(n) N-α-Benzyloxycarbonyl-γ-propyl-L-glutaminyl-6-dimethylsulfonium-5-oxo-L-norleucine ("Compound 299")

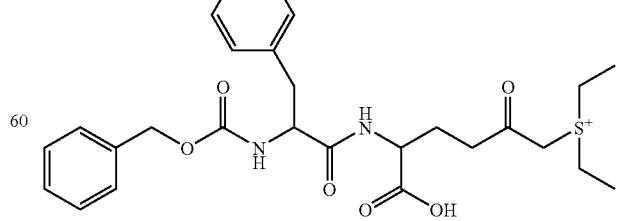

(o) N-Benzyloxycarbonyl-L-phenylalanyl-6-diethylsulfonium-5-oxo-L-norleucine ("Compound 300")

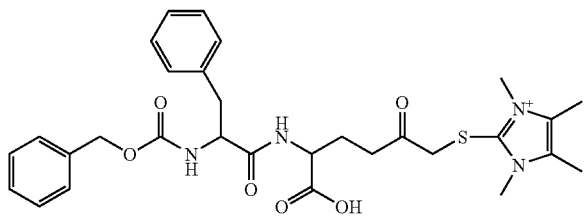

(p) N-α-Benzyloxycarbonyl-L-phenylalanyl-6-tetra-methylmercaptoimidazole-5-oxo-L-norleucine ("Compound 301")

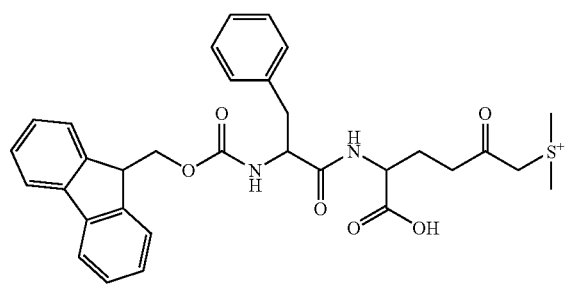

(q) N-9-Fluorenylmethyloxycarbonyl-L-phenylalanyl-6-dimethylsulfonium-5-oxo-L-norleucine ("Compound 302")

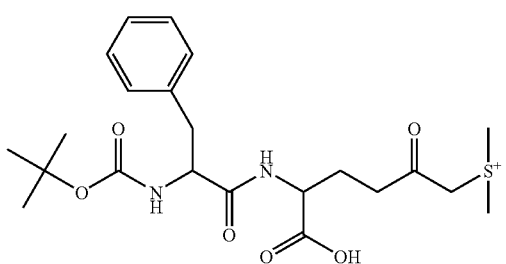

(r) N-α-tert-butyloxycarbonyl-L-phenylalanyl-6-dimethylsulfonium-5-oxo-L-norleucine ("Compound 303")

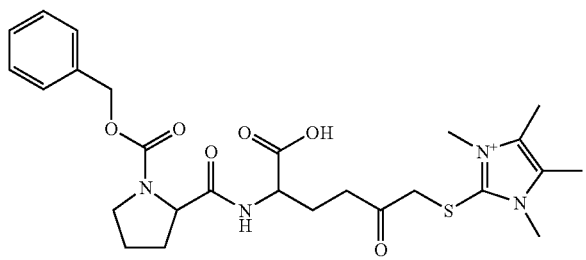

(s) N-α-Benzyloxycarbonyl-L-prolinyl-6-tetra-methylmercaptoimidazole-5-oxo-L-norleucine ("Compound 304")

It will be appreciated by persons skilled in the art that pharmaceutically, and/or veterinarily, acceptable derivatives of the compounds of formula I, such as salts and solvates, are also included within the scope of the is invention. Salts which may be mentioned include: acid addition salts, for example, salts formed with inorganic acids such as hydrochloric, hydrobromic, sulfuric and phosphoric acid, with carboxylic acids or with organo-sulfonic acids; base addition salts; metal salts formed with bases, for example, the sodium and potassium salts.

Thus, the compounds of formula I may be counterbalanced by counter-anions. Exemplary counter-anions include, but are not limited to, halides (e.g. fluoride, chloride and bromide), sulfates (e.g. decylsulfate), nitrates, perchlorates, sulfonates (e.g. methane-sulfonate) and trifluoroacetate. Other suitable counter-anions will be well known to persons skilled in the art.

Preferably, the compound is a bromide salt.

It will be further appreciated by skilled persons that the compounds of formula I may exhibit tautomerism. All tautomeric forms and mixtures thereof are included within the scope of the invention.

Compounds of formula I may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

Preferably, the compounds of the first aspect of the invention comprise L-amino acid groups.

A second aspect of the invention provides a pharmaceutical formulation comprising a compound according to the first aspect of the invention and a pharmaceutically acceptable carrier.

By 'pharmaceutically acceptable carrier' we include a substantially non-toxic, pyrogen-free excipient or adjuvant.

The formulation according to the second aspect of the invention may conveniently be presented in unit dosage form and may be prepared by any of the methods well known in the art of pharmacy. Such methods include the step of bringing into association the active ingredient (i.e. a compound is according to the first aspect of the invention) with the carrier which constitutes one or more accessory ingredients. In general, the formulations are prepared by uniformly and intimately bringing into association the active ingredient with liquid carriers or finely divided solid carriers or both, and then, if necessary, shaping the product.

formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. It will be appreciated by those skilled in the art that the compounds for oral administration should preferably be formulated so as to be protected in the gut and to permit bioadsorption.

formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, is daily sub-dose or an appropriate fraction thereof, of an active ingredient.

A third aspect of the invention provides a method of making a compound according to the first aspect of the invention comprising the following steps:
(a) reacting an N-α-protected (e.g. CBZ, FMOC or BOC protected) amino acid N-hydroxy-succinimide or para-nitrophenyl ester with 6-diazo-5-oxo-L-norleucine, and treating the resulting coupled product with hydrogen bromide; and
(b) reacting the bromomethyl ketone produced in step (a) with dimethyl sulphide, diethyl sulphide or 1,3,4,5-tetra-methyl mercapto-imidazoline-2-thione.

N-α-protected amino acid N-hydroxy-succinimide esters are commercially available, for example from Novabiochem (Calbiochem), Laufelfingen, Switzerland and Bachem (UK) Ltd, St Helens, UK.

6-Diazo-5-oxo-L-norleucine (DON) is also commercially available (Sigma-Aldrich, Cat. No. D2141). Alternatively, DON may be synthesised, for example as described in Coutts & Saint (1998) *Tetrahedron Lett.* 39:3243.

Preferably, step (a) comprises reacting the N-α-protected amino acid N-hydroxy-succinimide or para-nitrophenyl ester with 6-diazo-5-oxo-L-norleucine in the presence of tetrahydrofuran (TBF), water and triethylamine followed by reacting the products thereof with hydrogen bromide in the presence of ethyl acetate.

Advantageously, the N-α-protected amino acid N-hydroxy-succinimide or para-nitrophenyl ester is a N-α-CBZ-protected amino acid N-hydroxy-succinimide or para-nitrophenyl ester selected from the group consisting of N-α-CBZ-L-phenylalanine N-hydroxy-succinimide ester, N-α-CBZ-L-glutamine N-hydroxy-succinimide ester, N-α-CBZ-L-isoleucine N-hydroxy-succinimide ester, N-α-CBZ-L-alaninal N-hydroxy-succinimide ester, N-α-CBZ-L-glycine N-hydroxy-succinimide ester, N-α-CBZ-L-proline N-hydroxy-succinimide ester, N-α-CBZ-L-serine N-hydroxysuccinimide ester, N-α-CBZ-L-tyrosine N-hydroxysuccinimide ester, N-α-CBZ-L-glutamic acid N-hydroxysuccinimide ester, N-α-CBZ-L-lysine N-hydroxysuccinimide ester and N-α-CBZ-L-tyrosine para-nitrophenyl ester.

A fourth aspect of the invention provides a method of treating a subject in need of treatment with a transglutaminase inhibitor comprising administering to said subject a compound according to the first aspect of the invention or a pharmaceutical formulation according to the second aspect of the invention.

Preferably, the compound according to the first aspect of the invention or a pharmaceutical formulation according to the second aspect of the invention is administered in an amount sufficient to inhibit, at least in part, tTGase-mediated protein modification (i.e. cross-linking). More preferably, the compound or formulation is administered in an amount sufficient to inhibit tTGase-mediated protein cross-linking by at least 10%, for example, at least 20%, 30%, 40%, 50%, 60%, 70%, 80%, 90% or 95%. Most preferably, the compound or formulation is administered in an amount sufficient to inhibit completely tTGase-mediated protein cross-linking.

TGase-mediated protein modification may be measured by methods known in the art. For example, detection of the isodipeptide ε(γ-glutamyl)lysine in body fluids can be used as an indirect measure of the frequency of crosslinking in diseases which involve this protein cross link. Hence, a reduction of the isodipeptide in the body fluid provides an indirect measure of reduced protein crosslinking (see Nemes et al., 2002, *Minerva Biotechnology* 14, 183).

Alternatively, a tissue biopsy may be taken and analysed, for example by ion exchange or reversed phase BPLC after proteolytic digestion of the material (Griffin & Wilson, 1984, *Mol. Cell Biochem.* 58:37-49), or by staining biopsy sections and analysing by immunohistochemistry (Skill et al., 2001, 81:705-716).

More preferably, the subject has a disease/disorder selected from the group consisting of fibrosis, scarring, neurodegenerative diseases (such as Huntington's disease and Alzheimer's disease), autoimmune diseases (such as coeliac disease), thrombosis, proliferative disorders (i.e. cancer), AIDS, psoriasis and inflammation (such as chronic inflammatory diseases, e.g. of the joints, including rheumatoid arthritis and osteoarthritis).

Most preferably, the fourth aspect of the invention provides a method for treating fibrosis and/or renal scarring in a subject comprising administering to said subject a compound according to the first aspect of the invention or a pharmaceutical formulation according to the second aspect of the invention in an amount sufficient to inhibit fibrosis and/or renal scarring.

By "renal scarring" we mean loss of renal architecture and cell depletion in the glomeruli and renal tubules accompanied by the increased accumulation and deposition of extracellular matrix components, such as collagen.

It will be appreciated by those skilled in the art that treatment may be prophylactic and/or therapeutic. For example, the compounds and formulations of the invention may be used to slow and/or to prevent the onset of a disease/disorder in the subject being treated. Alternatively, or in addition, the compounds and formulations of the invention may be used to reduce or eradicate the symptoms of a disease/disorder in the subject being treated.

It will be further appreciated by those skilled in the art that the compound or formulation of the first and second aspects of the invention, respectively, may be administered by any route known or developed in the art. Thus, the compound or formulation may be administered by parenteral injection (e.g. intravenous, subcutaneous or intramuscular), by inhalation or nasal administration, or orally.

Preferably, the compound or formulation is administered systemically, for example intravenously. Alternatively, the compound or formulation is administered topically, e.g. at or near a target site where TGase-mediated protein modification is to be inhibited.

Treatment with a compound or formulation according to the invention may consist of a single dose or a plurality of doses over a period of time. Advantageously, the compound or formulation is administered repeatedly.

Compounds and formulations of the invention may also be administered by a surgically implanted device that releases the compound or formulation directly to the required site, for example in the vicinity of a solid tumour.

It will be appreciated by persons skilled in the art that a subject treated using the method according to the fourth aspect of the invention may be any mammal. Preferably, the subject is human. Alternatively, the subject is a dog, cat, horse, or other domestic or farm mammalian animal.

In a preferred embodiment of the method according to the fourth aspect of the invention, the subject has cancer. In alternative preferred embodiments, the method is for treating fibrosis and/or scarring in the subject.

A fifth aspect of the invention provides a compound according to the first aspect of the invention for use in medicine.

A sixth aspect of the invention provides the use of a compound according to the first aspect of the invention in the preparation of a medicament for inhibiting a transglutaminase, for example a tissue transglutaminase.

In a preferred embodiment, the medicament is for treating a disease/disorder selected from the group consisting of fibrosis, scarring (e.g. renal scarring or hypertrophic scarring of the skin), neurodegenerative diseases (such as Huntington's disease and Alzheimer's disease), autoimmune diseases (such as coeliac disease), thrombosis, proliferative disorders (i.e. cancer), AIDS, psoriasis and inflammation (such as chronic inflammatory diseases, e.g. of the joints, including rheumatoid arthritis and osteoarthritis).

Advantageously, the medicament is for treating (including inhibiting and/or preventing) fibrosis and/or scarring, and in particular renal scarring and hypertrophic scarring of the skin.

Preferably, the medicament is for treating a proliferative disorder, especially cancers manifesting themselves as solid tumours.

A seventh aspect of the invention provides a method for preventing or treating rejection of a transplanted organ comprising contacting the organ with a compound according to the first aspect of the invention or a formulation according to the second aspect of the invention. Thus, the invention provides the use of a compound according to the first aspect of the invention in the preparation of a medicament for preventing or treating rejection of a transplanted organ.

Preferably, the organ is a heart, lung, kidney or liver.

Most preferably, the organ is a kidney. Kidneys that are to be transplanted often show some upregulation of tissue transglutaminase and possibly other transglutaminases. Moreover, kidneys which are rejected after transplantation often exhibit excessive scarring and upregulation of transglutaminase activity and crosslinking (Abo-Zenah et al., 2001, *J. Am. Soc. Nephrol.* 12, 4454A). Such tissue degeneration and subsequent organ rejection may be prevented by treating the kidney (or other organ) with a transglutaminase inhibitor.

It will be appreciated that the compound or formulation may be delivered before, during and/or after transplantation of the organ. Thus, in one embodiment, the organ is treated prior to transplantation, for example by perfusing and/or bathing with a solution containing a compound according to the first aspect of the invention.

In an alternative embodiment, the organ is treated during and/or after transplantation into a patient. Advantageously, the compound or formulation is delivered at or near the site of the transplant, for example by local administration.

Preferred, non-limiting examples which embody certain aspects of the invention will now be described, with reference to the following figures in which:

Reagents and conditions for each step are as follows:
(i) Triethylamine (TEA), THF, $H_2O$;
(ii) HBr, ethyl acetate; and
(iii) Dimethyl sulphide.

FIGS. 2 to 21 show the effect of increasing concentrations of exemplary compounds of the invention (and prior art compound 1,3-dimethyl-2-(2-oxopropylsulfanyl)-3H-1,3-diazol-1-ium-chloride) on the inhibition of guinea pig liver transglutaminase (tTG), as measured by an enzyme-linked sorbent assay (ELSA) (see Example 2, below). The concentration of the test compound test is given in μM, along the x-axis. The compounds tested are as follows:

| Figure | Compound tested |
| --- | --- |
| 2 | N-Benzyloxycarbonyl-L-phenylalanyl-6-dimethylsulfonium-5-oxo-L-norleucine bromide salt ("Compound 281") |
| 3 | 1,3-dimethyl-2-(2-oxopropylsulfanyl)-3H-1,3-diazol-1-ium-chloride ("Compound 283") |
| 4 | N-Benzyloxycarbonyl-L-glutaminyl-6-dimethylsulfonium-5-oxo-L-norleucine bromide salt ("Compound 285") |
| 5 | N-Benzyloxycarbonyl-L-isoleucinal-6-dimethylsulfonium-5-oxo-L-norleucine bromide salt ("Compound 286") |
| 6 | N-Benzyoxycarbonyl-L-phenylalanyl-7-dimethylsulfonium-6-oxo-heptanoic acid bromide salt ("Compound 287") |
| 7 | N-Benzyloxycarbonyl-L-phenylalanyl-L-5-dimethylsulfonium-4-oxo-norvaline bromide salt ("Compound 289") |
| 8 | N-Benzyloxycarbonyl-L-alaninal-6-dimethylsulfonium-5-oxo-L-norleucine bromide salt ("Compound 291") |
| 9 | N-Benzyloxycarbonyl-L-glycinal-6-dimethylsulfonium-5-oxo-L-norleucine bromide salt ("Compound 292") |
| 10 | N-Benzyloxycarbonyl-L-tyrosinal-6-dimethylsulfonium-5-oxo-L-norleucine bromide salt ("Compound 293") |
| 11 | N-Benzyloxycarbonyl-L-prolinyl-6-dimethylsulfonium-5-oxo-L-norleucine bromide salt ("Compound 294") |
| 12 | N-Benzyloxycarbonyl-L-serinyl-6-dimethylsulfonium-5-oxo-L-norleucine bromide salt ("Compound 295") |
| 13 | N-Benzyloxycarbonyl-L-glutaminyl-6-dimethylsulfonium-5-oxo-L-norleucine bromide salt ("Compound 296") |
| 14 | N-α-Benzyloxycarbonyl-N-ε-trifluoroacetate-L-lysinyl-6-dimethylsulfonium-5-oxo-L-norleucine bromide salt ("Compound 297") |
| 15 | N-α-Benzyloxycarbonyl-γ-piperidinyl-L-glutaminyl-6-dimethylsulfonium-5-oxo-L-norleucine bromide salt ("Compound 298") |
| 16 | N-α-Benzyloxycarbonyl-γ-propyl-L-glutaminyl-6-dimethylsulfonium-5-oxo-L-norleucine bromide salt ("Compound 299") |
| 17 | N-Benzyloxycarbonyl-L-phenylalanyl-6-diethylsulfonium-5-oxo-L-norleucine bromide salt ("Compound 300") |
| 18 | N-Benzyloxycarbonyl-L-phenylalanyl-6-tetramethylmercaptoimidazole-5-oxo-L-norleucine bromide salt ("Compound 301") |

-continued

| Figure | Compound tested |
|---|---|
| 19 | N-9-Fluorenylmethyloxycarbonyl-L-phenylalanyl-6-dimethylsulfonium-5-oxo-L-norleucine bromide salt ("Compound 302") |
| 20 | N-α-tert-butyloxycarbonyl-L-phenylalanyl-6-dimethylsulfonium-5-oxo-L-norleucine bromide salt ("Compound 303") |
| 21 | N-Benzyloxycarbonyl-L-prolinyl-6-tetra-methylmercaptoimidazole-5-oxo-L-norleuine bromide salt ("Compound 304") |

Figure 22:
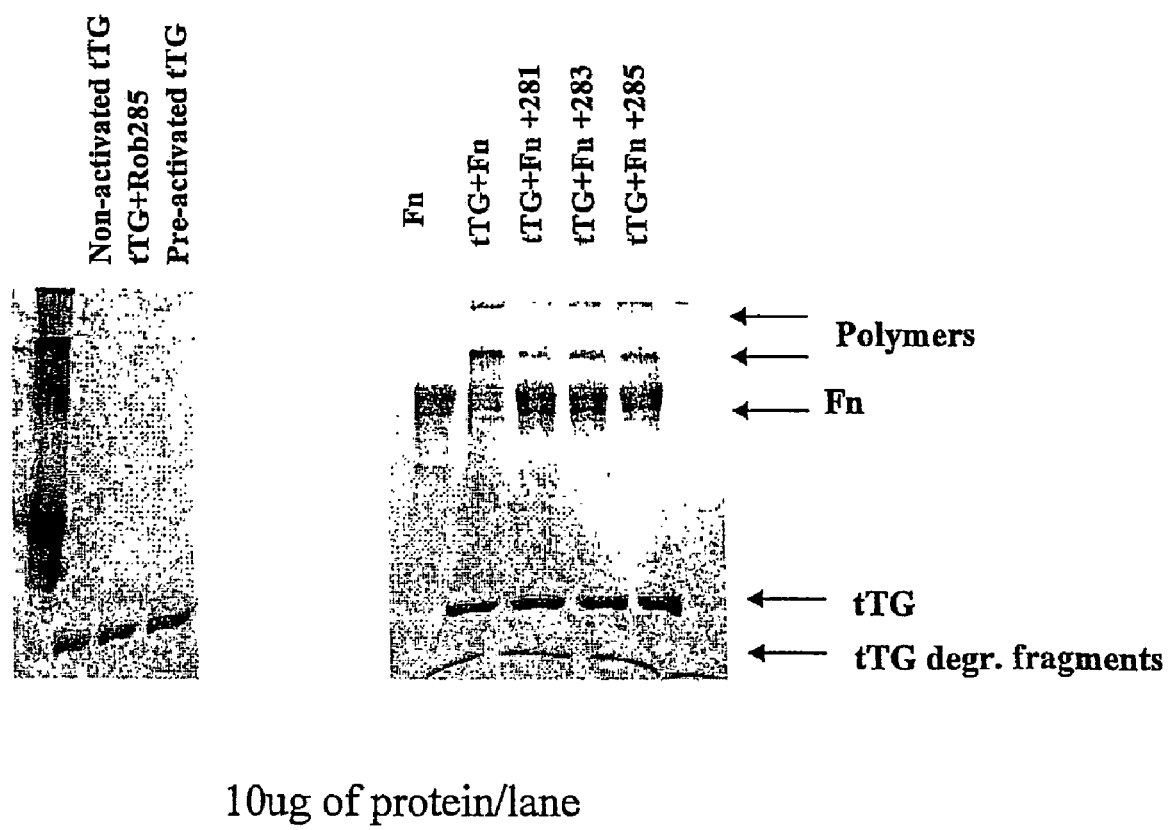

FIG. 22 shows SDS-PAGE data demonstrating inhibition of tTGase-mediated crosslinking of fibronectin following treatment with exemplary compounds of the invention (see Example 3). Key: 'tTG'=tissue transglutaminase, 'degr. fragments'=degradation fragments, 'Fn'=fibronectin, 'Polymers'=cross-linked fibronectin polymers, '281'=N-Benzyloxycarbonyl-L-phenylalanyl-6-dimethylsulfonium-5-oxo-L-norleucine bromide salt, '285'/'Rob285'=N-Benzyloxycarbonyl-L-glutaminyl-6-dimethyl-sulfonium-5-oxo-L-norleucine bromide salt.

Figure 23A:
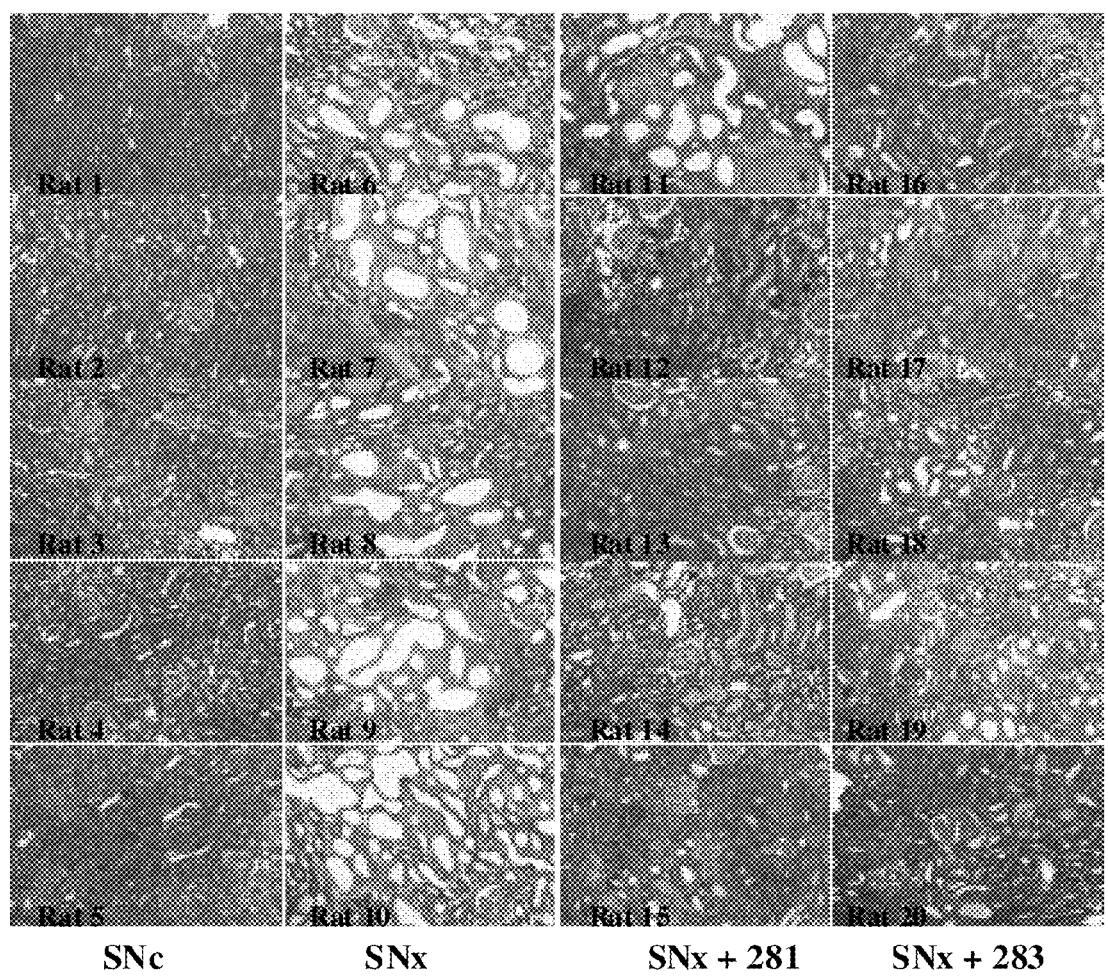
Figure 23:
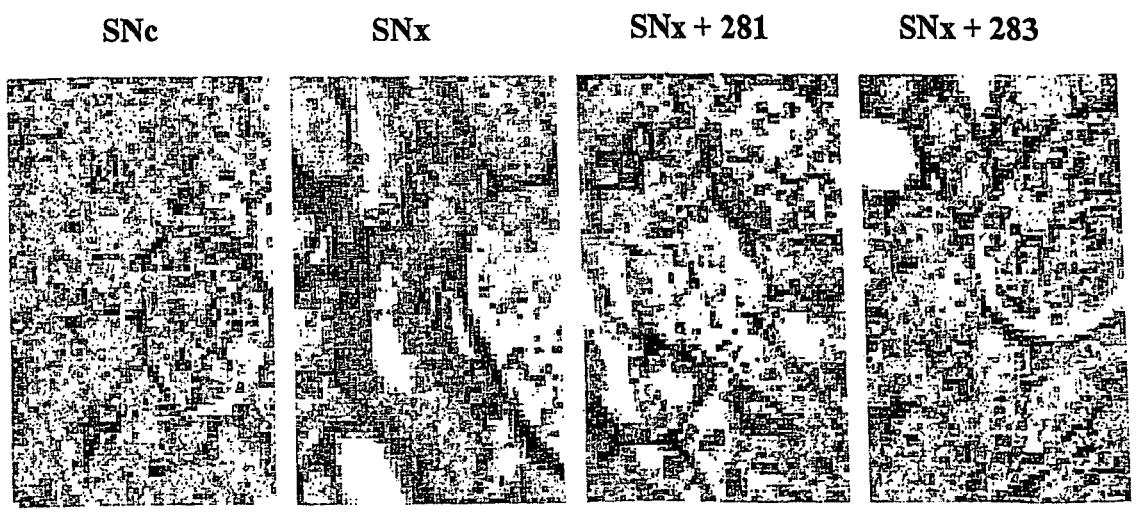

FIG. 23 shows (a) representative Masson's Trichrome stained sections at 100× magnification and (b) collagen m stained sections at 200× magnification from kidneys of rats treated for 84 days with inhibitor N-Benzyloxycarbonyl-L-phenylalanyl-6-dimethylsulfonium-5-oxo-L-nor-leucine bromide salt (designated 'SNx+281') or 1,3-dimethyl-2-(2-oxopropylsulfanyl)-3H-1,3-diazol-1-ium-chloride (designated 'SNx+283'). SNx indicates animals in which a subtotal nephrectomy has been performed. These animals either had PBS (SNx) or TGase inhibitor compound 281 or 283 (SNx+281 and SNX+283, respectively) instilled into their kidney. 'SNc' refers to sham operated animals and 'SNx' refers to animals which have had PBS instilled into their kidneys. Five animals per group were used (see Example 4).

Figure 24A:
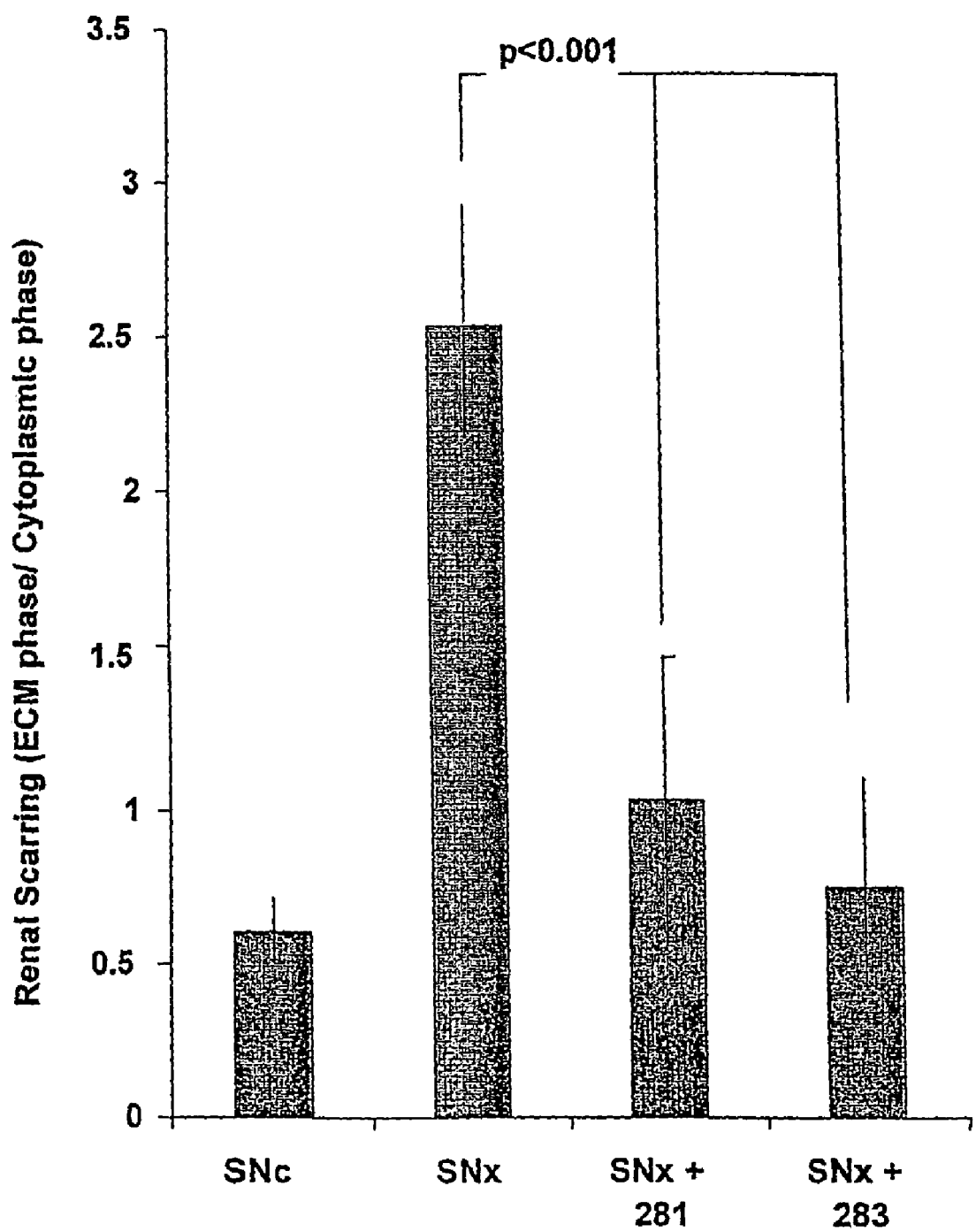
Figure 24B:
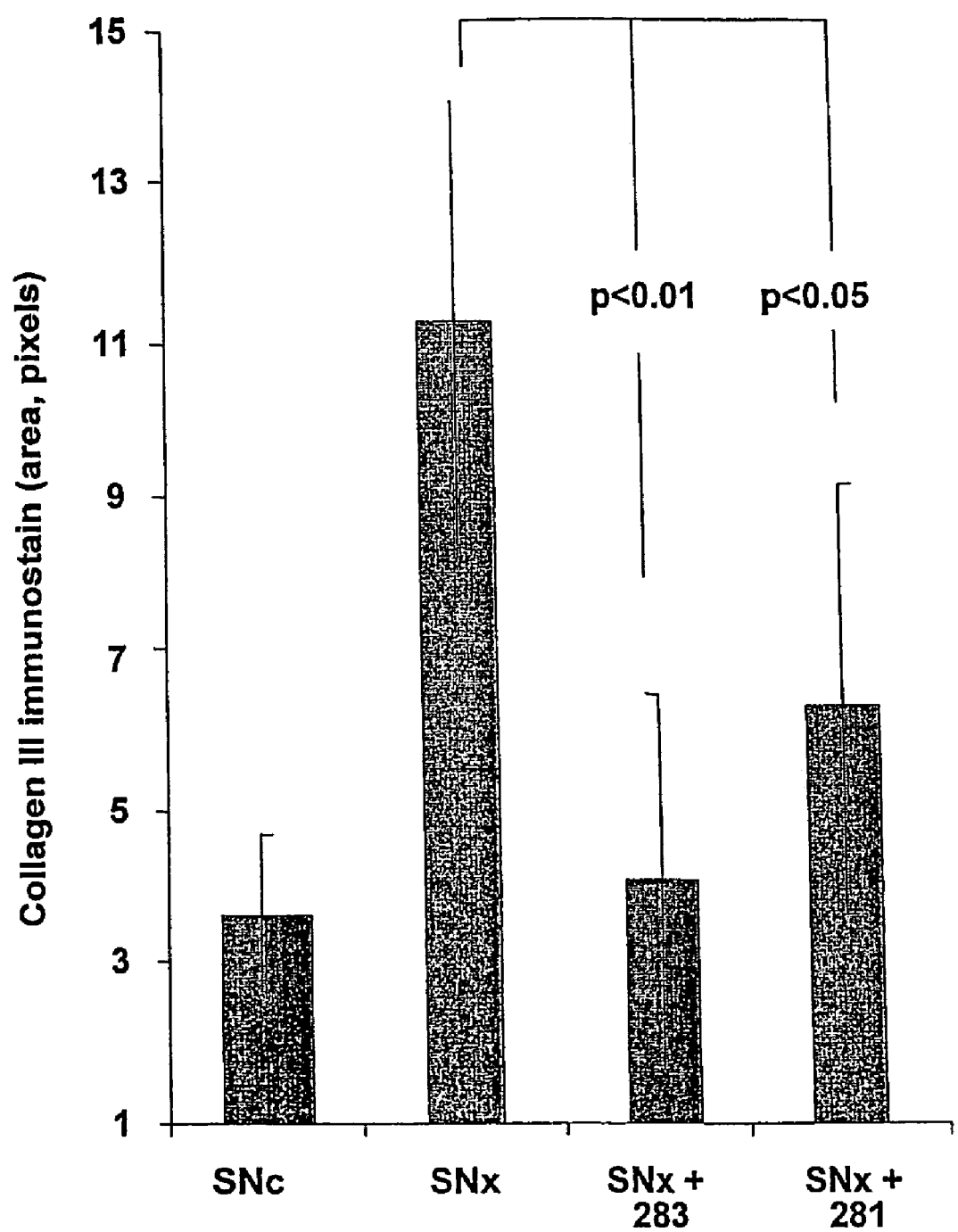

FIG. 24 shows Quantative Image Analysis of (a) Masson's Trichrome staining and (b) collagen III staining in the kidney sections from 90 day animals following treatment with inhibitor N-Benzyloxycarbonyl-L-phenylalanyl-6-dimethylsulfonium-5-oxo-L-norleucine bromide salt (designated 'SNx+281') and 1,3-dimethyl-2-(2-oxopropylsulfanyl)-3H-1,3-diazol-1-ium-chloride (designated 'SNx+283'). 'Snc' and 'SNx' are referred to as in legend to FIG. 12 above. Five animals per group were used (see Example 4).

Figure 25A:
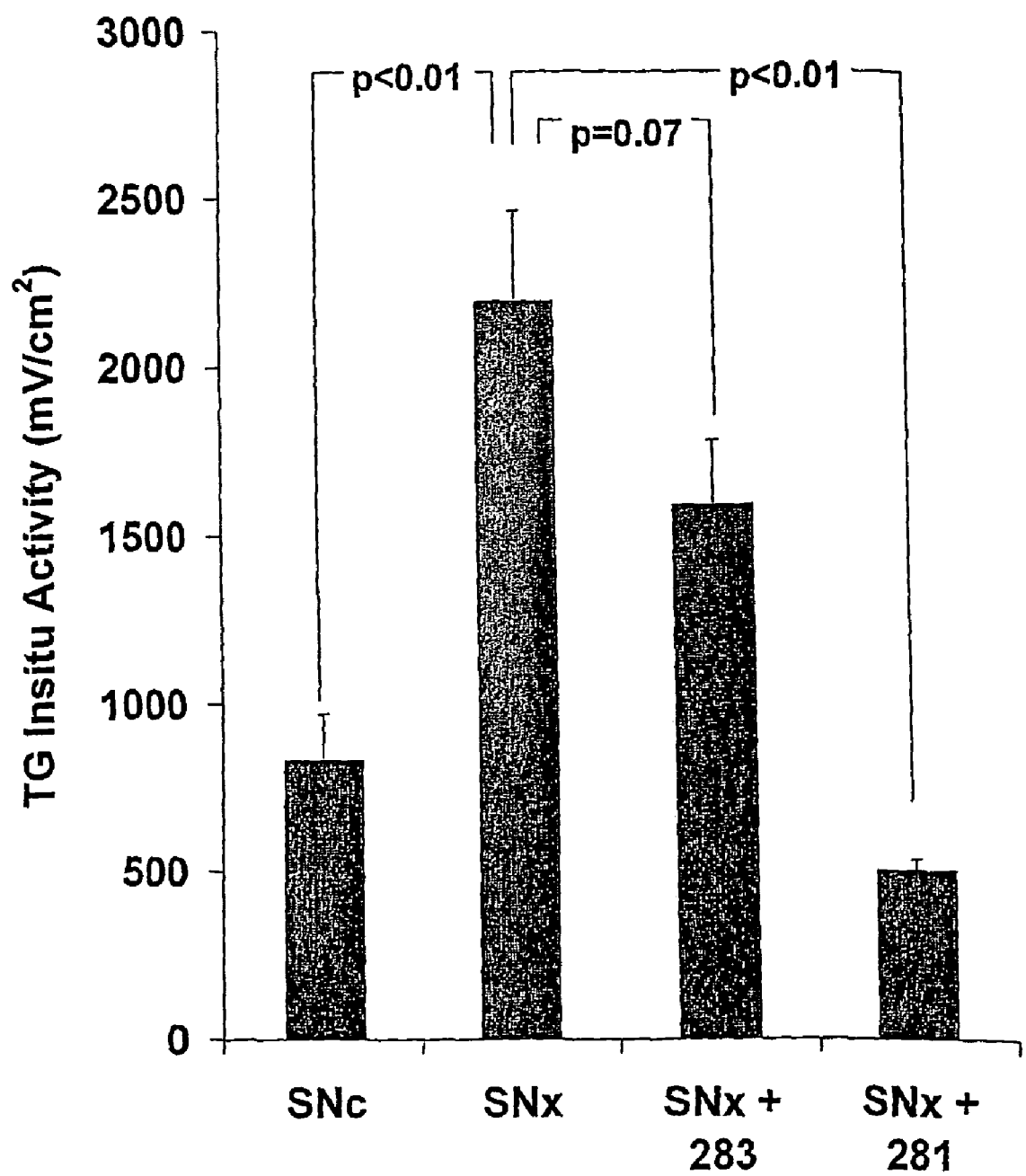
Figure 25B:
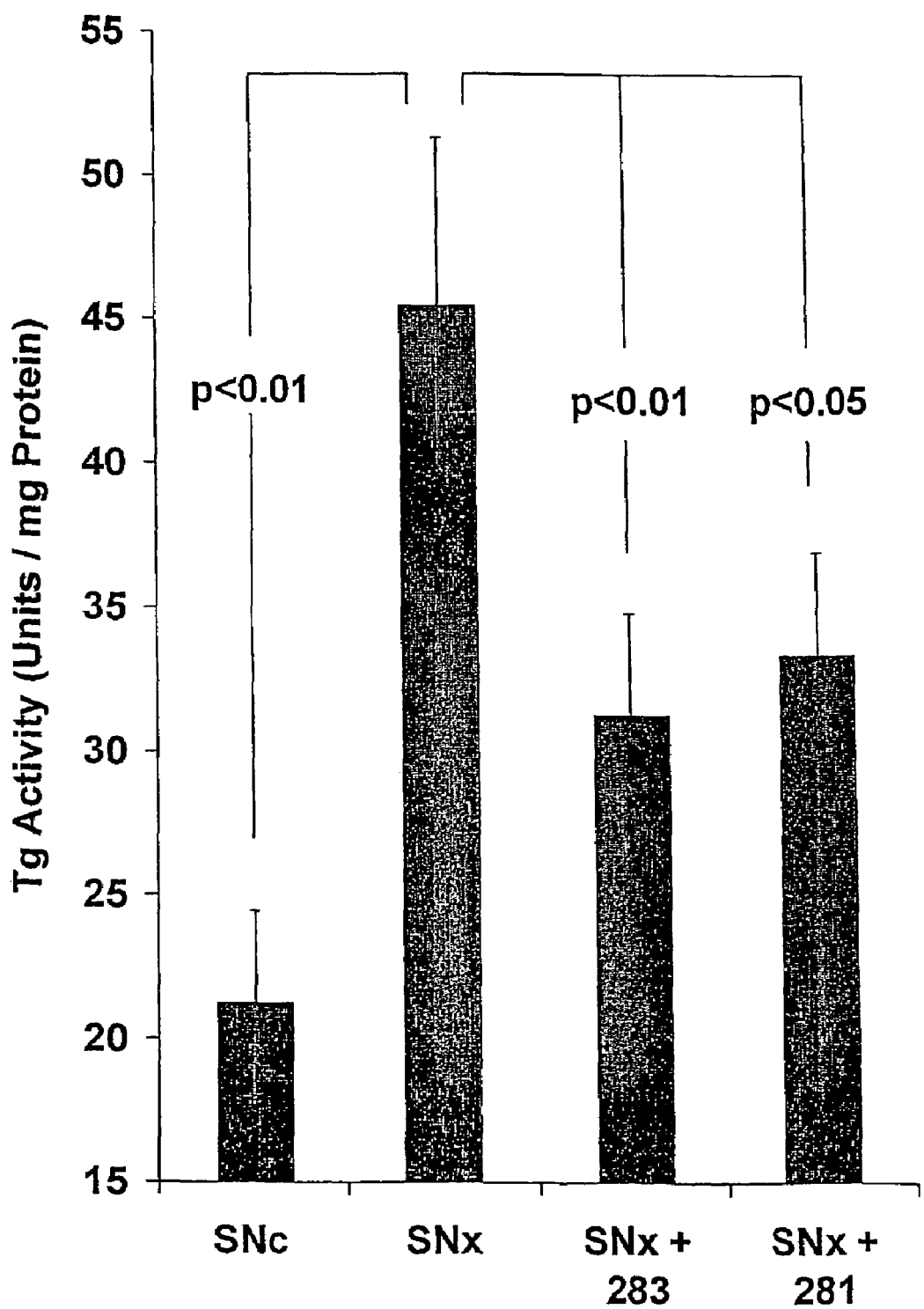

FIG. 25 shows the inhibition of TGase activity in kidneys of rats treated with compounds having TGase inhibitor activity. FIG. 25(a) is a histogram showing semi-quantative analysis of in situ TGase activity in cryostat sections taken from kidneys of SNx rats treated for 28 days with the inhibitors N-Benzyloxycarbonyl-L-phenylalanyl-6-dimethyl-sulfonium-5-oxo-L-norleucine bromide salt (designated 'SNx+281') and 1,3-dimethyl-2-(2-oxopropylsulfanyl)-3H-1,3-diazol-1-ium-chloride (designated 'SNx+283'). Data show emission from Leica confocal laser microscope from TRITC-extravidin bound to TGase incorporated biotin cadaverine. 'SNc' refers to control kidneys obtained from animals on which a sham operation was performed without subtotal nephrectomy. 'SNx' refers to subtotal nephrectomy. Inhibitors were delivered to the kidney by mini-pumps (see Example 5). FIG. 25(b) is a histogram showing TGase activity measured by $^{14}C$-putrescine incorporation into N, N'-dimethyl casein at day 84 in kidney homogenates of SNx rats treated with the inhibitors N-Benzyloxycarbonyl-L-phenylalanyl-6-di-methyl-sulfonium-5-oxo-L-norleucine bromide salt (designated 'SNx+281') and 1,3-dimethyl-2-(2-oxopropylsulfanyl)-3H-1,3-diazol-1-ium-chloride (designated 'SNx+283'). Five animals per group were used (see Example 4).

Figure 26A:
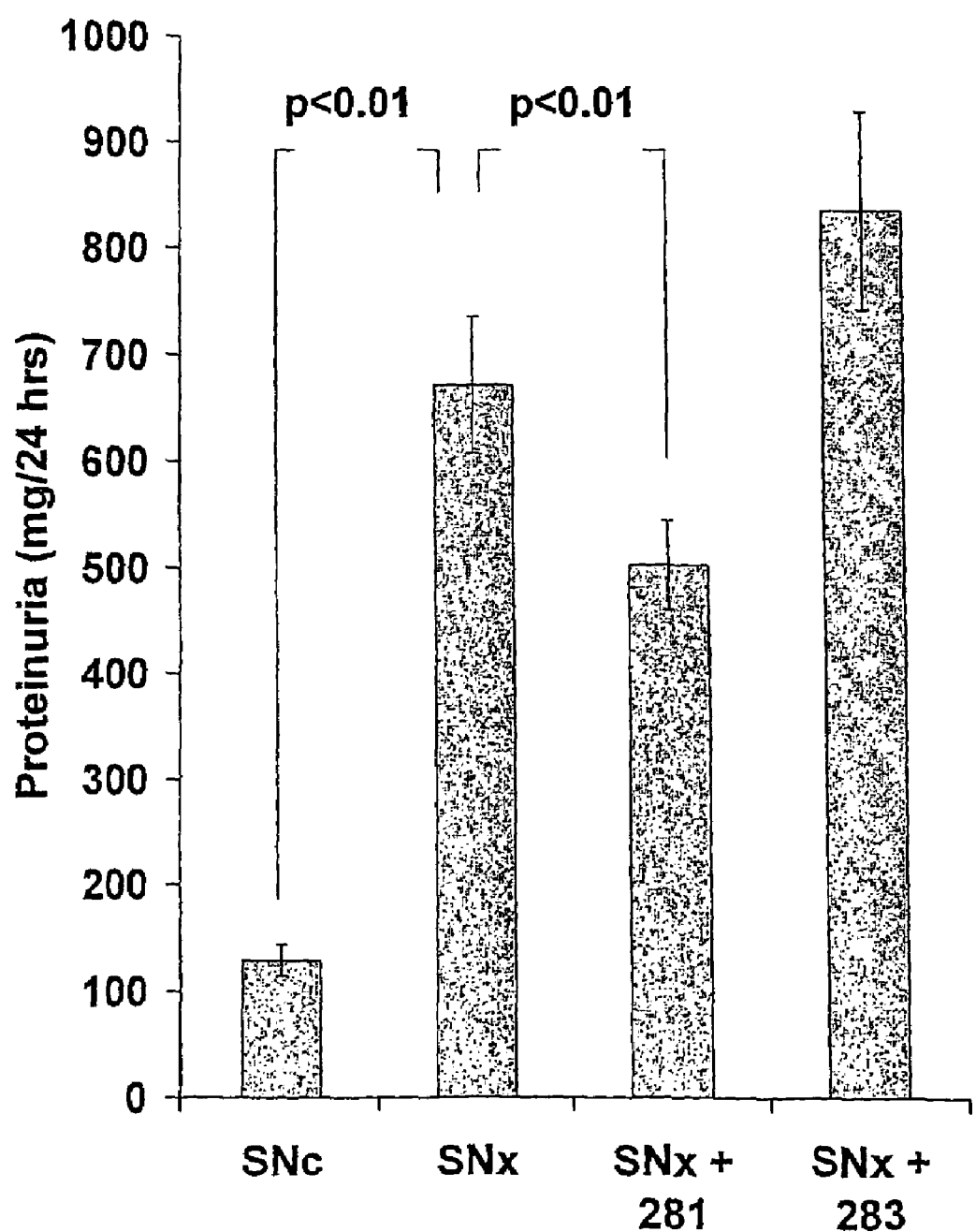
Figure 26B:
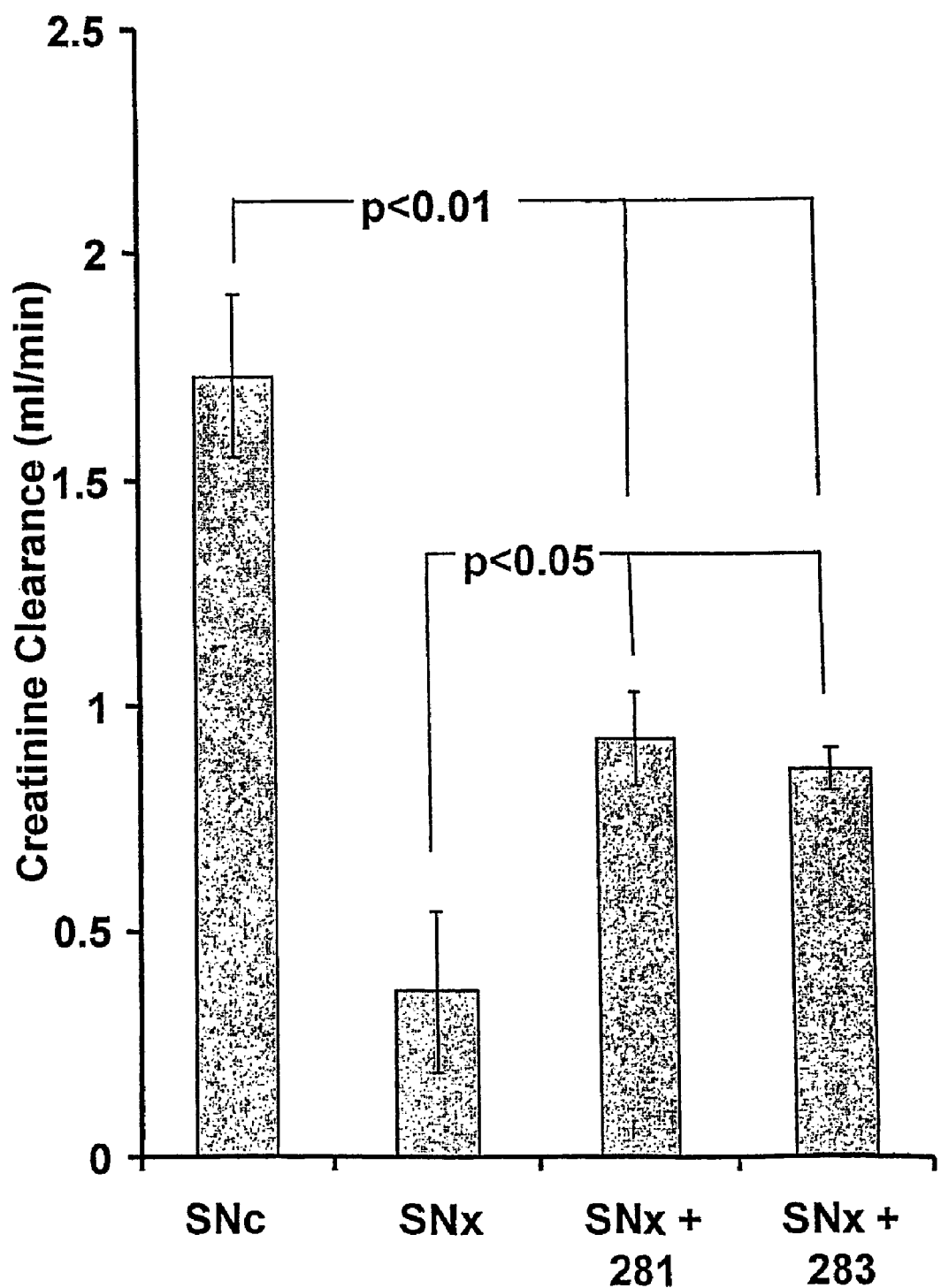

FIG. 26 (a and b) shows the effect on renal function in rats of 84 days treatment with the inhibitors N-Benzyloxycarbonyl-L-phenylalanyl-6-di-methylsulfonium-5-oxo-L-norleucine bromide salt (designated 'SNx+281') and 1,3-dimethyl-2-(2-oxopropylsulfanyl)-3H-1,3-diazol-1-ium-chloride (designated 'SNx+283'), as determined using measurements of: FIG. 26(a) proteinuria and FIG. 26(b) creatinine clearance. 'SNc' refers to control kidneys obtained from animals on which a sham operation was performed without subtotal nephrectomy. 'SNx' refers to subtotal nephrectomy. Five animals per group were used (see Example 4).

EXAMPLES

Example 1

Synthesis of Exemplary TGase Inhibitors

General Procedures

Melting points were determined on a Gallenkamp melting point apparatus and are uncorrected. IR spectra were recorded on a Perkin-Elmer 1600 series FT-IR instrument. 1H spectra were recorded on a JFOL E-270 instrument at 270 Mz. 13C spectra were recorded on the same instrument at 67.8 MHz. All NMR samples were prepared in deuteriochloroform unless otherwise stated. Chemical shifts are reported relative to the internal standard tetramethylsilane and quoted as ppm. Mass spectra were recorded on a micromass platform ESI-MS machine.

Tetrahydrofuran (THF) was freshly distilled from sodium benzophenone ketyl before use. Ether was distilled from lithium aluminium hydride and stored over sodium wire. Methanol and ethanol were distilled and stored over 5 Å molecular sieves. N,N-dimethylformamide was distilled from calcium hydride and stored over 5 Å molecular sieves. Chloroform, dichloromethane and acetone were dried over granular calcium chloride. Solvents used for flash column chromatography were distilled before use. Flash chromatography was carried out using Fluka silica gel 60, 220-240 mesh size. Thin layer chromatography was carried out using Whatman silica gel 60A F254 pre-coated glass plates.

Synthesis of 6-diazo-5-oxo-norleucine (DON)

The intermediate 6-diazo-5-oxo-L-norleucine, DON, was prepared as previously described in Coutts & Saint (1998) *Tetrahedron Lett.* 39:3243.

Synthesis of 6-bromo-5-oxo-L-norleucine Derivatives

The following intermediates were synthesised:

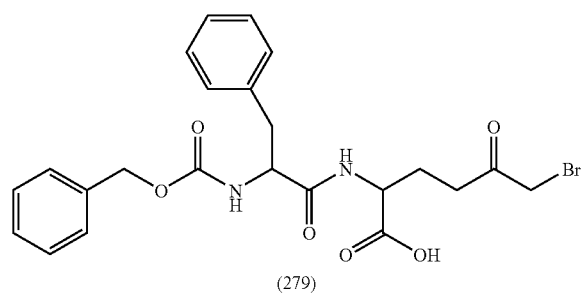

(279)

2
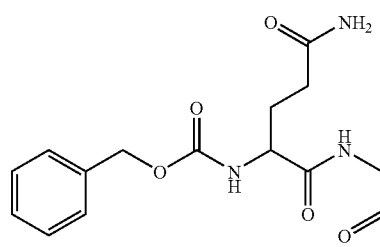
3
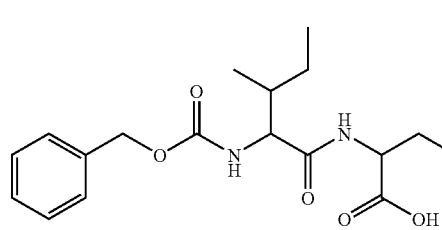
4
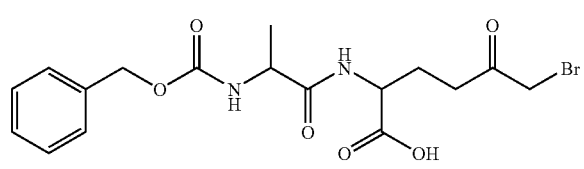
5
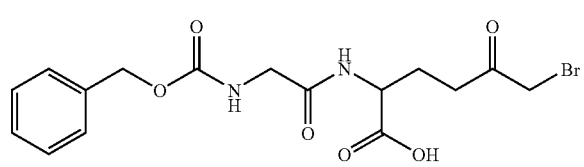
6
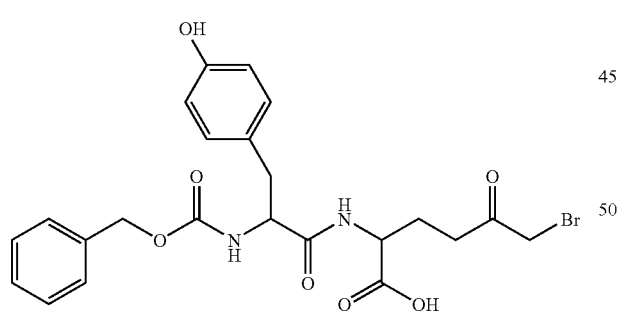
7
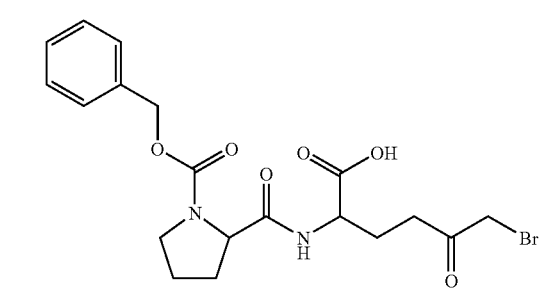
8
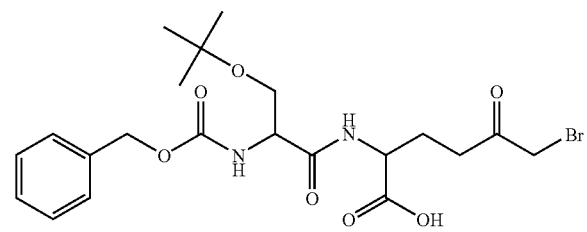
9
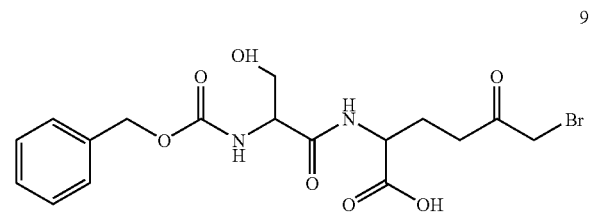
10
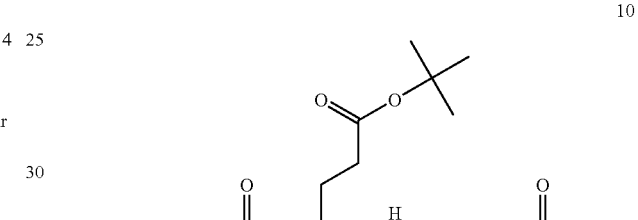
11
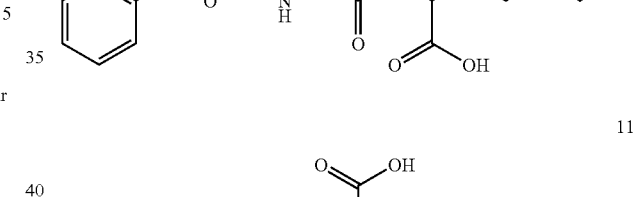
12
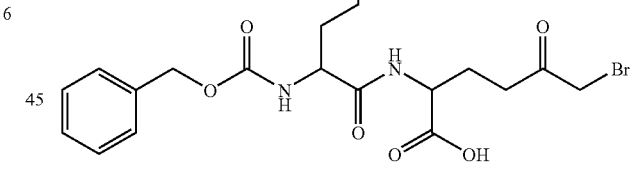
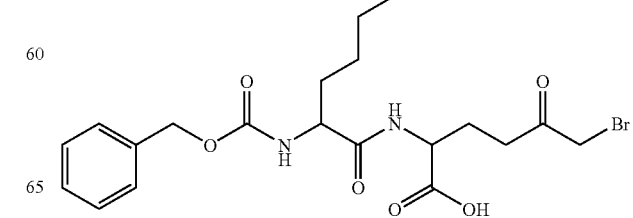

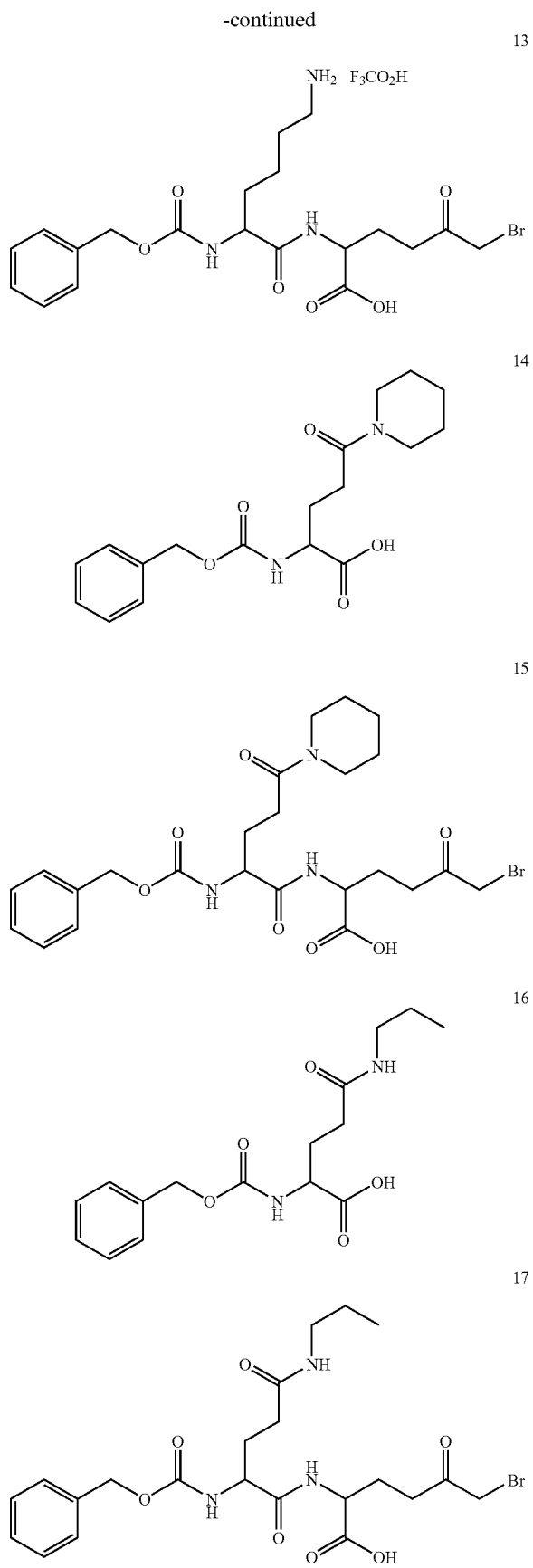

To an ice-cold solution of the appropriate N-α-protected (CBZ, FMOC or BOC) amino acid N-hydroxysuccinimide ester and DON (1 eqv.) in a 1:1 mixture of TBF/water (0.5M) was added triethylamine (1.5 eqv.). The reaction mixture was stirred for 2 h. at 0° C. and the solvent removed under high vacuum at room temperature. The residue was dissolved in ethyl acetate and treated with a 1:1 mixture of HBr and acetic acid dropwise until gas evolution ceased. The resulting mixture was stirred for a further 10 min. and ethyl acetate added and the organic layer washed with water (×3) brine (×1) and dried over $MgSO_4$. Removal of the solvent in vacuo afforded a colourless solid which was recrystallised from an appropriate solvent to give the product in typically 70-80% yield.

(a) N-α-Benzyloxycarbonyl-L-phenylalanyl-6-bromo-5-oxo-L-norleucine

Figure 1:
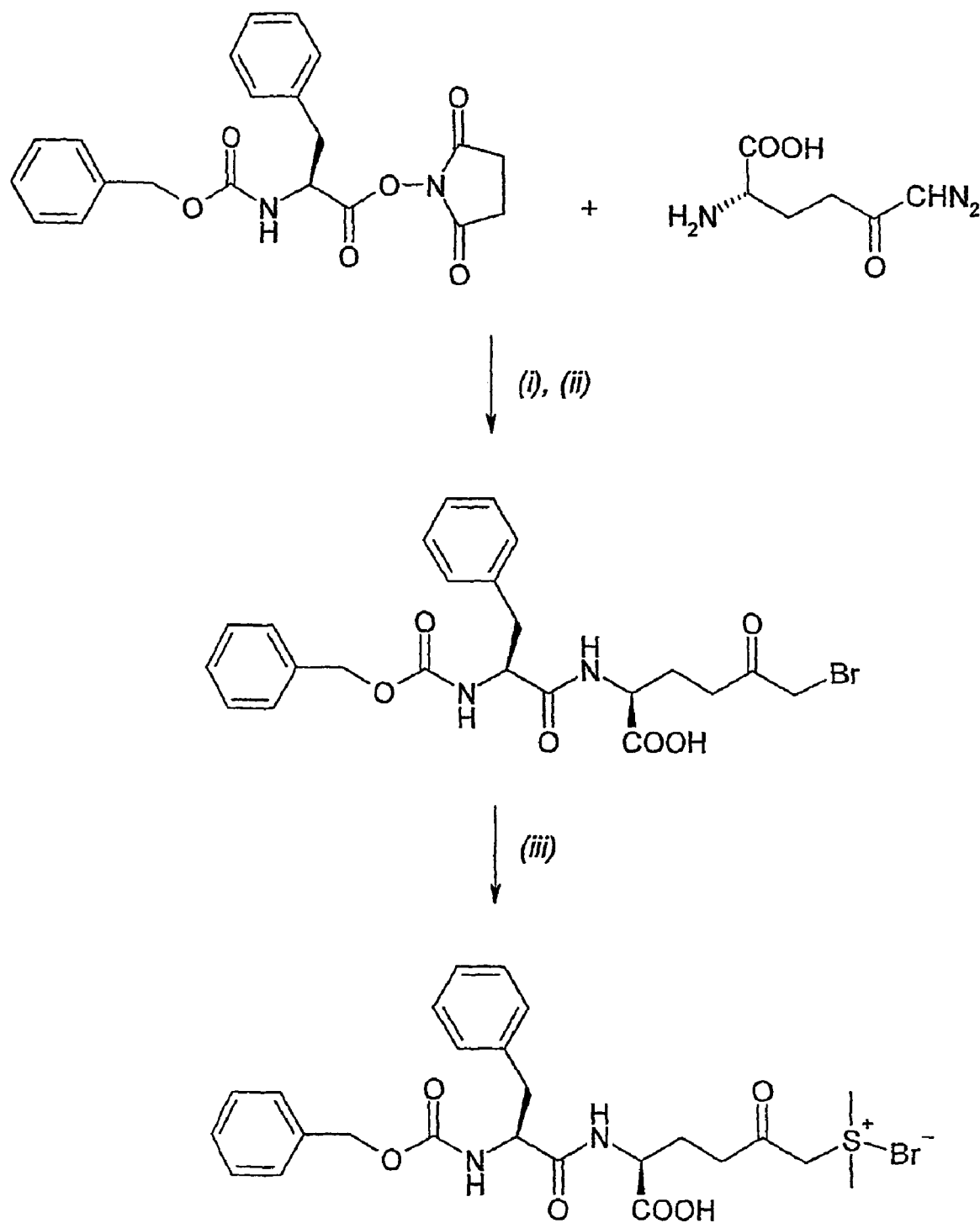
FIG. 1 shows a synthesis route for the production of an exemplary compound according to the first aspect of the invention, namely N-Benzyloxycarbonyl-L-phenylalanyl-6-dimethylsulfonium-5-oxo-L-norleucine bromide salt ('Compound 281'). In step (i) the N-α-CBZ-protected amino acid N-hydroxysuccinimide ester is reacted with 6-diazo-5-oxo-L-norleucine (DON) to produce Z-phenylalaninyl bromomethyl ketone, which is then reacted with dimethylsulphide to produce N-benzyloxycarbonyl-L-phenylalanyl-6-dimethylsulfonium-5-oxo-L-norleucine bromide salt.
Figure 2:
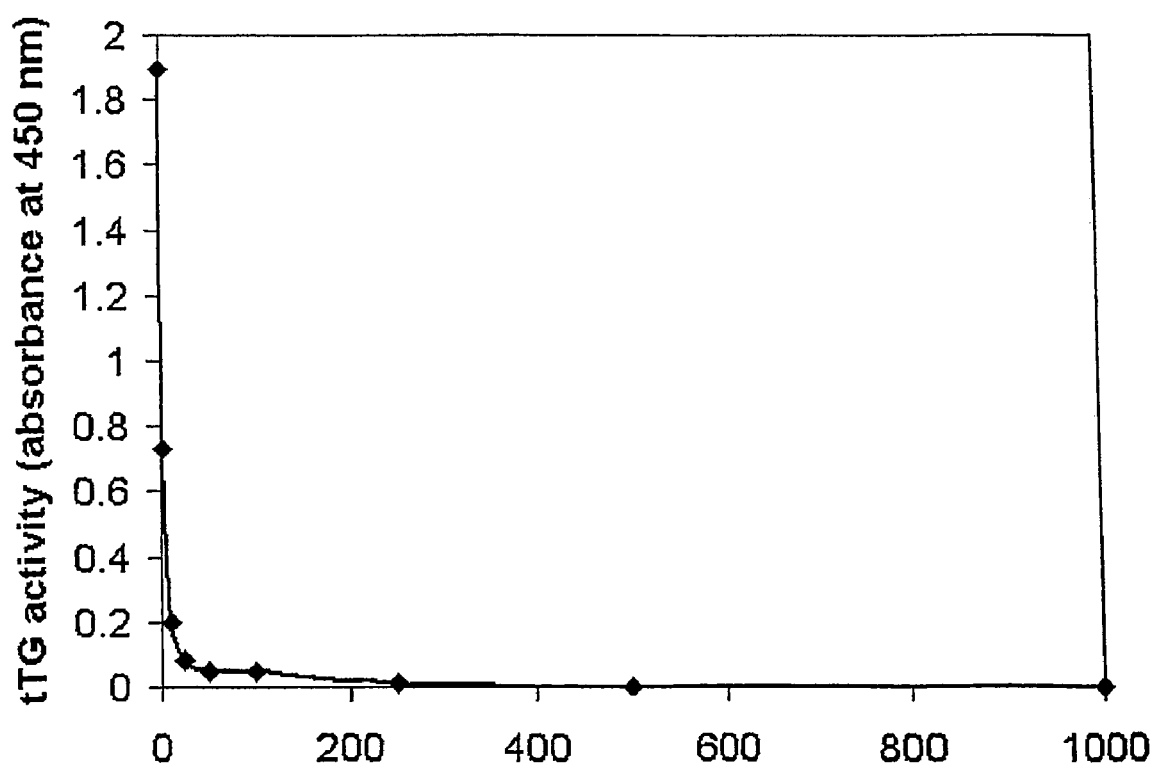
Figure 3:
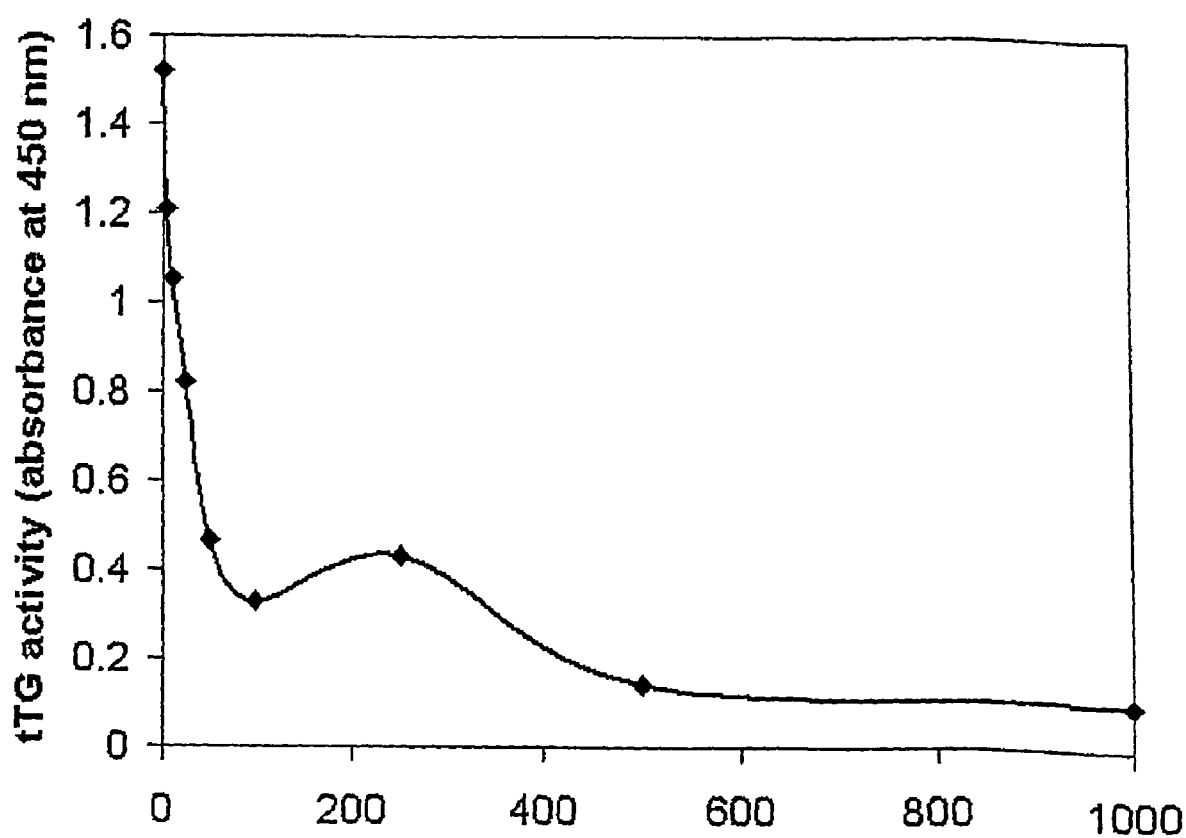
Figure 4:
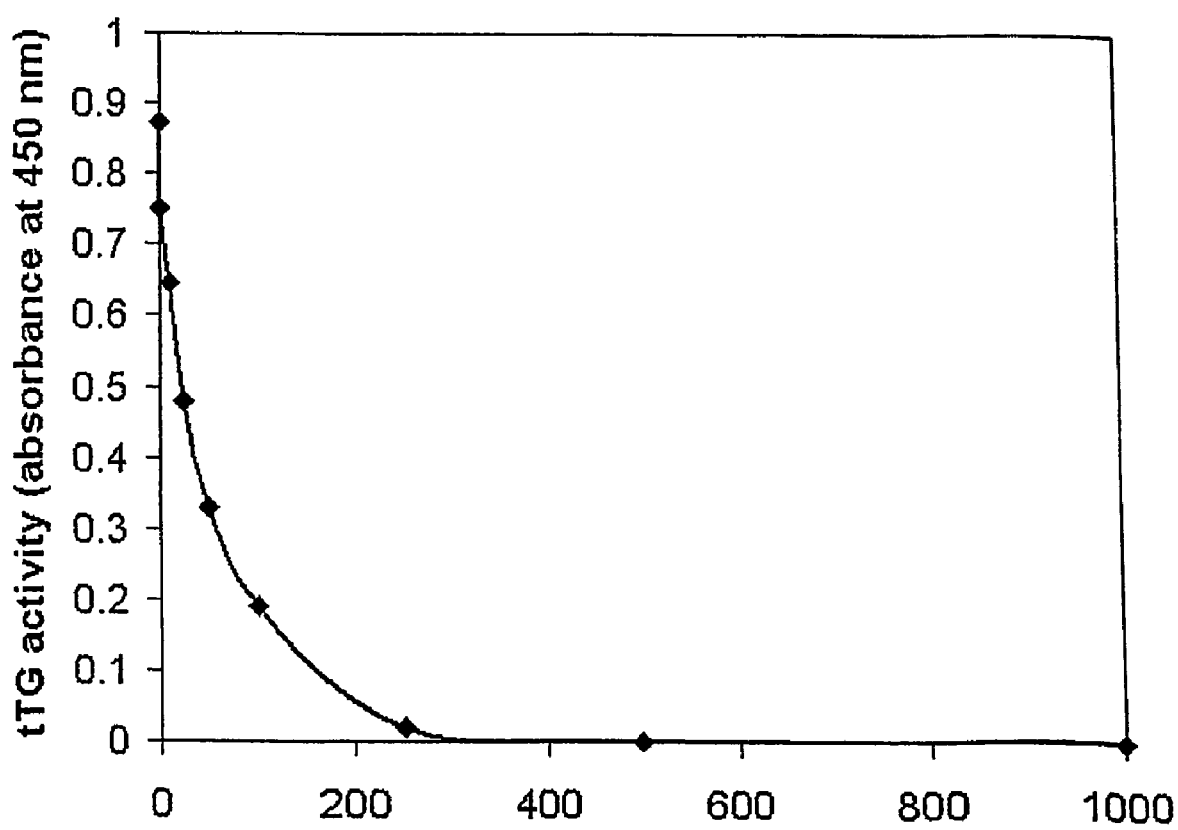
Figure 5:
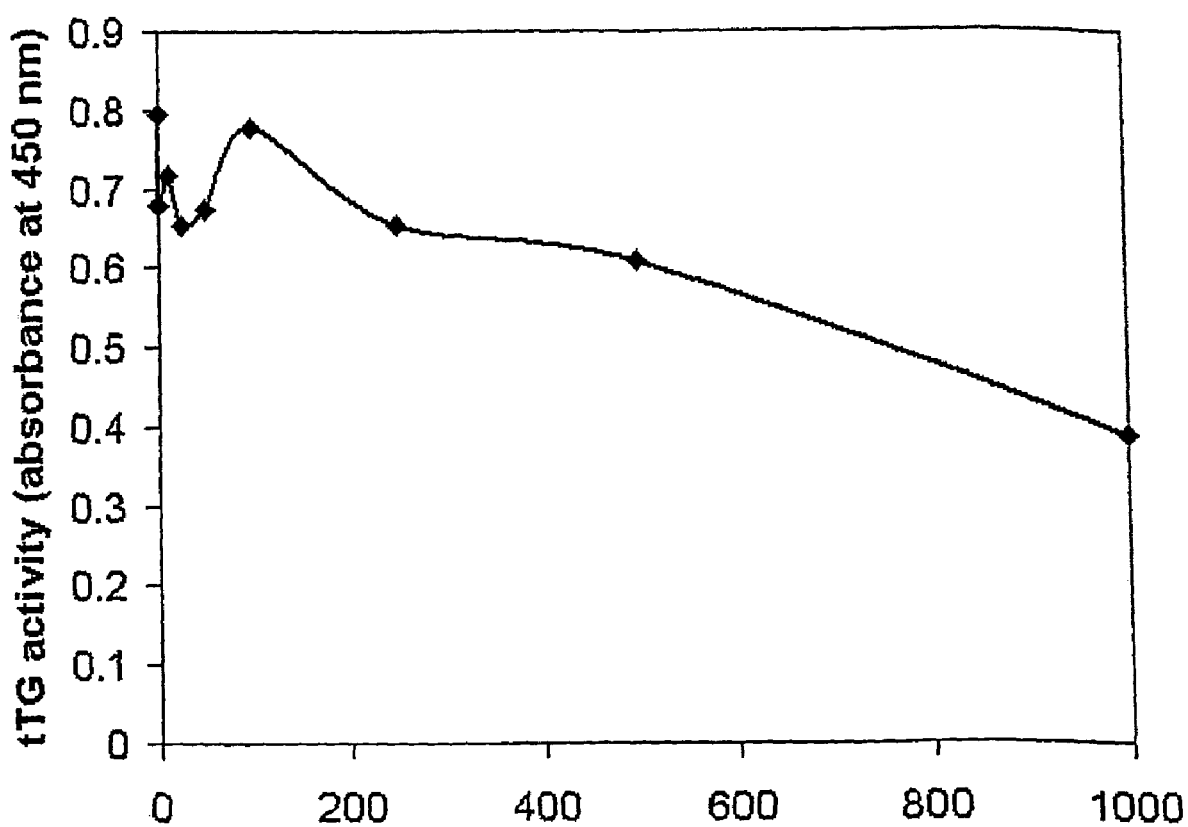
Figure 6:
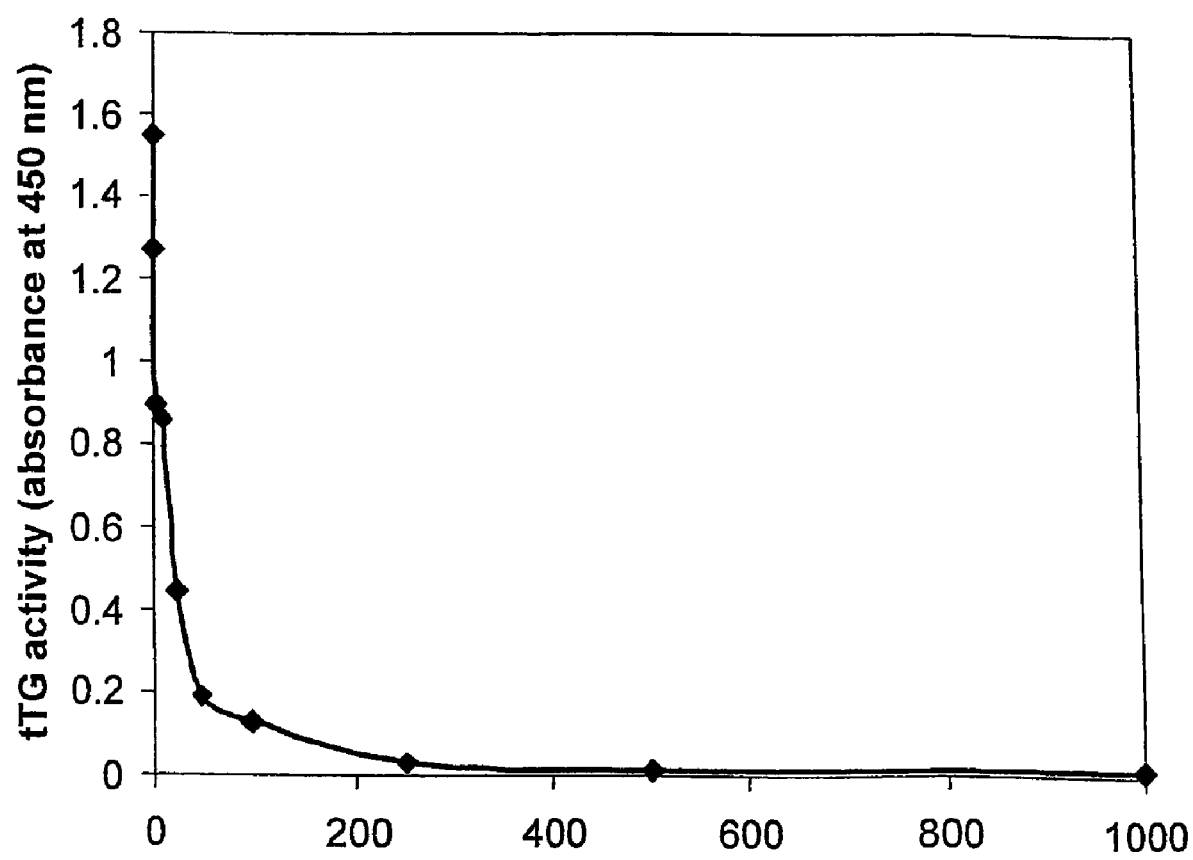
Figure 7:
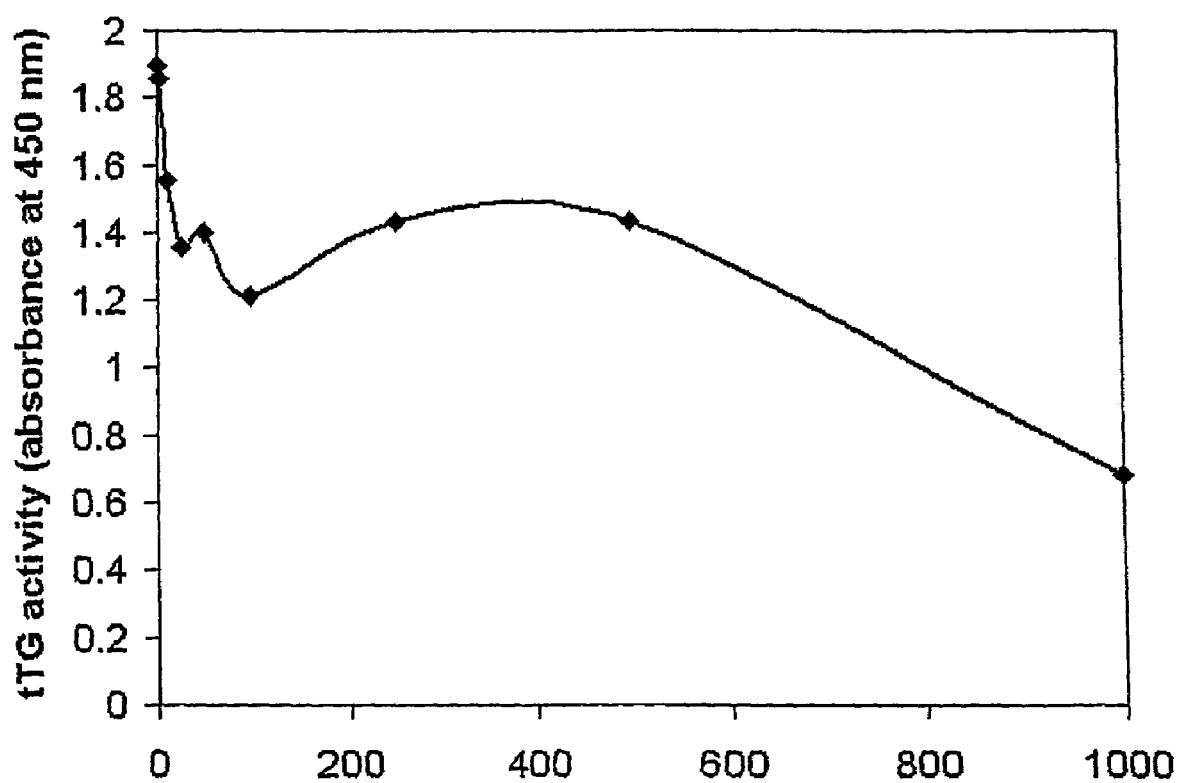
Figure 8:
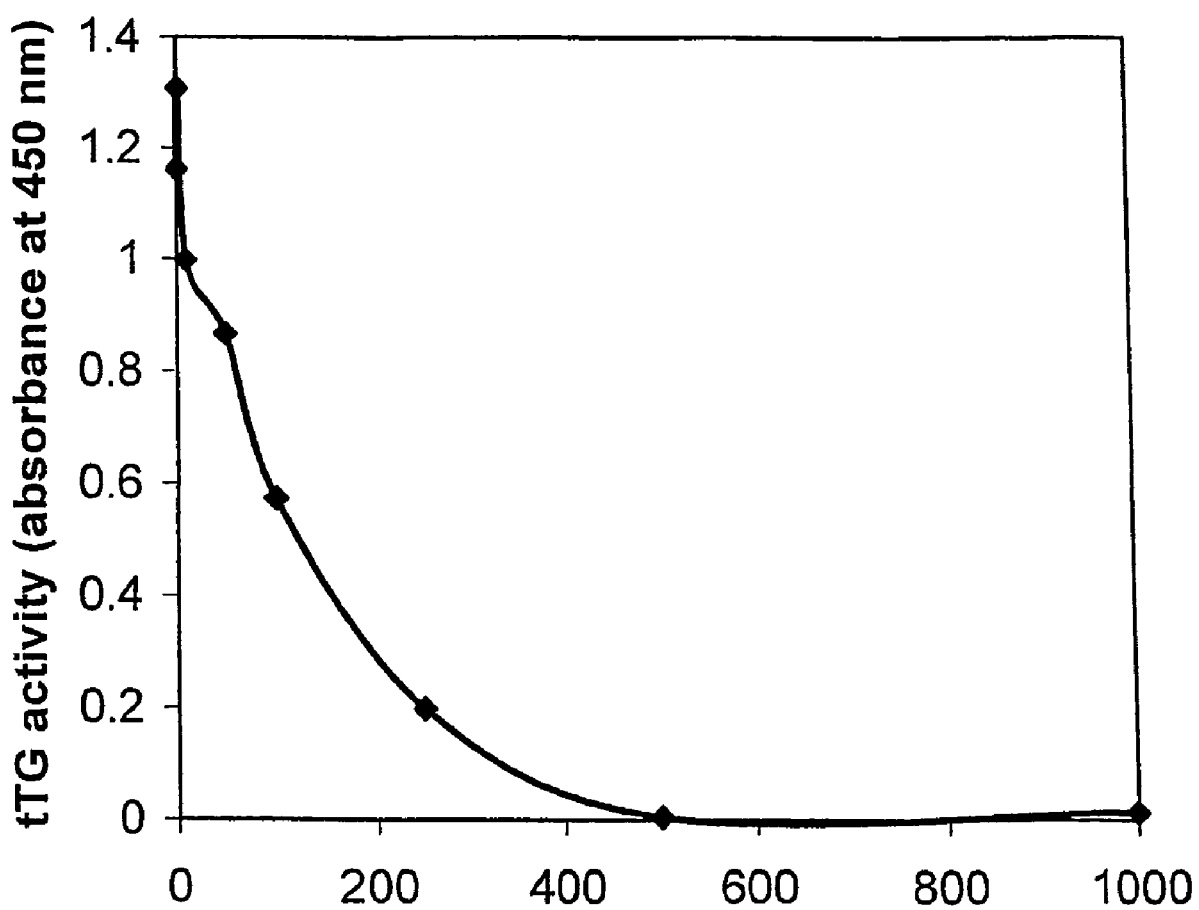
Figure 9:
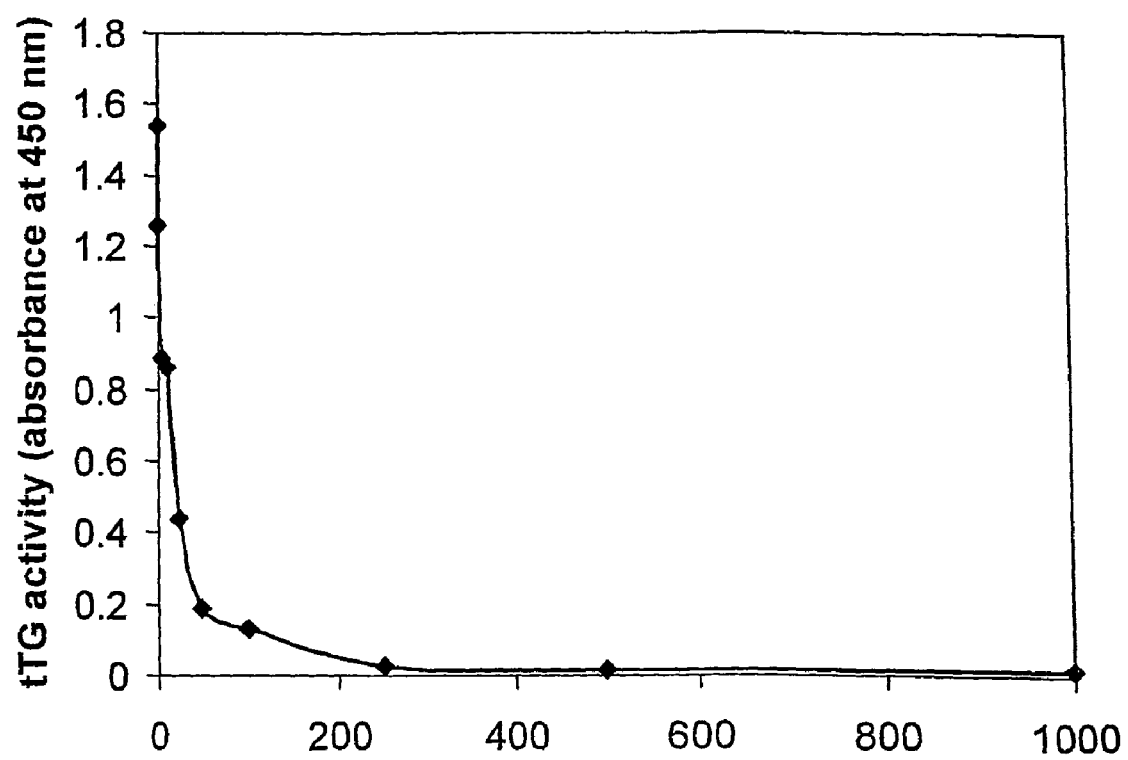
Figure 10:
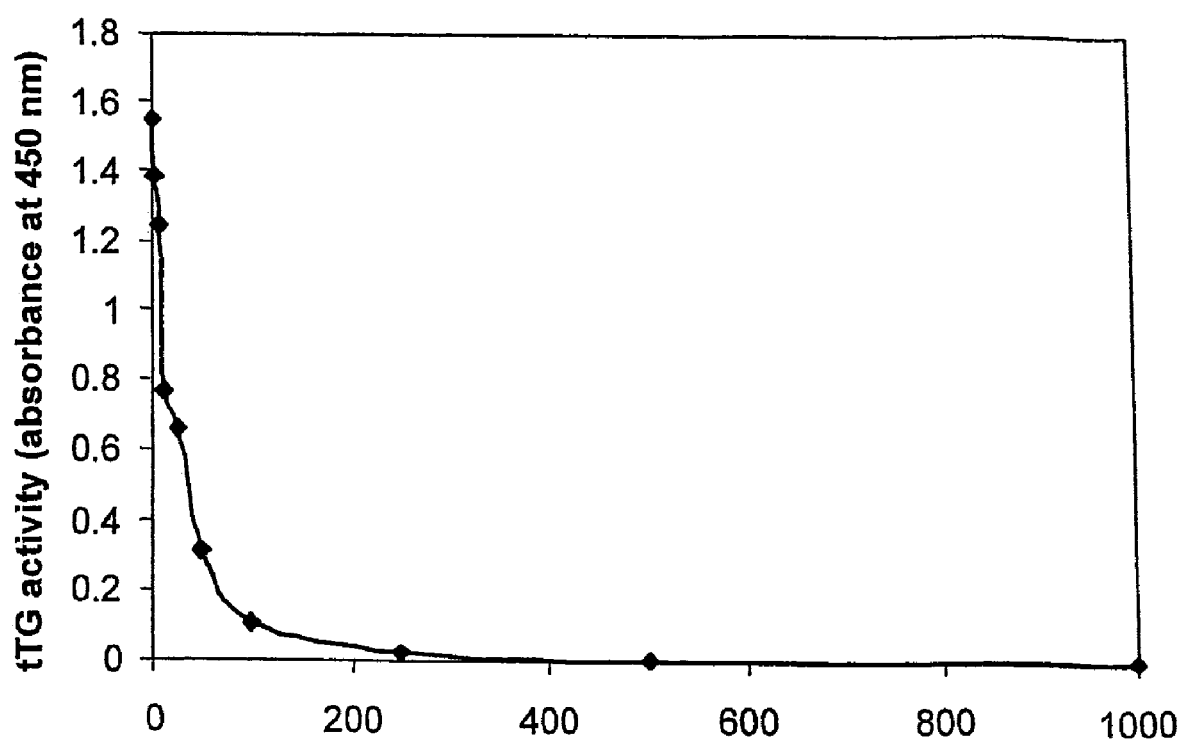
Figure 11:
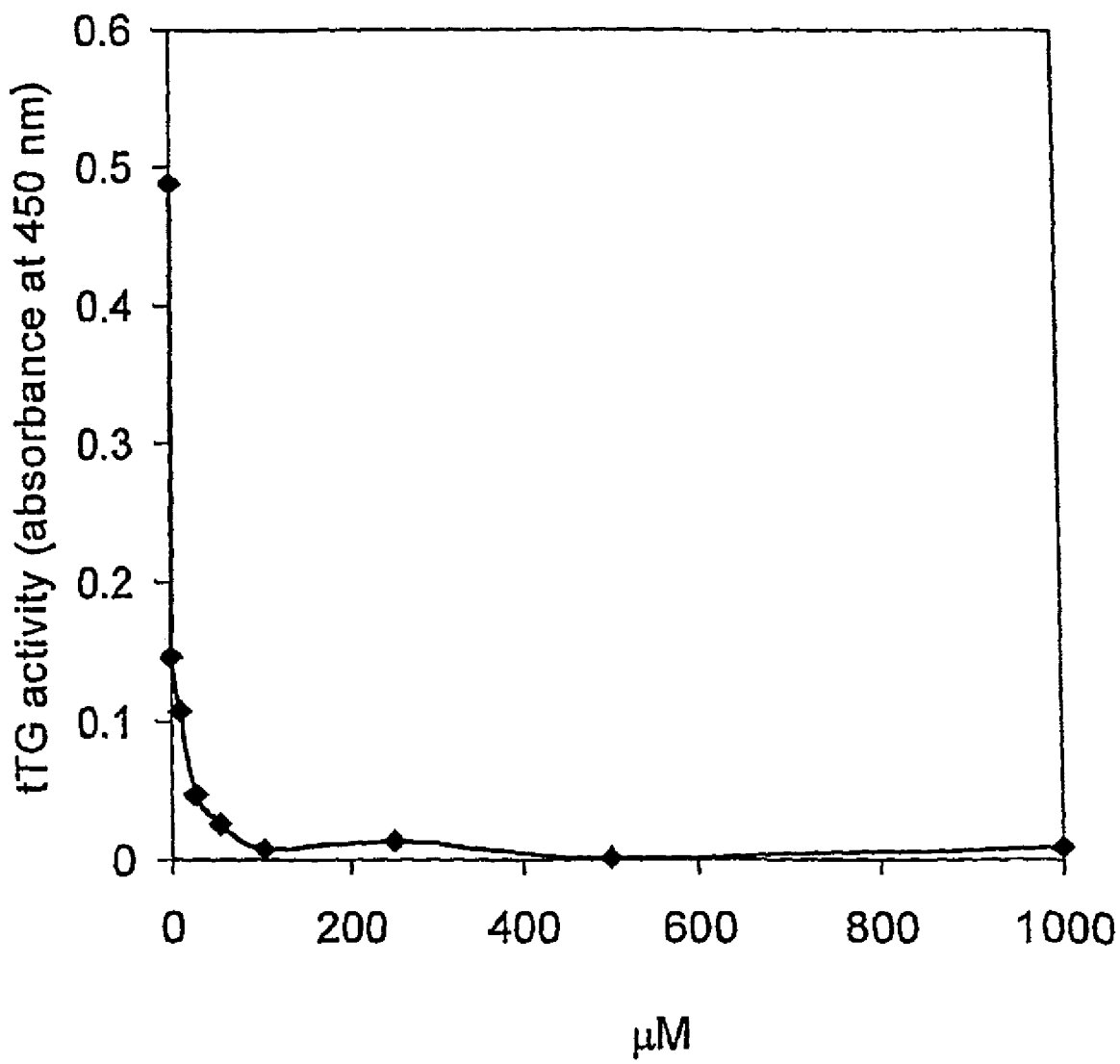
Figure 12:
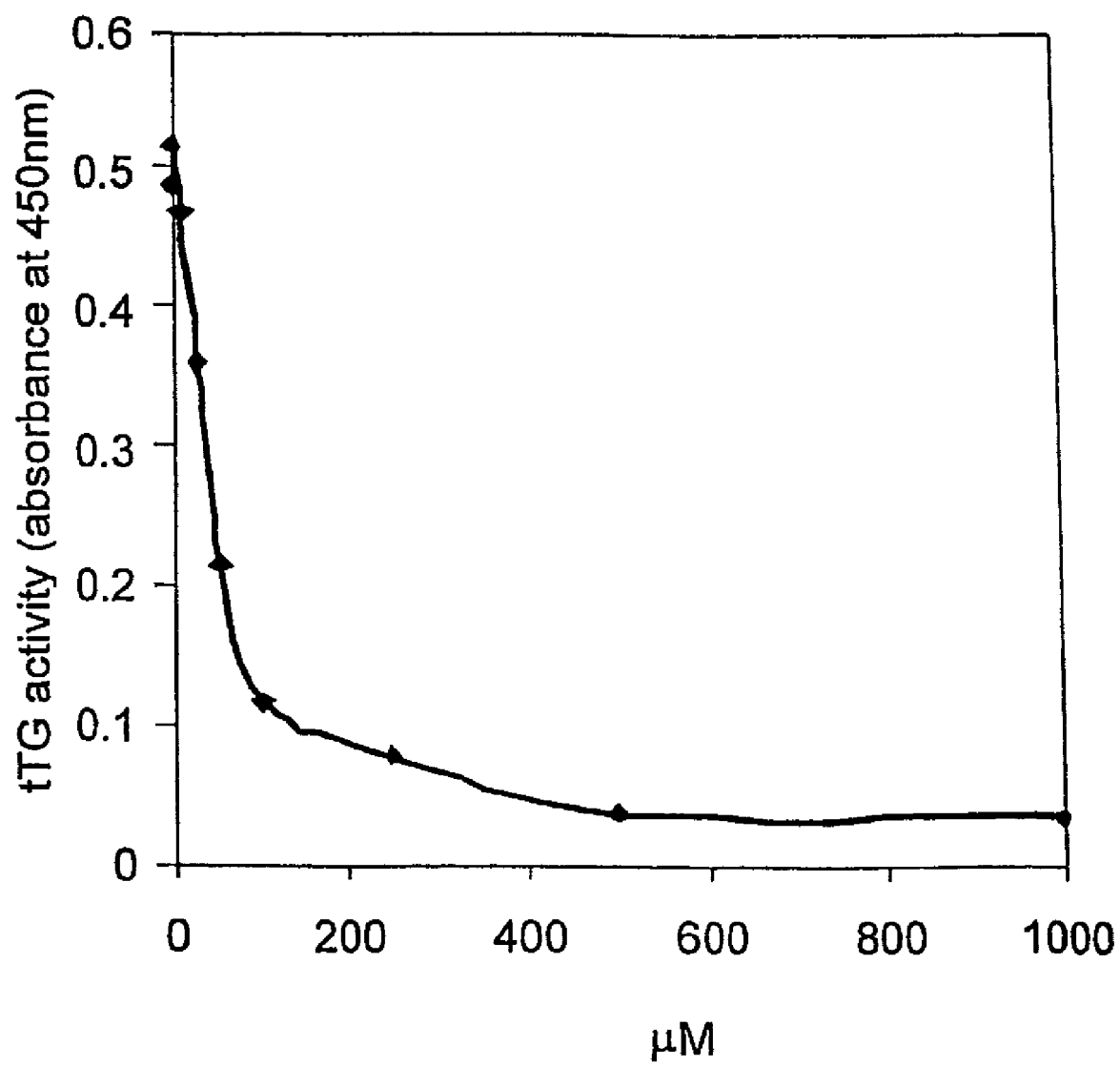
Figure 13:
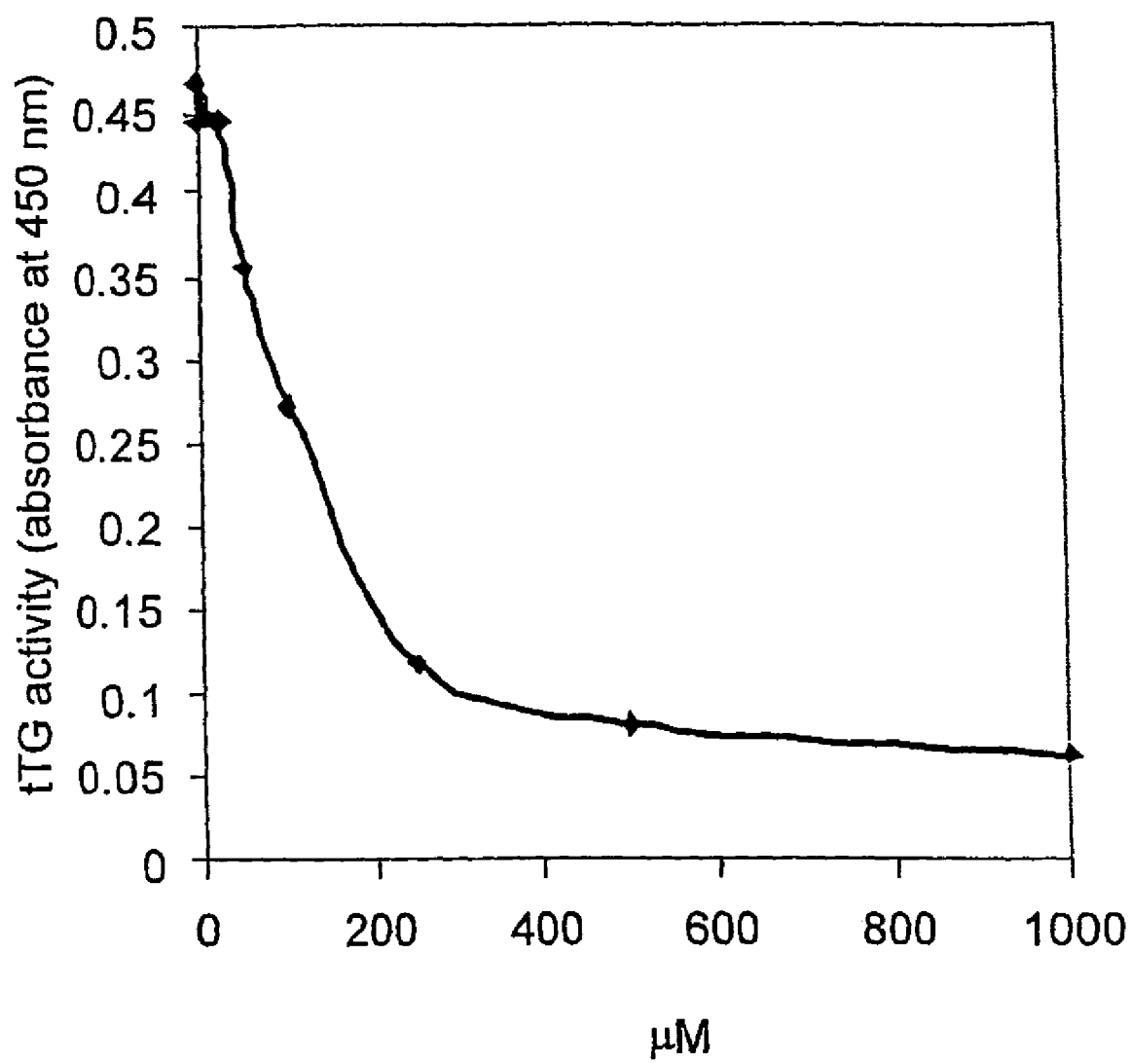
Figure 14:
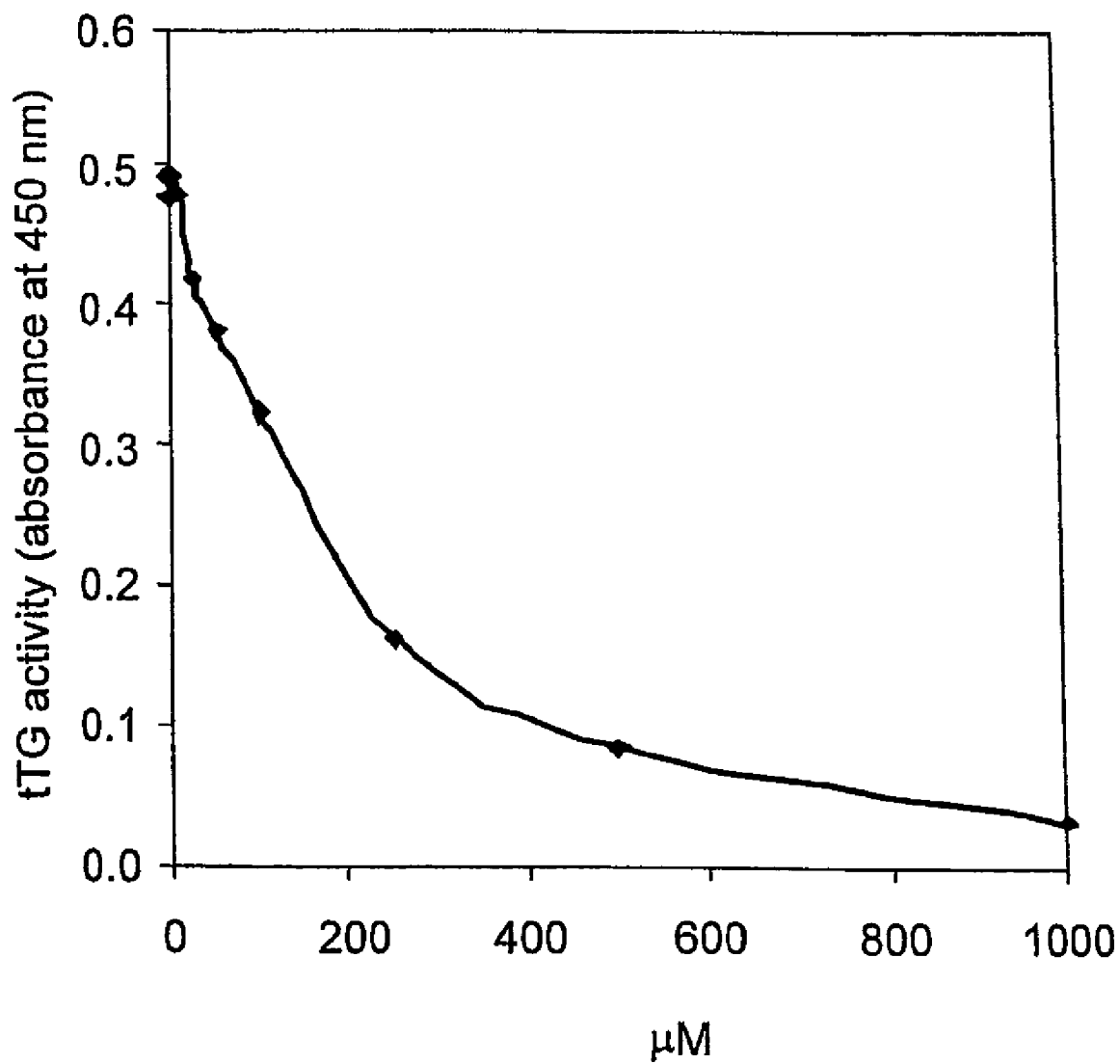
Figure 15:
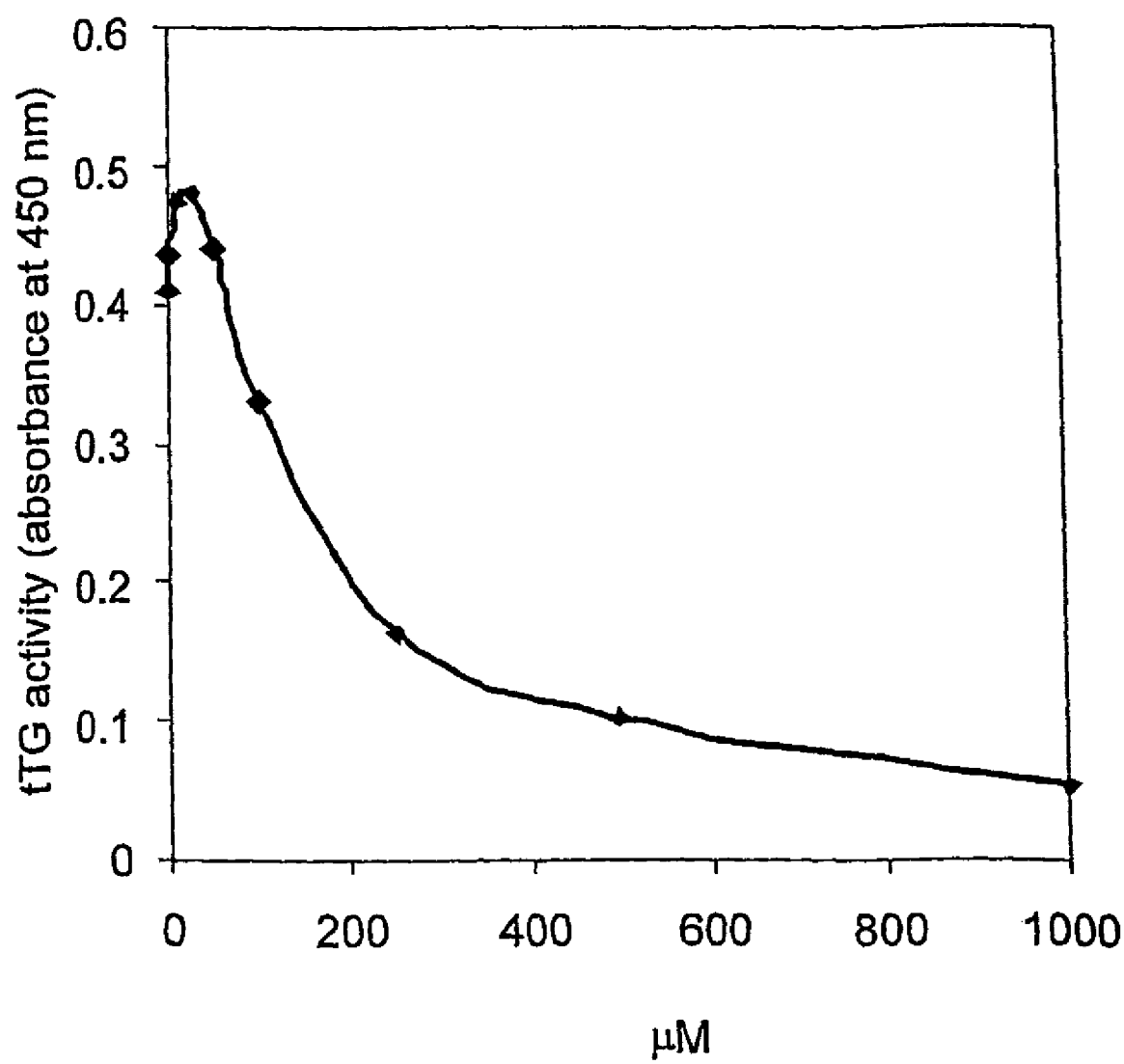
Figure 16:
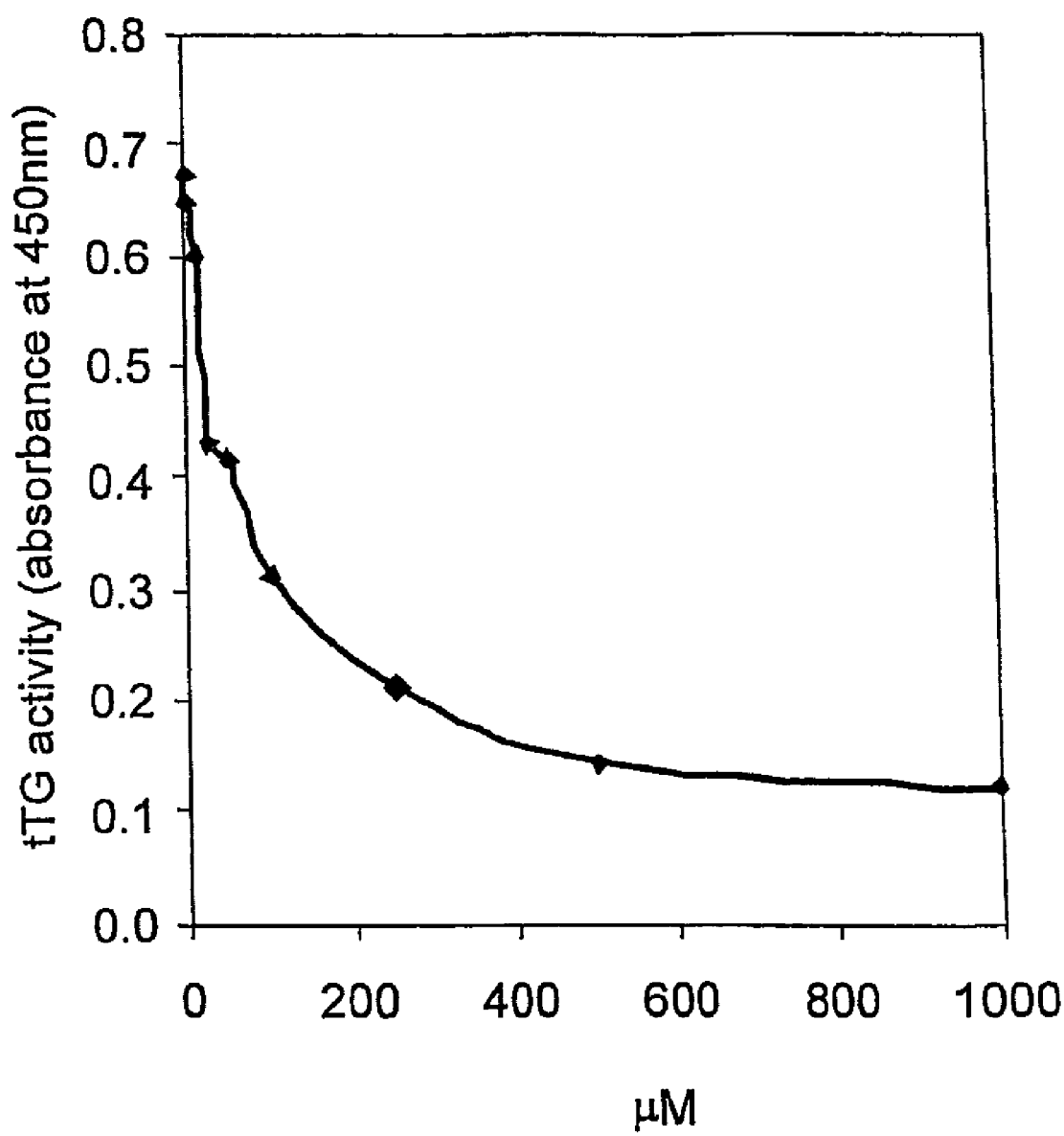
Figure 17:
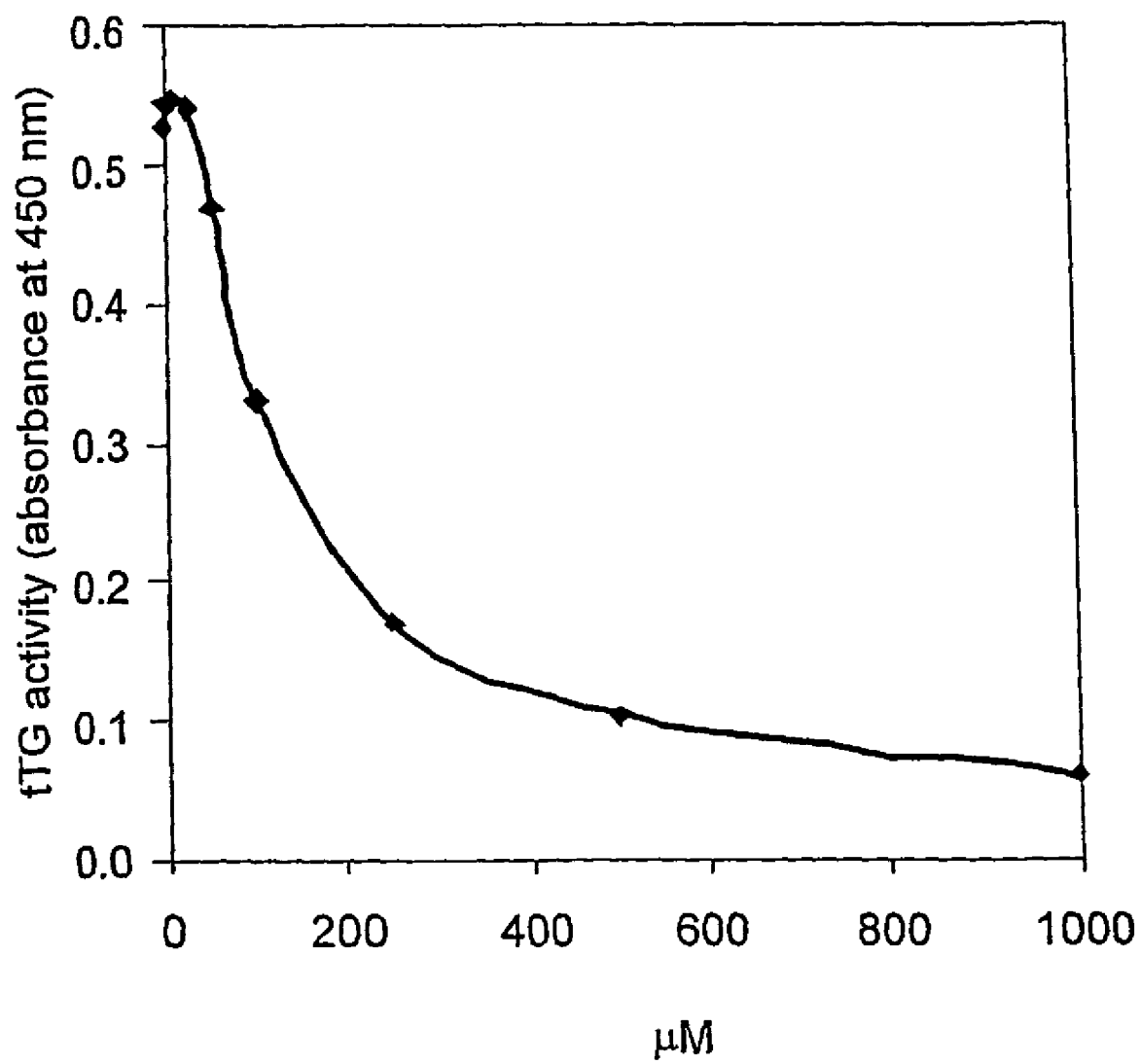
Figure 18:
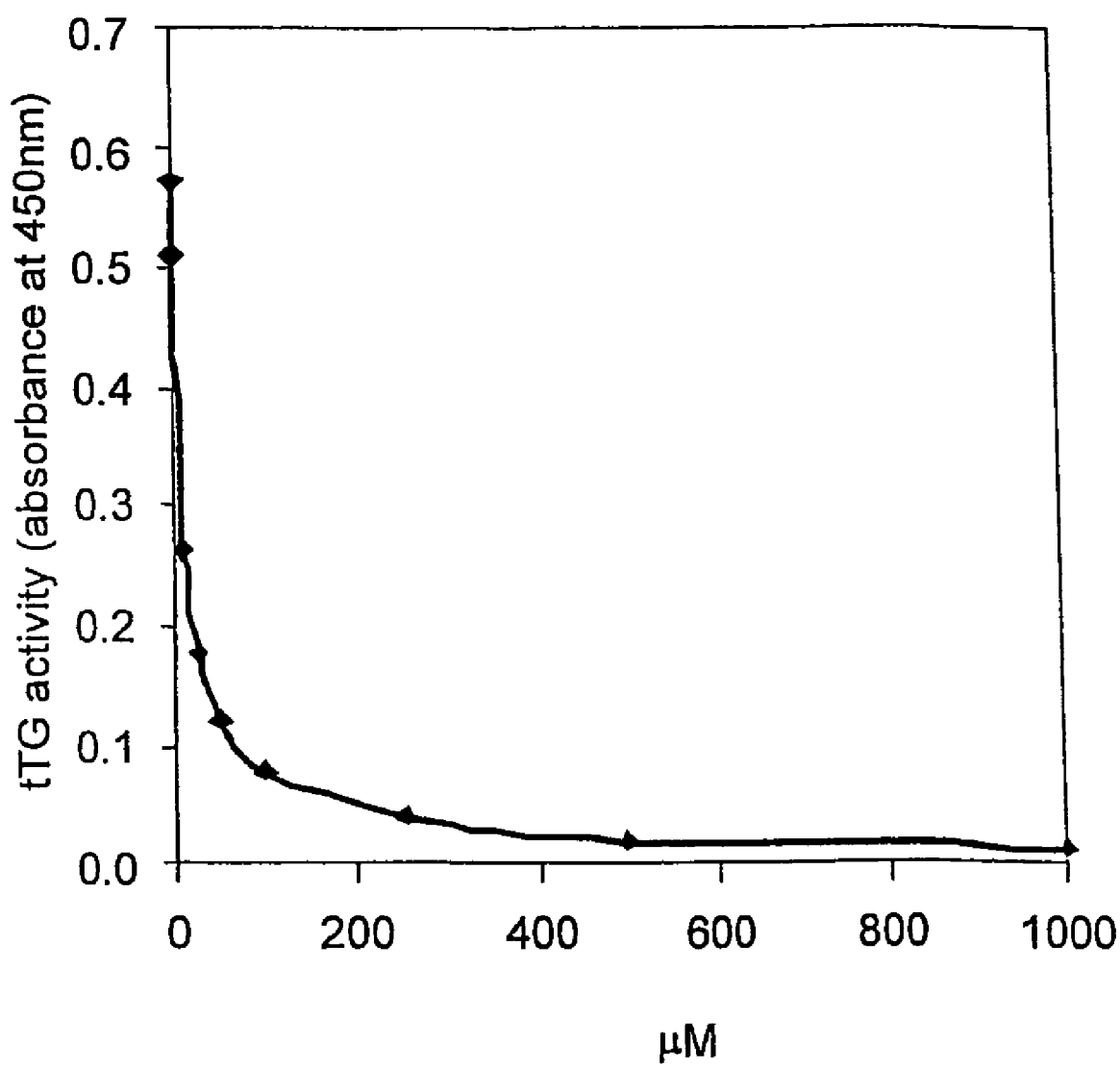
Figure 19:
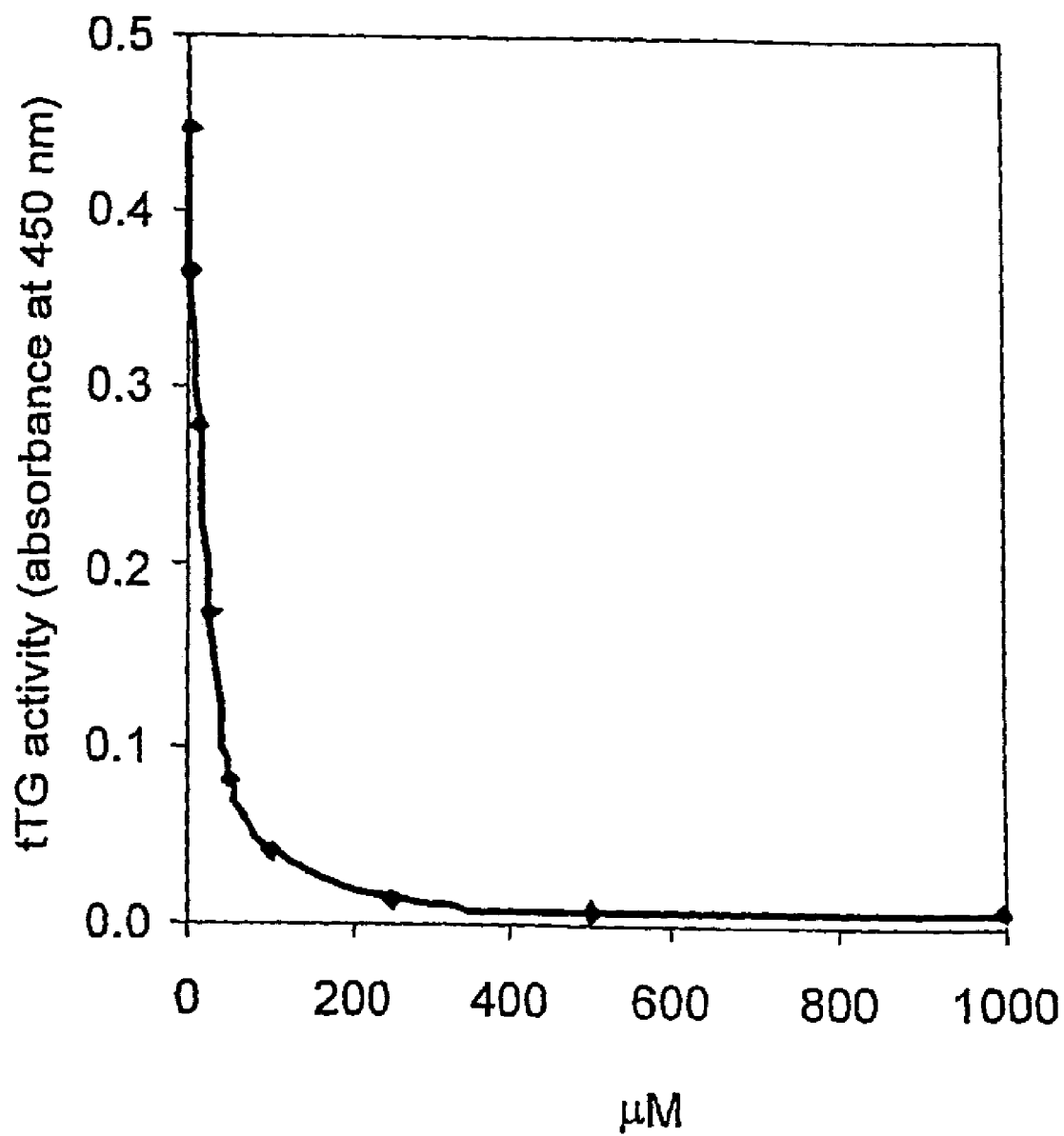
Figure 20:
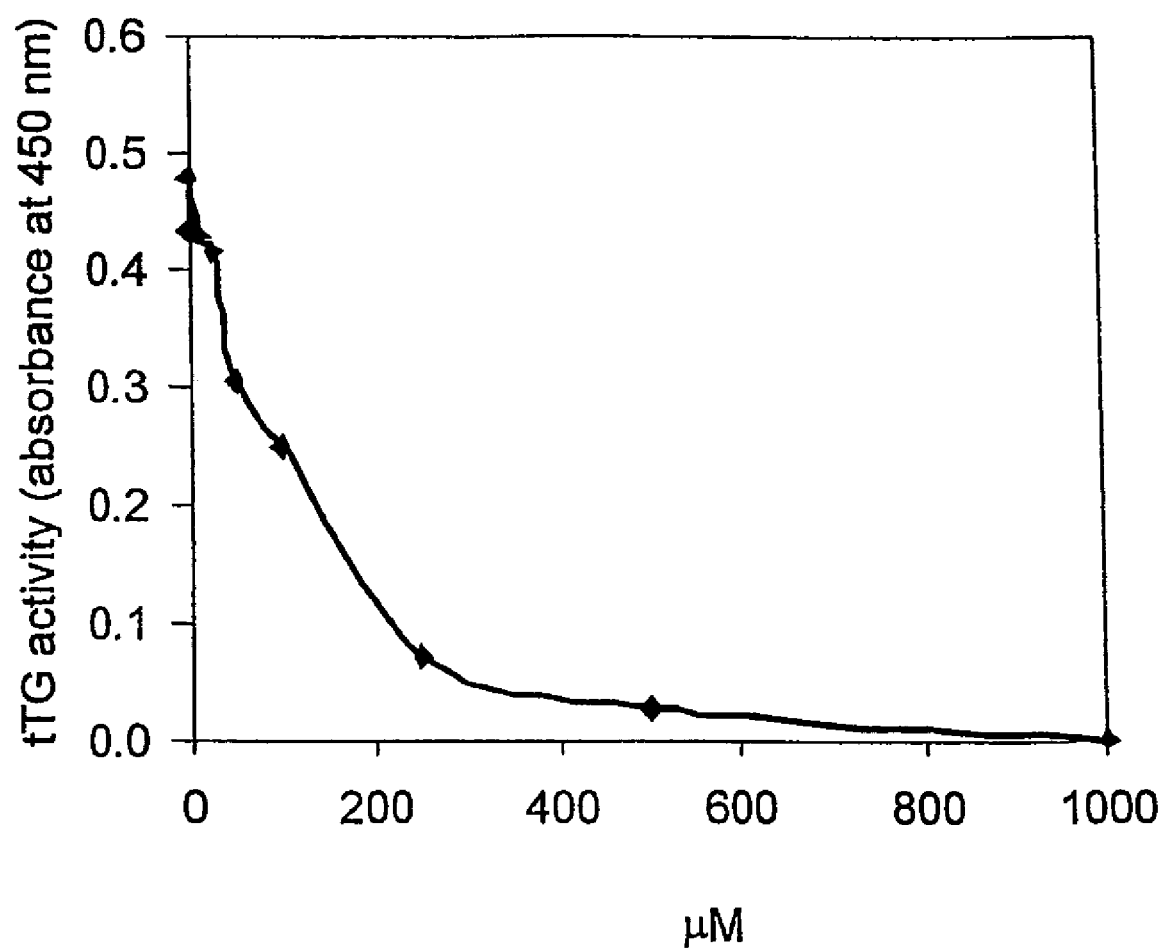
Figure 21:
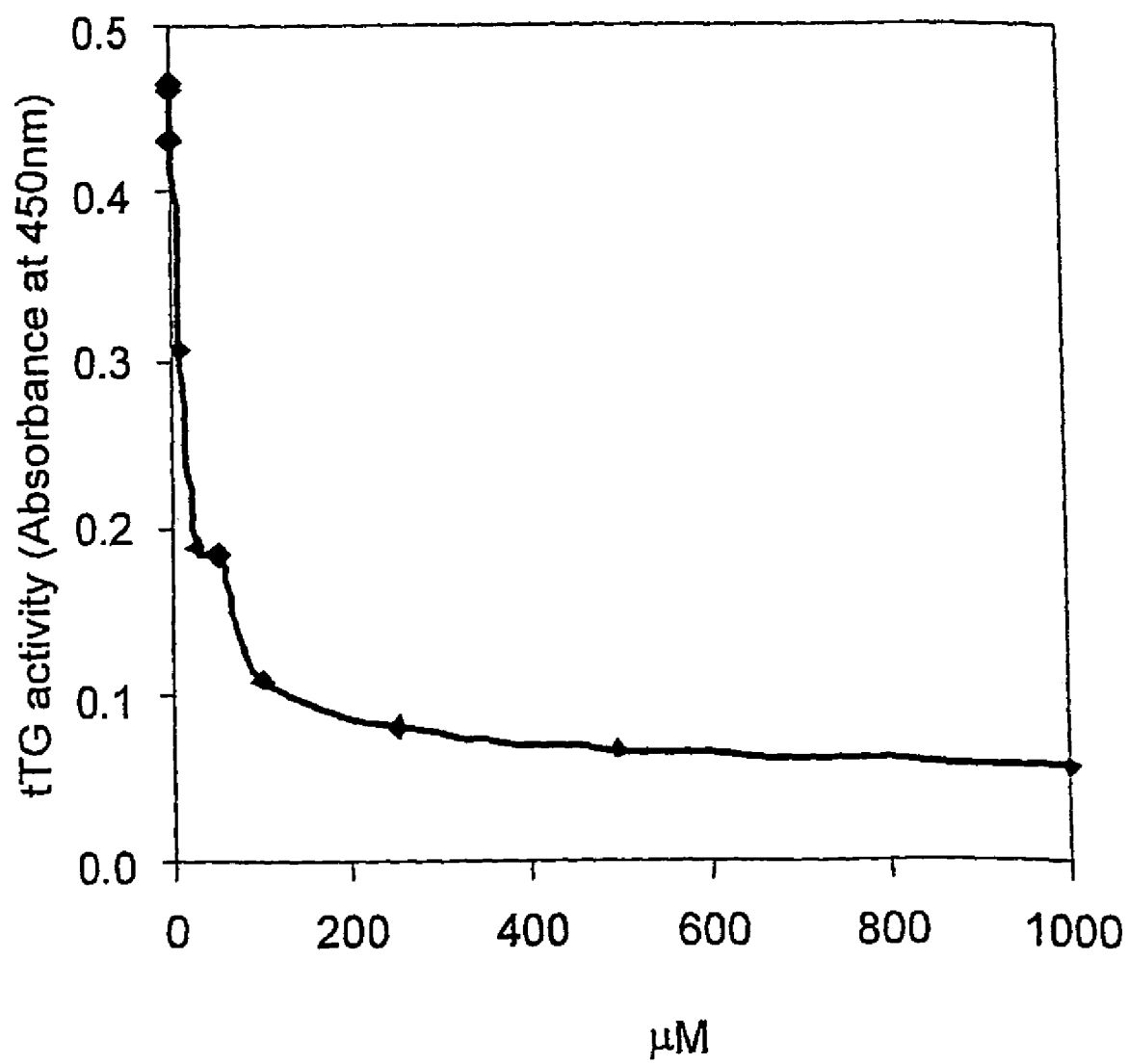

N-α-Benzyloxycarbonyl-L-phenylalanyl-6-bromo-5-oxo-L-norleucine (see '1' above) was prepared from DON and N-α-CBZ-L-phenylalanine N-hydroxysuccinimide ester (Novabiochem cat. no. 04-12-0573) (see FIG. 1)

m.p. 132-133° C. (ethyl acetate), (Found: C, 54.42; H, 5.14; N, 5.44. $C_{23}H_{25}BrN_2O_6$ requires C, 54.66; H, 4.99; N, 5.54%.); $v_{max}$ (KBr)/cm$^{-1}$ 3294, 1719, 1689, 1655; $\delta_H$ (d$_6$ acetone) 1.9, 2.2 and 2.7 (4 H, m), 2.9-3.2 (2 H, m), 4.2 (2 H, s), 4.5 (2 H, m), 5.0 (2 H, s), 6.6 (1 H, d), 7.3 (10 H, ArH), 7.6 (1 H, d); $\delta_C$ (d$_6$ acetone) 27.0, 36.0, 36.3, 38.6, 51.8, 57.2, 66.7, 127.3, 128.5, 128.6, 129.1, 129.2, 130.2, 137.9, 153.5, 172.4, 173.7, 201.0.

(b) N-α-Benzyloxycarbonyl-L-glutaminyl-6-bromo-5-oxo-L-norleucine

N-α-Benzyloxycarbonyl-L-glutaminyl-6-bromo-5-oxo-L-norleucine (see '2' above) was prepared from DON and N-α-CBZ-L-glutamine N-hydroxysuccinimide ester (Bachem cat no. C-1625)

m.p. 161-163° C. (iso-propanol, dec.), $v_{max}$ (KBr)/cm$^{-1}$ 3423, 3346, 1702, 1684, 1638; $\delta_H$ (d$_4$ methanol) 1.8, 1.9, 2.2 and 2.6 (8 H, m), 3.9 (2 H, s), 4.1 (1 H, m), 4.3 (1 H, m), 5.0 (2 H, s), 7.3 (5 H, ArH), 7.6 (1 H, d); $\delta_C$ (d$_3$ methanol) 26.8, 28.9, 32.5, 35.6, 36.5, 52.6, 55.9, 67.7, 128.8, 129.0, 129.5, 130.2, 136.9, 154.5, 171.9, 174.5, 202.6. MS: m/z Calcd for $C_{19}H_{24}BrN_3O_7$: 485 (M–Br=406). Observed 406.

(c) N-α-Benzyloxycarbonyl-L-isoleucinyl-6-bromo-5-oxo-L-norleucine

N-α-Benzyloxycarbonyl-L-isoleucinyl-6-bromo-5-oxo-L-norleucine (see '3' above) was prepared from DON and N-α-CBZ-L-isoleucine N-hydroxysuccinimide ester (Novabiochem cat. No. 04-12-0560)

m.p. 182-184° C. (ethyl acetate, dec.), $v_{max}$ (KBr)/cm$^{-1}$ 3296, 1720, 1684, 1660; $\delta_H$ (d$_3$ methanol) 0.9, 1.2 and 1.5 (6 H, m), 1.9, 2.2 and 2.7 (4 H, m), 3.9 (1 H d), 4.0 (2 H, s), 4.4 (2 H, m), 5.1 (2 H, s), 7.3 (5 H, ArH); $\delta_C$ (d$_3$ methanol) 11.2, 15.9, 25.9, 26.8, 35.6, 36.4, 37.9, 52.3, 61.1, 67.6, 128.7, 129.0, 129.5, 138.1, 154.6, 174.4, 174.5, 202.8. MS: m/z Calcd for $C_{20}H_{27}BrN_2O_6$: 470 (M–Br=391). Observed 473, 471, 391.

(d) N-α-Benzyloxycarbonyl-L-alaninyl-6-bromo-5-oxo-L-norleucine

N-α-Benzyloxycarbonyl-L-alaninyl-6-bromo-5-oxo-L-norleucine (see '4' above) was prepared from DON and N-α-CBZ-L-alamine N-hydroxysuccinimide ester (Novabiochem cat. No. 04-12-0512)

m.p. 82-85° C. (DCM/ether, dec.), $v_{max}$ (KBr)/cm$^{-1}$ 3294, 1719, 1686, 1660; $\delta_H$ (d$_6$ acetone) 1.4 (3 H, d), 1.9, 2.2 and 2.6 (4 H, m), 4.1, (2 H s), 4.2 (2 H, m), 4.4 (1 H, m), 5.1 (2 H, s), 7.3 (5 H, ArH); $\delta_C$ (d$_6$ acetone) 26.3, 28.9, 34.5, 51.3, 51.9, 66.7, 68.6, 128.7, 129.0, 129.5, 138.1, 154.6, 173.2, 174.4, 202.6. MS: m/z Calcd for $C_{17}H_{21}BrN_2O_6$: 428 (M–Br=349). Observed 429, 349.

(e) N-α-Benzyloxycarbonyl-L-glycinyl-6-bromo-5-oxo-L-norleucine

N-α-Benzyloxycarbonyl-L-glycinyl-6-bromo-5-oxo-L-norleucine (see '5' above) was prepared from DON and N-α-CBZ-L-glycine N-hydroxysuccinimide ester (Novabiochem cat. No. 04-12-0511) and used without further purification.

(f) N-α-Benzyloxycarbonyl-L-tyrosinyl-6-bromo-5-oxo-L-norleucine

N-α-Benzyloxycarbonyl-L-tyrosinyl-6-bromo-5-oxo-L-norleucine (see '6' above) was prepared from DON and N-α-CBZ-L-tyrosine 4-nitrophenyl ester (Fluka cat. No. 97300) and used without further purification.

(g) N-α-Benzyloxycarbonyl-L-prolinyl-6-bromo-5-oxo-L-norleucine

N-α-Benzyloxycarbonyl-L-prolinyl-6-bromo-5-oxo-L-norleucine (see '7' above) was prepared from DON and N-α-CBZ-L-proline N-hydroxysuccinimide ester (Novabiochem cat. no. 04-12-0577).

m.p. 129-131° C., $v_{max}$ (KBr)/cm$^{-1}$ 3241, 1725, 1690, 1664; $\delta_H$ (d$_3$ methanol) 1.9, 2.2, 2.5 and 2.8 (8 H, m), 3.5 (2 H, m), 4.0 (2 H, s), 4.3 (1 H, m), 4.5 (1 H, m), 5.0 (2 H, s), 7.3 (5 H, ArH); $\delta_C$ (d$_3$ methanol) 21.0, 23.2, 27.6, 31.7, 32.6, 48.6, 57.9, 64.4, 124.9, 125.1, 125.4, 125.9, 134.3, 153.0, 170.9, 171.5, 199.2 MS: m/z Calcd for $C_{19}H_{23}BrN_2O_6$: 455 (M+Na=477, M+H=457). Observed 477, 457.

(h) N-α-Benzyloxycarbonyl-L-serinyl-6-bromo-5-oxo-norleucine

N-α-Benzyloxycarbonyl-L-serinyl-(O-t-butyl)-6-bromo-5-oxo-L-norleucine (see '8' above) was prepared from DON and N-α-CBZ-L-serine (O-t-butyl) N-hydroxysuccinimide ester (Novabiochem cat. no. 04-12-0585).

$v_{max}$ (film)/cm$^{-1}$ 3240, 1719, 1664; $\delta_H$ (CDCl$_3$) 1.1 (9 H, s), 1.9, 2.3, and 2.7 (4 H, m), 3.4 (2 H, m), 3.9 (2 H, s), 4.3 (1 H, m), 4.6 (1 H, m), 5.1 (2 H, s), 7.3 (5 H, ArH); $\delta_C$ (CDCl$_3$) 26.4, 27.2, 34.2, 35.5, 51.4, 53.4, 61.5, 67.2, 74.3, 128.2, 128.5, 135.7, 156.3, 171.1, 175.4, 201.0 MS: m/z Calcd for $C_{21}H_{29}BrN_2O_7$: 501 (M+Na=523, 525). Observed 523, 525.

N-α-Benzyloxycarbonyl-L-serinyl-6-bromo-5-oxo-L-norleucine (see '9' above) was prepared via removal of the t-butyl protecting group using trifluoroacetic acid and triethylsilane as reagents, Mehta et al. (1992) *Tetrahedron Lett.*, 33, 5441. The crude product obtained was used without further purification.

$v_{max}$ (film)/cm$^{-1}$ 3409, 3242, 1720, 1668; $\delta_H$ (d$_3$ methanol) 1.9, 2.3, and 2.7 (4 H, m), 3.4 (2 H, m), 4.0 (2 H, s), 4.2 (1 H, m), 4.5 (1 H, m), 5.1 (2 H, s), 7.3 (5 H, ArH); $\delta_C$ (d$_3$ methanol) 26.4, 35.6, 36.4, 52.6, 57.7, 61.5, 67.8, 128.8, 129.0, 129.1, 129.4, 129.5, 138.1, 158.5, 173.0, 173.8, 202.9

(i) N-α-Benzyloxycarbonyl-L-glutaminyl-6-bromo-5-oxo-L-norleucine

N-α-Benzyloxycarbonyl-L-glutaminyl-(O-t-butyl)-6-bromo-5-oxo-L-norleucine (see '10' above) was prepared from DON and N-α-CBZ-L-glutamic acid (O-t-butyl) N-hydroxysuccinimide ester (Novabiochem cat. no. 04-12-0551).

$v_{max}$ (film)/cm$^{-1}$ 3240, 1722, 1714, 1700, 1664; $\delta_H$ (CDCl$_3$) 1.3 (9 H, s), 1.9, 2.3, and 2.7 (8 H, m), 3.8 (2 H, m), 3.9 (2 H, s), 4.2 (1 H, m), 4.5 (1 H, m), 5.0 (2 H, s), 7.3 (5 H, ArH); $\delta_C$ (CDCl$_3$) 25.8, 27.9, 31.5, 34.4, 35.5, 51.4, 54.2, 61.5, 67.1, 81.3, 127.9, 128.0, 128.1, 128.5, 136.0, 156.4, 172.3, 173.0, 174.3, 201.3 MS: m/z Calcd for $C_{23}H_{31}BrN_2O_8$: 543 (M+Na=565, 567). Observed 565, 567.

N-α-Benzyloxycarbonyl-L-glutaminyl-6-bromo-5-oxo-L-norleucine trifluoroacetic acid salt (see '11' above) was prepared via removal of the t-butyl protecting group using trifluoroacetic acid and triethylsilane as reagents, Mehta et al. (1992) *Tetrahedron Lett.*, 33, 5441. The crude product obtained was used without further purification.

$v_{max}$ (film)/cm$^{-1}$ 3404, 3242, 1720, 1700, 1680; $\delta_H$ (d$_3$ methanol) 1.9, 2.2, 2.3, 2.4, and 2.7 (8 H, m), 4.0 (2 H, s), 4.1 (1 H, m), 4.4 (1 H, m), 5.1 (2 H, s), 7.3 (5 H, ArH); $\delta_C$ (d$_3$ methanol) 26.7, 28.3, 31.1, 35.7, 36.4, 52.5, 55.7, 67.7, 128.7, 129.0, 129.5, 138.1, 158.4, 174.5, 174.6, 176.5, 202.8

(j) N-α-Benzyloxycarbonyl-L-lysinyl-6-bromo-5-oxo-L-norleucine

N-α-Benzyloxycarbonyl-L-lysinyl-(N'-BOC)-6-bromo-5-oxo-L-norleucine (see '12' above) was prepared from DON and N-α-CBZ-L-lysine (N'-BOC) N-hydroxysuccinimide ester (Novabiochem cat. no. 04-12-0526).

$\delta_H$ (CDCl$_3$) 1.4, 1.6 and 1.8 (6 H, s), 1.9, 2.1, and 2.7 (4 H, m), 2.9 (2 H, m), 3.8 (2 H, s), 4.1 (1 H, m), 4.4 (1 H, m), 5.0 (2 H, s), 7.3 (5 H, ArH); $\delta_C$ (CDCl$_3$) 17.9, 22.3, 25.7, 28.3, 31.5, 34.8, 35.6, 51.4, 53.4, 54.8, 58.1, 66.9, 79.4, 127.8, 127.9, 128.0, 128.4, 136.1, 156.5, 172.9, 174.0, 175.5, 201.5

N-α-Benzyloxycarbonyl-L-lysinyl-6-bromo-5-oxo-L-norleucine trifluoroacetic acid salt (see '13' above) was prepared via removal of the t-butyl protecting group using trifluoroacetic acid and triethylsilane as reagents, Mehta et al. (1992) *Tetrahedron Lett.*, 33, 5441. The crude product obtained was used without fiber purification.

(k) N-α-Benzyloxycarbonyl-γ-piperidinyl-L-glutaminyl-6-bromo-5-oxo-L-norleucine

N-α-Benzyloxycarbonyl-γ-piperidinyl-L-glutamic acid (see '14' above) was prepared using the methods of Molina, T. M., et al (1993) *Tetrahedron* 49, 3801-3808, Blas, J., et al (2000) *Tetrahedron Lett.* 41, 4567-4571 and Antonjuk, D. J., et al (1984) *J. Chem. Perkin Trans.* 1 1989-2003.

$v_{max}$ (film)/cm$^{-1}$ 3312, 2940, 1722, 1715, 1698, 1664; $\delta_H$ (CDCl$_3$) 1.5 (6 H, m), 2.0, 2.2, 2.4 and 2.6 (4 H, m), 3.3 (2 H, m), 3.5 (2 H, m), 4.3 (1 H, q), 5.1 (2 H, s), 6.0 (1 H, d), 7.3 (5 H, ArH); $\delta_C$ (CDCl$_3$) 24.1, 25.3, 26.2, 28.3, 29.5, 43.2, 46.8, 53.5, 66.7, 127.8, 127.9, 128.4, 136.2, 156.1, 171.5, 174.0.

N-α-Benzyloxycarbonyl-γ-piperidinyl-glutaminyl-6-bromo-5-oxo-L-norleucine (see '15' above) was prepared from DON and N-α-Benzyloxycarbonyl-γ-piperidinyl-L-glutamic acid using N-hydroxysuccinimide ester activation.

$v_{max}$ (film)/cm$^{-1}$ 3325, 2938, 1719, 1689, 1664; $\delta_H$ (d$_6$ DMSO) 1.4 and 1.5 (6 H, m), 1.8, 2.0, 2.3 and 2.6 (8 H, m), 3.3 (2 H, m), 3.4 (2 H, m), 4.0 (2 H, s), 4.2 (1 H, m), 4.3 (1 H, m), 5.0 (2 H, s), 7.3 (5 H, ArH); $\delta_C$ (d$_6$ DMSO) 24.1, 25.3, 26.1, 28.8, 33.8, 35.4, 36.8, 41.9, 45.7, 47.6, 54.1, 65.4, 67.5, 127.7, 127.8, 128.3, 137.0, 155.9, 169.6, 173.1, 173.3 200.9.

(l) N-α-Benzyloxycarbonyl-γ-propyl-L-glutaminyl-6-bromo-5-oxo-L-norleucine

N-α-Benzyloxycarbonyl-γ-propyl-L-glutamic acid (see '16' above) was prepared using the methods of Molina, T. M., et al (1993) *Tetrahedron* 49, 3801-3808, Blas, J., et al (2000) *Tetrahedron Lett.* 41, 4567-4571 and Antonjuk, D. J., et al (1984) *J. Chem. Perkin Trans.* 1 1989-2003.

$v_{max}$ (film)/cm$^{-1}$ 3328, 2965, 1706, 1702, 1698, 1653; $\delta_H$ (CDCl$_3$) 0.8 (3 H, t), 1.4 (2 H, m), 2.0 and 2.2 (4 H, m), 3.1 (2 H, m), 4.3 (1 H, q), 5.1 (2 H, s), 6.0 (1 H, d), 6.5 (1 H, m), 7.3 (5 H, ArH); $\delta_C$ (CDCl$_3$) 11.2, 22.4, 28.6, 32.4, 41.6, 53.4, 67.1, 127.9, 128.1, 128.2, 128.5, 136.0, 156.6, 173.4, 173.9.

N-α-Benzyloxycarbonyl-γ-propyl-glutaminyl-6-bromo-5-oxo-L-norleucine (see '17' above) was prepared from DON and N-α-Benzyloxycarbonyl-γ-propyl-L-glutamic acid using N-hydroxysuccinimide ester activation.

$v_{max}$ (film)/cm$^{-1}$ 3325, 2938, 1719, 1689, 1664; $\delta_H$ (d$_6$ DMSO) 1.4 and 1.5 (6 H, m), 1.8, 2.0, 2.3 and 2.6 (8 H, m), 3.3 (2 H, m), 3.4 (2 H, m), 4.0 (2 H, s), 4.2 (1 H, m), 4.3 (1 H, m), 5.0 (2 H, s), 7.3 (5 H, ArH); $\delta_C$ (d$_6$ DMSO) 11.7, 23.5, 25.2, 26.0, 28.8, 33.0, 34.7, 38.1, 52.0, 56.0, 67.7, 128.7, 128.8, 129.3, 137.0, 155.9, 169.6, 174.7, 174.8 200.8.

(m) N-α-9-Fluorenylmethyloxycarbonyl-L-phenylalanyl-6-bromo-5-oxo-L-norleucine

N-α-9-Fluorenylmethyloxycarbonyl-L-phenylalanyl-6-bromo-5-oxo-L-norleucine (see '18' above) was prepared from DON and N-α-FMOC-L-phenylalanine N-hydroxysuccinimide ester (Bachem cat. no. B-1415).

m.p. 142-143° C., $v_{max}$ (KBr)/cm$^{-1}$ 3354, 1714, 1700, 1686; $\delta_H$ (d$_6$ DMSO) 1.9, 2.2 and 2.7 (4 H, m), 2.9-3.1 (2 H, m), 4.2-4.4 (5 H, m), 7.3 (9 H, ArH), 7.6 (2 H, ArH), 7.8 (2 H, ArH); $\delta_C$ (d$_6$ DMSO) 25.5, 35.5, 36.6, 37.4, 46.6, 50.9, 56.1, 64.4, 120.0, 124.8, 125.1, 127.2, 127.5, 127.6, 128.7, 129.3, 137.0, 140.7, 143.7, 155.9, 171.9, 173.1, 200.7

(n) N-α-tert-butyloxycarbonyl-L-phenylalanyl-6-bromo-5-oxo-L-norleucine

N-α-tert-butyloxycarbonyl-L-phenylalanyl-6-bromo-5-oxo-L-norleucine (see '19' above) was prepared from DON and N-α-BOC-L-phenylalanine N-hydroxysuccinimide ester (Novabiochem cat. no. 04-12-0074).

$v_{max}$ (film)/cm$^{-1}$ 3380, 2930, 1722, 1699, 1684; $\delta_H$ (d$_3$ methanol) 1.2 (9 H, s), 1.8, 2.1 and 2.6 (4 H, m), 2.7-3.0 (2 H, m), 4.0 (2 H, s), 4.2 (1 H, m), 4.3 (2 H, m), 4.8 (2 H, s), 7.1 (5 H, ArH); $\delta_C$ (d$_3$ methanol) 27.0, 28.7, 35.6, 36.4, 39.0, 52.4, 57.3, 80.6, 127.7, 129.4, 130.4, 138.2, 157.6, 174.4, 174.5, 202.7

Preparation of Amino Acid Derived TGase Inhibitors

Sulfonium salts of the above intermediates were prepared using a modification of procedures previously reported by Pliura et al. (1992) *J. Enzyme Inhibition* 6, 2768 and Shaw (1988) *Biol. Chem.,* 263, 2768.

The bromomethyl ketone was dissolved in the minimum amount of dry methanol to achieve solution. Methyl sulfide (2.5-7.5 eqv.) was added and the solution left in a tightly stoppered flask for 24-48 h. until the reaction was judged complete by TLC. Purification was achieved by dissolving the residue in deionised water and extracting the organic soluble impurities with ethyl acetate. Freeze drying the aqueous portion afforded the product salts as colourless solids in typically 80-90% yields.

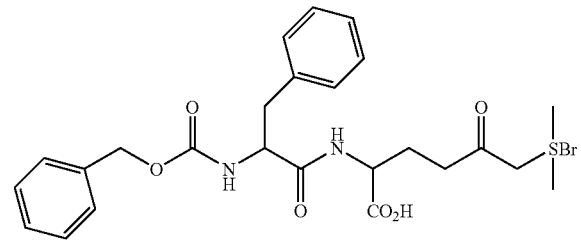

281

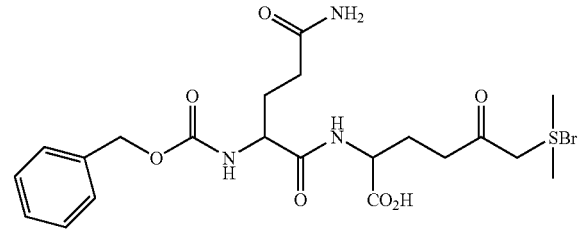

285

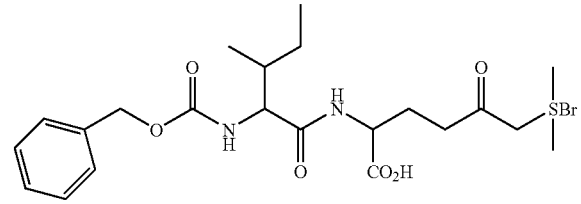

286

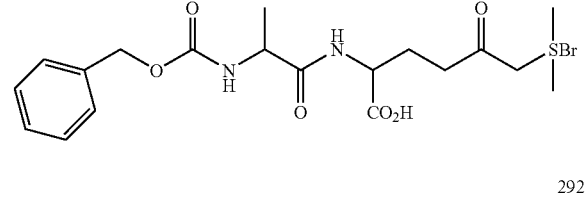

291

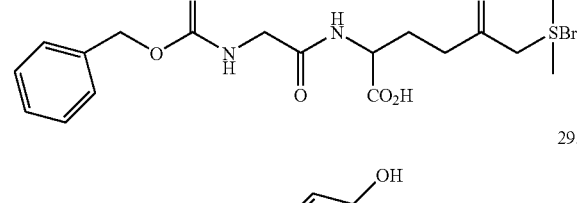

292

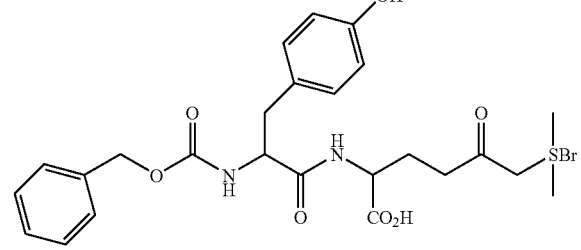

293

-continued
294
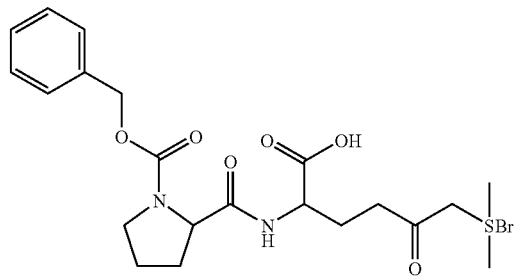
295
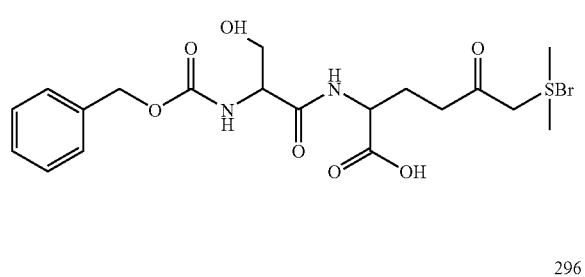
296
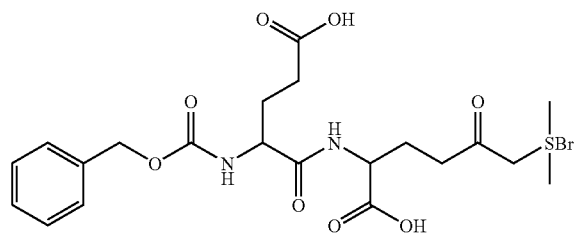
297
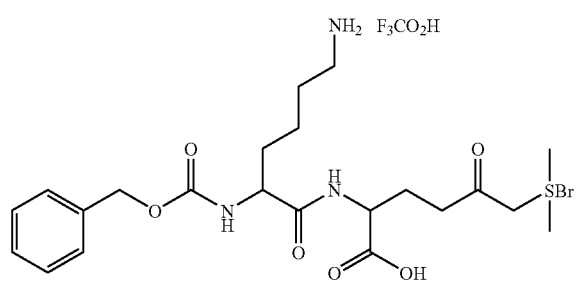
298
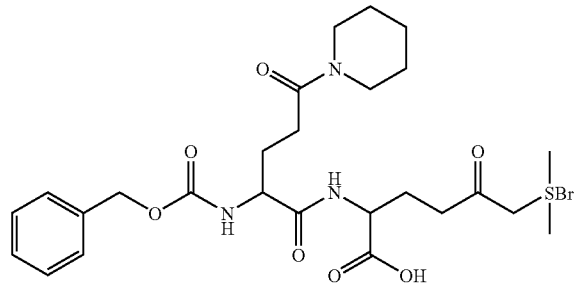
-continued
299
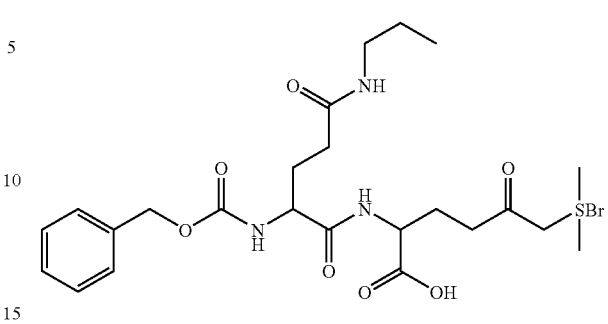
300
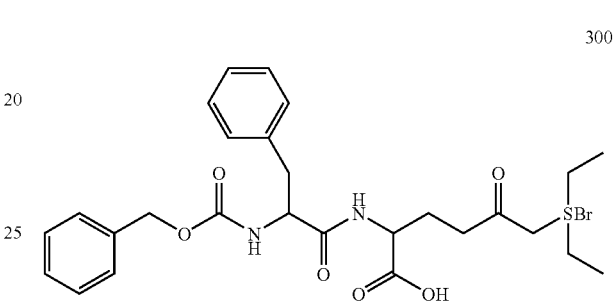
301
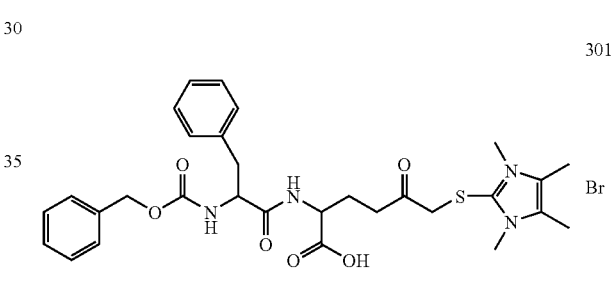
302
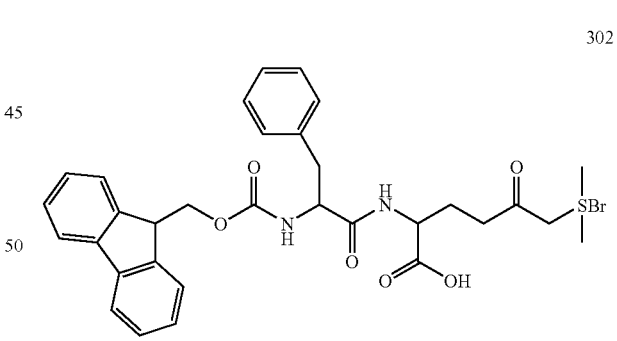
303
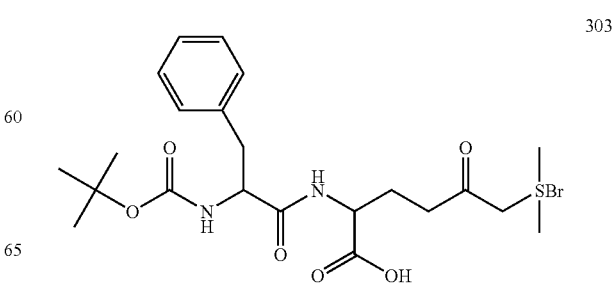

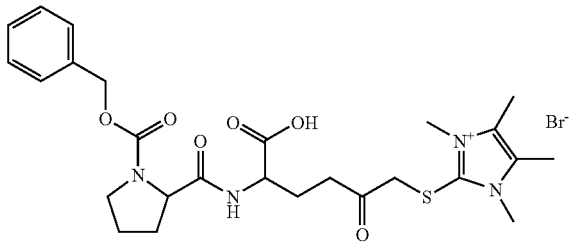

304

(a) N-Benzyloxycarbonyl-L-phenylalanyl-6-dimethylsulfonium-5-oxo-L-norleucine Bromide Salt (See '281' Above)

m.p. 90-92° C., (Found: C, 52.89; H, 4.89; N, 5.05. $C_{25}H_{31}BrN_2O_6S$ requires C, 52.91; H, 5.51; N, 4.94%.); $\nu_{max}$ (KBr)/cm$^{-1}$ 3296, 1715, 1700, 1661; $\delta_H$ (d$_6$ acetone) 1.9, 2.2 and 2.7 (4 H, m), 2.9-3.1 (2 H, m), 3.2 (6 H, s), 4.6 (2 H, m), 5.0 (2 H, s), 5.4 (1 H, d), 7.3 (10 H, ArH), 7.4 (1 H, d); $\delta_C$ (d$_6$ acetone) 25.2, 36.1, 38.5, 41.8, 51.9, 56.3, 60.6, 66.3, 128.4, 128.6, 129.0, 129.2, 130.3, 138.2, 138.6, 153.3, 168.7, 173.2, 202.0.

(b) N-Denzyloxycarbonyl-L-glutaminyl-6-dimethylsulfonium-5-oxo-L-norleucine Bromide Salt (See '285' Above)

m.p. 100° C. (dec.), $\nu_{max}$ (KBr)/cm$^{-1}$ 3423, 3346, 1702, 1684, 1638; $\delta_H$ (DMSO-D$_6$) 1.7, 1.9, 2.1 and 2.6 (8 H, m), 2.8 (6 H, s), 3.3 (1 H, br), 3.9 (2 H, s), 4.2 (1 H, m), 4.7 (2 H, m), 5.0 (2 H, s), 6.7 (1 H, s), 7.3 (5 H, ArH), 7.4 (1 H, d), 8.2 (1 H, d); $\delta_C$ (DMSO-D$_6$) 24.5, 25.2, 27.7, 31.5, 37.5, 50.6, 53.5, 54.3, 65.4, 127.6, 127.8, 128.3, 128.4, 136.9, 155.9, 172.0, 172.9, 173.8, 201.4. MS: m/z Calcd for $C_{21}H_{30}N_3O_7S$: 547.09878 (M−Br=468.18045). Observed 468.17769.

(c) N-Benzyloxycarbonyl-L-isoleucinyl-6-dimethylsulfonium-5-oxo-L-norleucine Bromide Salt (See '286' Above)

m.p. 111-114° C. (dec.), $\nu_{max}$ (KBr)/cm$^{-1}$ 3424, 1717, 1700, 1664; $\delta_H$ (DMSO-D$_6$) 0.9, 1.2 and 1.5 (6 H, m), 1.9, 2.2 and 2.7 (4 H, m), 3.2 (6 H, s), 3.9 (1 H d), 4.1 (2 H, s), 4.4 (1 H, m), 5.1 (2 H, s), 7.3 (5 H, ArH); $\delta_C$ (DMSO-D$_6$) 11.2, 15.9, 25.9, 26.8, 35.6, 36.4, 37.9, 52.3, 61.1, 67.6, 128.7, 129.0, 129.5, 138.1, 154.6, 174.4, 174.5, 202.8. MS: m/z Calcd for $C_{22}H_{33}BrN_2O_6S$: 532 (M−Br=453). Observed 453.

(d) N-Benzyloxycarbonyl-L-alaninal-6-dimethylsulfonium-5-oxo-L-norleucine Bromide Salt (See '291' Above)

m.p. 100-102° C. (dec.), $\nu_{max}$ (KBr)/cm$^{-1}$ 3426, 1716, 1698, 1660; $\delta_H$ (d$_6$ DMSO) 1.2 (3 H, d), 1.8, 2.0 and 2.7 (4 H, m), 2.9 (6H, s), 4.0, (1 H, m), 4.2 (1 H, m), 4.8 (2 H, m), 5.0 (2 H, s), 7.3 (5 H, ArH); $\delta_C$ (d$_6$ DMSO) 24.5, 37.4, 49.8, 50.6, 52.0, 53.5, 65.3, 66.3, 127.7, 127.8, 128.3, 137.0, 155.7, 172.8, 172.9, 201.4. MS: m/z Calcd for $C_{19}H_{27}BrN_2O_6S$: 490 (M−Br=411). Observed 411.

(e) N-Benzyloxycarbonyl-L-glycinal-6-dimethylsulfonium-5-oxo-L-norleucine Bromide Salt (See '292' Above)

m.p. 96-99° C. (dec.), $\nu_{max}$ KBr)/cm$^{-1}$ 3424, 1714, 1701, 1663; $\delta_H$ (d$_6$ DMSO) 1.8, 2.1 and 2.6 (4 H, m), 2.9 (6H, s), 3.6, (2 H, m), 4.3 (1 H, m), 4.7 (2 H, d), 5.0 (2 H, s), 7.3 (5 H, ArH); $\delta_C$ (d$_6$ DMSO) 24.5, 37.4, 43.2, 50.6, 53.5, 65.4, 66.3, 127.6, 127.8, 128.3, 137.0, 156.5, 169.2, 172.9, 201.4. MS: m/z Calcd for $C_{18}H_{25}BrN_2O_6S$: 476 (M−Br=397). Observed 397.

(f) N-Benzyloxycarbonyl-L-tyrosinal-6-dimethylsulfonium-5-oxo-L-norleucine Bromide Salt (See '293' Above)

m.p. 111-113° C. (dec.), $\nu_{max}$ (KBr)/cm$^{-1}$ 3426, 1716, 1700, 1666; $\delta_H$ (d$_6$ DMSO) 1.9 and 2.1 (2 H, m), 2.6 (4 H, m), 2.9 (6H, s), 4.2, (2 H s), 4.7 (2 H, d), 4.9 (2 H, d), 6.7 (2H, d, ArH), 7.1 (2 H, d, ArH), 7.3 (5 H, ArH); $\delta_C$ (d$_6$ DMSO) 24.4, 24.8, 36.5, 37.5, 50.8, 53.5, 56.3, 65.2, 114.8, 127.3, 127.7, 128.0, 128.3, 130.1, 137.0, 155.7, 172.0, 172.9, 201.4. MS: m/z Calcd for $C_{25}H_{31}BrN_2O_7S$: 582 (M−Br=503). Observed 503.

(g) N-Benzyloxycarbonyl-L-prolinyl-6-dimethylsulfonium-5-oxo-L-norleucine Bromide Salt (See '294' Above)

m.p. 93-97° C. (dec.), $\nu_{max}$ (KBr)/cm$^{-1}$ 3244, 2952, 1720, 1693, 1669; $\delta_H$ (d$_3$ methanol) 1.9 (4 H, m), 2.2 (2 H, m), 2.7 (2 H, m), 2.8 (6 H, s), 3.6 (2 H, m), 4.3 (1 H, m), 4.5 (1 H, m), 4.8 (2 H, m), 5.1 (2 H, s), 7.3 (5 H, ArH); $\delta_C$ (d$_3$ methanol) 25.3, 25.4, 26.3, 28.1, 31.1, 38.2, 52.1, 55.9, 67.6, 128.6, 129.1, 129.6, 138.2, 158.5, 174.4, 174.7, 201.8. MS: m/z Calcd for $C_{21}H_{29}BrN_2O_6S$: 517 (M−Br=437). Observed 437.

(h) N-Benzyloxycarbonyl-L-serinyl-6-dimethylsulfonium-5-oxo-L-norleucine Bromide Salt (See '295' Above)

m.p. 105° C. (dec.), $\nu_{max}$ (KBr)/cm$^{-1}$ 3242, 2950, 1719, 1700, 1664; $\delta_H$ (d$_3$ methanol) 1.9 (2 H, m), 2.3 (2 H, m), 2.9 (6 H, s), 3.8 (2 H, m), 4.2 (1 H, m), 4.4 (1 H, m), 4.8 (2 H, m), 5.1 (2 H, s), 7.3 (5 H, ArH); $\delta_C$ (d$_3$ methanol) 24.6, 25.4, 26.3, 31.6, 32.5, 38.0, 48.3, 51.8, 61.6, 68.0, 128.4, 128.8, 129.1, 129.6, 138.2, 156.7, 174.3, 175.3, 201.8. MS: m/z Calcd for $C_{19}H_{27}BrN_2O_7S$: 507 (M−Br=427). Observed 427.

(i) N-Benzyloxycarbonyl-L-glutaminyl-6-dimethylsulfonium-5-oxo-L-norleucine Bromide Salt (See '296' Above)

m.p. 102-106° C. (dec.), $\nu_{max}$ (KBr)/cm$^{-1}$ 3329, 2926, 1719, 1698, 1664; $\delta_H$ (d$_3$ methanol) 1.9, 2.1, 2.4 and 2.7 (8 H, m), 2.9 (6 H, s), 4.1 (1 H, m), 4.5 (1 H, m), 4.8 (2 H, m), 5.1 (2 H, s), 7.3 (5 H, ArH); $\delta_C$ (d$_3$ methanol) 25.3, 25.4, 26.3, 28.1, 31.1, 38.2, 52.1, 55.9, 67.6, 128.6, 129.1, 129.6, 138.2, 158.5, 174.4, 174.7, 201.8. MS: m/z Calcd for $C_{21}H_{29}BrN_2O_8S$: 549 (M−Br=469). Observed 469.

(j) N-α-Benzyloxycabonyl-N-ε-trifluoroacetate-L-lysinyl-6-dimethylsulfonium-5-oxo-L-norleucine Bromide Salt (See '297' Above)

m.p. 110° C. (dec.), $\nu_{max}$ (KBr)/cm$^{-1}$ 3334, 1722, 1688; $\delta_H$ (d$_3$ methanol) 1.4 and 1.7 (6 H, m), 1.9, 2.1 and 2.7 (6 H, m), 2.9 (6 H, s), 4.1 (1 H, m), 4.4 (1 H, m), 4.8 (2 H, m), 5.1 (2 H, s), 7.3 (5 H, ArH). MS: m/z Calcd for $C_{24}H_3BrF_3N_3O_8S$: 662 (M−Br—$F_3C_2O_2H$=468). Observed 468.

(k) N-α-Benzyloxycarbonyl-γ-piperidinyl-L-glutaninyl-6-dimethylsulfonium-5-oxo-L-norleucine Bromide Salt (See '298' Above)

m.p. 92-94° C. (dec.), $\nu_{max}$ (KBr)cm$^{-1}$ 3415, 2933, 1719, 1700, 1664, 1618; $\delta_H$ (d$_3$ methanol) 1.5, 1.7 (6 H, m), 2.0, 2.3 and 2.7 (4 H, m), 2.9 (6 H, s), 3.4 and 3.5 (4 H, m), 4.1 (1 H, m), 4.5 (1 H, m), 4.8 (2 H, m), 5.1 (2 H, s), 7.3 (5 H, ArH); $\delta_C$ (d$_3$ methanol) 22.3, 22.4, 23.2, 24.5, 25.4, 25.6, 27.1, 35.2, 38.2, 41.1, 44.8, 49.0, 53.0, 64.6, 125.7, 126.1, 126.6, 155.4, 169.5, 171.2, 171.8, 199.0. MS: m/z Calcd for $C_{26}H_{38}BrN_3O_7S$: 616 (M−Br+H 537). Observed 537.

(l) N-α-Benzyloxycarbonyl-γ-propyl-L-glutaminyl-6-dimethylsulfonium-5-oxo-L-norleucine Bromide Salt (See '299' Above)

m.p. 82-85° C. (dec.), $\nu_{max}$ (KBr)/cm$^{-1}$ 3414, 2927, 1720, 1698, 1668, 1636; $\delta_H$ (d$_3$ methanol) 0.9 (3 H, t), 1.5 (2 H, q), 1.9, 2.1 and 2.3 (4 H, m), 2.9 (6 H, s), 3.2 (2 H, t), 4.1 (1 H m), 4.5 (1 H, m), 4.8 (2 H, m), 5.1 (2 H, s), 7.3 (5 H, ArH); $\delta_C$ (d$_3$ methanol) 11.7, 23.5, 25.4, 26.0, 28.9, 33.0, 34.7, 38.1, 42.3, 52.0, 56.0, 67.7, 128.7, 128.8, 129.1, 129.6, 138.2, 158.4, 174.4, 174.6, 174.9, 201.8. MS: m/z Calcd for $C_{24}H_{36}BrN_3O_7S$: 590 (M−Br+H=511). Observed 511.

(m) N-Benzyloxycarbonyl-L-phenylalanyl-6-diethylsulfonium-5-oxo-L-norleucine Bromide Salt (See '300' Above)

m.p. 86-89° C. (dec.), $\nu_{max}$ (Kr)/cm$^{-1}$ 3296, 2932, 1716, 1700, 1661, 1636; $\delta_H$ (d$_3$ methanol) 1.4 (6 H, t), 1.9, 2.3 and 2.7 (4 H, m), 2.9-3.1 (2 H, m), 3.4 (4 H, q), 4.4 (1 H, m), 4.5 (1 H, m), 4.9 (2 H, m), 5.0 (2 H, s), 7.3 (5 H, ArH); $\delta_C$ (d$_3$ methanol) 9.4, 26.5, 34.9, 35.1, 38.2, 38.8, 52.0, 57.9, 67.5, 127.8, 128.5, 129.0, 129.4, 129.5, 130.3, 138.4, 158.3, 174.2, 174.4, 174.9, 201.6. MS: m/z Calcd for $C_{27}H_{35}BrN_2O_6S$: 594 (M<Br 515) observed 515

(n) N-Benzyloxycarbonyl-L-phenylalanyl-6-tetra-methylmercaptoimidazole-5-oxo-L-norleucine bromide salt N-α-Benzyloxycarbonyl-L-phenylalanyl-6-tetra-methylmercaptoimidazole-5-oxo-L-norleucine Bromide Salt (see '301' above) was prepared from N-α-Benzyloxycarbonyl-L-phenylalanyl-6-bromo-5-oxo-L-norleucine and 1,3,4,5-tetramethylimidazoline-2-thione, which was prepared by the method of Kuhn and Kratz (1993) *Synthesis,* 561, using the method of Freund et al. (1994) *Biochemistry,* 33, 10109.

m.p. 116-118° C. (dec.), ν$_{max}$ (KBr)/cm$^{-1}$ 3414, 3237, 1720, 1657, 1638, 1617; δ$_H$ (d$_3$ methanol) 1.7, 2.2 and 2.5 (4 H, m), 2.3 (6 H, s), 2.9-3.1 (2 H, m), 3.9 (6 H, s), 4.3 (2 H, m), 4.8 (2 H, m), 5.0 (2 H, s), 7.2 (5 H, ArH), 7.3 (5 H, ArH); δ$_C$ (d$_3$ methanol) 9.1, 26.9, 34.3, 38.7, 39.3, 46.5, 51.9, 58.0, 67.5, 127.8, 129.1, 129.5, 129.6, 130.3, 130.9, 138.9, 138.3, 138.4, 158.2, 174.2, 174.4, 201.8. MS: m/z Calcd for C$_{30}$H$_{37}$BrN$_4$O$_6$S: 661 (M−Br+H=582). Observed 582.

(o) N-9-Fluorenylmethyloxycarbonyl-L-phenylalanyl-6-dimethylsulfonium-5-oxo-L-norleucine Bromide Salt (See '302' Above)

m.p. 95-98° C. (dec.), ν$_{max}$ (KBr)/cm$^{-1}$ 3415, 3310, 2926, 1720, 1648; δ$_H$ (d$_6$ DMSO) 1.8, 2.1 and 2.7 (4 H, m), 2.8 (6 H, s), 2.9-3.0 (2 H, m), 4.1-4.3 (5 H, m), 4.7 (2 H, m), 7.3 (9 H, ArH), 7.6 (2 H, ArH), 7.8 (2 H, ArH). MS: m/z Calcd for C32H35BrN2O6S: 654 (M−Br575) Observed 575

(p) N-α-tert-butyloxycarbonyl-L-phenylalanyl-6-dimethylsulfonium-5-oxo-L-norleucine Bromide Salt (See '303' Above)

m.p. 105-109° C. (dec.), ν$_{max}$ (KBr)/cm$^{-1}$ 3413, 2930, 1720, 1663; δ$_H$ (d$_6$ DMSO) 1.3 (9 H, s), 1.8, 2.1 and 2.7 (4 H, m), 2.8 (6 H, s), 2.9-3.0 (2 H, m), 4.2 (2 H, m), 4.7 (2 H, m), 7.3 (5 H, ArH). MS: m/z Calcd for C$_{22}$H$_{33}$BrN$_2$O$_6$S: 531 (M−Br 453) observed 453

(q) N-Benzyloxycarbonyl-L-prolinyl-6-tetra-methylmercaptoimidazole-5-oxo-L-norleucine Bromide Salt N-α-Benzyloxycarbonyl-L-prolinyl-6-tetra-methylmercaptoimidazole-5-oxo-L-norleucine Bromide Salt (see '304' above) was prepared from N-α-Benzyloxycarbonyl-L-prolinyl-6-bromo-5-oxo-L-norleucine and 1,3,4,5-tetramethyimidazoline-2-thione, which was prepared by the method of Kuhn and Kratz (1993) *Synthesis,* 561, using the method of Freund et al. (1994) *Biochemistry,* 33, 10109.

m.p. 110° C. (dec.), ν$_{max}$ (KBr)/cm$^-$ 3426, 2927, 1700, 1630, 1638, 1617; δ$_H$ (d$_3$ methanol) 1.7-2.1 (4 H, m), 2.2 (2 H, m), 2.3 (6 H, s), 2.6 (2 H, m), 3.3 (2 H, m), 3.7 (6 H, s), 3.9 (2 H, m), 4.2 (1 H, m), 4.3 (1 H, m), 5.0 (2 H, m), 7.3 (5 H, ArH); δ$_C$ (d$_3$ methanol) 8.7, 23.9, 25.2, 31.1, 33.7, 36.4, 40.4, 44.0, 46.6, 59.5, 65.8, 127.5, 127.8, 128.2, 128.9, 129.0, 136.9, 153.9, 172.1, 173.0, 202.9. MS: m/z Calcd for C$_{26}$H$_{35}$BrN$_4$O$_6$S: 610 (M−Br 531) observed 531

Synthesis of N-Benzyloxcarbonyl-L-phenylalanyl-L-2-amino-5-dimeth-ylsulfonium-4-oxo-norvaline Bromide Salt (Compound '289')

5

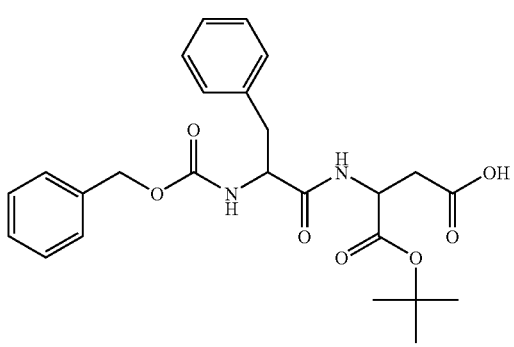

-continued

6

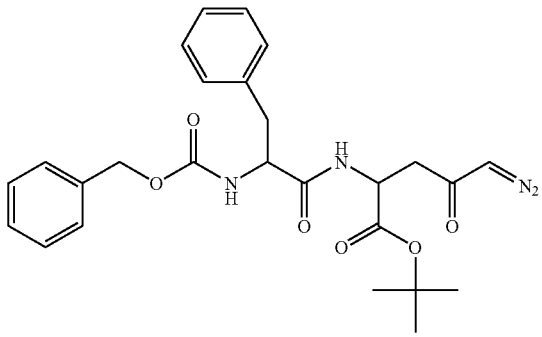

7

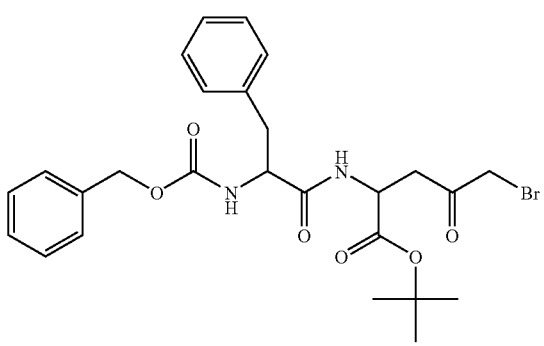

8

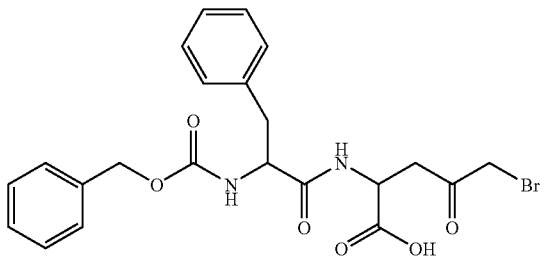

289

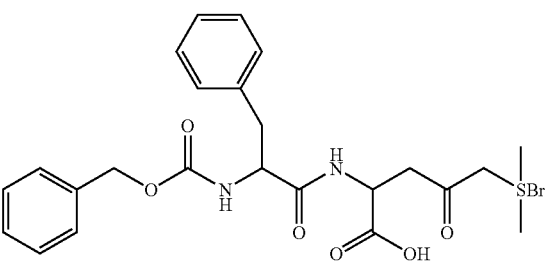

Compound '5' is made by reaction of commercially available N-α-CBZ-L-phenylalanine N-hydroxy-succinimide ester (Novabiochem Cat. No. 04-12-0573) and L-aspartic acid β-t-butyl ester (Novabiochem Cat. No. 04-12-5000) in water/THF (1:1) in the presence of 1.5 equivalents of triethylamine.

(a) N-Benzyloxycarbonyl-L-phenylalanyl-L-2-amino-5-diazo-4-oxo-norvaline Tert-butyl Ester (See '6' Above)

N-Methylmorpholine (0.63 ml, 5.75 mmol) followed by n-butyl chloroformate (0.74 ml, 5.75 mmol) were added to a cold (−78° C.) solution of N-α-benzyloxycarbonyl-L-phenylalanyl-aspaidic acid B-t-butyl ester (see '5' above) (2.35 g, 5 mmol) in THF (100 ml) in an atmosphere of nitrogen. The reaction was stirred for 0.5 h. and an ethereal solution of diazomethane, prepared from N-methyl-N-nitroso-4-toluenesulfonamide (6.23 g, 29 mmol), was added, dropwise, and the reaction left to warm to room temperature overnight. Saturated ammonium chloride solution (100 ml) was added and the mixture stirred vigorously for 5 min., then the layers were separated. Removal of the solvent in vacuo gave a solid residue which was recrystallised from cyclohexane/DCM to yield the product as a pale yellow solid (1.91 g, 77%).

m.p. 122-124° C., (Found: C, 62.88; H, 6.38; N, 11.01. $C_{26}H_{30}N_4O_6$ requires C, 63.15; H. 6.11; N, 11.33%.); $v_{max}$ (KBr)/cm$^{-1}$ 3296, 2105, 1736, 1689, 1655; $\delta_H$ (CDCl$_3$) 1.4 (9 H, s), 2.8 and 3.2 (2 H, m), 3.6 (2 H, s), 4.4 (1 H, m), 4.6 (1 H, m), 5.1 (2 H, s), 5.2 (1 H, d), 6.9 (1 H, d), 7.3 (10H, ArH); $\delta_C$ (CDCl$_3$) 27.8, 36.2, 38.3, 49.6, 55.8, 67.2, 82.8, 127.3, 128.5, 128.6, 129.1, 129.2, 130.2, 136.0, 136.6, 153.5, 169.4, 170.7, 191.5.

(b) N-Benzyloxycarbonyl-L-phenylalanyl-L-2-amino-5-bromo-4-oxo-norvaline Tert-butyl Ester (See '7' Above)

To a cold (0° C.) solution of N-benzyloxycarbonyl-L-phenylalanyl-L-2-amino-5-diazo-4-oxo-norvaline tert-butyl ester (see '6' above) (1 g, 2 mmol) in ethyl acetate (40 ml) was added a 1:1 solution of 48% HBr/acetic acid (2 ml) dropwise. The mixture was stirred for a further 10 min. and the organic was washed with water (10 ml ×3), brine (10 ml) and dried over MgSO$_4$. Removal of the solvent in vacuo gave a solid residue which was recrystallised from cyclohexane to give a white solid (0.915 g, 84%).

m.p. 126-127° C.; $v_{max}$ (KBr)/cm$^{-1}$ 3294, 1738, 1690, 1654; $\delta_H$ (CDCl$_3$) 1.4 (9 H, s), 2.8 and 3.2 (2 H, m), 3.6 (2 H, s), 3.8 (2 H, s), 4.4 (1 H, m), 4.6 (1 H, m), 5.1 (2 H, s), 5.6 (1 H, d), 6.9 (1 H, d), 7.3 (10H, ArH); $\delta_C$ (CDCl$_3$) 27.8, 33.7, 38.2, 41.4, 49.3, 55.9, 82.9, 127.3, 128.5, 128.6, 129.1, 129.2, 130.2, 136.0, 136.6, 153.5, 169.4, 170.7, 199.8.

(c) N-Benzyloxycarbonyl-L-phenylalanyl-L-2-amino-5-bromo-4-oxo-norvaline (See '8' Above)

To a solution of the t-butyl ester (see '7' above) (0.55 g, 1 mmol) in DCM (10 ml) was added trifluoroacetic acid (0.95 ml, 12.5 mmol) and triethylsilane (0.4 ml, 2.5 mmol). The reaction was stirred for 1.5 h. and the volatiles removed under vacuum. The resulting residue was triturated with ether to give the product as a colourless solid (0.38 g 78%).

m.p. 134-136° C., (Found: C, 53.57; H, 4.70; N, 5.65. $C_{22}H_{23}BrN_2O_6$ requires C, 53.78; H, 4.72; N, 5.70%.); vmia (KBr)/cm$^{-1}$ 3295, 1718, 1689, 1654; $\delta_H$ (CDCl$_3$) 2.8 and 3.2 (2 H, m), 3.3 (2 H, m), 3.7 (2 H, s), 4.5 (1 H, m), 4.7 (1 H, m), 5.1 (2 H, s), 5.8 (1 H, d), 5.9 (1 H, d), 6.8 (1 H, br), 7.3 (10H, ArH); $\delta_C$ (CDCl$_3$) 33.7, 38.2, 41.4, 49.3, 55.9, 67.2, 127.0, 127.8, 128.1, 128.4, 129.3, 136.1, 136.6, 156.5, 171.4 176.7, 200.1.

(d) N-Benzyloxycarbonyl-L-phenylalanyl-L-2-amino-5-dimethyl-sulfonium-4-oxonorvaline Bromide Salt (See '289' Above)

The sulfonium salt, N-benzyloxycarbonyl-L-phenylalanyl-L-2-amino-5-dimethyl-sulfonium-4-oxo-norvaline bromide, was prepared as described above from bromomethyl ketone (see '8' above) (0.1 g, 0.2 mmol) and methyl sulfide (0.11 ml, 1.5 mmol). Freeze-drying afforded the product as a colourless hygroscopic solid (20 mg, 18%).

m.p. 98° C. (dec.); $v_{max}$ (KBr)/cm$^{-1}$ 1716, 1689, 1669; $\delta_H$ (d$_4$ methanol) 2.8 and 3.2 (2 H, m), 3.2 (6 H, s), 3.8 (2 H, s), 4.7 (1 H, m), 4.9 (1 H, m), 5.1 (2 H, s), 5.9 (1 H, s), 6.5 (1 H, d), 7.3 (10 H, ArH). $\delta_C$ (d$_4$ methanol) 25.4, 38.8, 43.9, 49.8, 57.8, 67.5, 68.1, 127.8, 128.5, 128.9, 129.5, 130.3, 136.1, 136.6, 158.3, 173.1, 174.1, 200.1. MS: m/z Calc. for $C_{24}H_{29}Br N_2O_6S$ 552 (M–Br=473) Observed: 473

Synthesis of a Higher Homologue of N-Benzyloxycarbonyl-L-phenylalanyl-6-dimethylsulfonium-5-oxo-L-norleucine Bromide Salt (See 'Compound 287' Below)

The acid was prepared from 6-diazo-N-(9-fluorenylmethyloxycarbonyl)-5-oxo-L-norleucine ethyl ester (2.53 g, 6 mmol) by the method of Coutts et al. Yield after flash column chromatography (ethyl acetate 100%) 1.64 g, 66%.

(a) N-(-9-Fluorenylmethyloxycarbonyl)-L-2-amino-7-diazo-6-oxo-heptanoic Acid-1-Ethyl Ester To a cold (0° C.) solution of the acid (0.94 g, 2.3 mmol) in DCM (24 ml) was added oxalyl chloride (1.725 ml of a 2M solution in DCM, 3 3.45 mmol) dropwise. The reaction was warmed to room temperature and stirring continued for a further 40 min. The reaction was again cooled to 0° C. and oxalyl chloride (1.725 ml of a 2M solution in DCM, 3.45 mmol) added dropwise. The reaction was warmed to room temperature and stirring continued for a further 2 h. The volatiles were removed under reduced pressure to give a yellow solid. The solid was dissolved in THF/acetonitrile (1:1 24 ml) and cooled in an ice bath under a blanket of nitrogen. To the solution was added trimethylsilyldiazomethane (4.6 ml of a 2M solution in hexane, 9.2 mmol) dropwise and the reaction stirred at 0° C. for 1½ h. To the mixture was added saturated ammonium chloride solution and the phases separated. The organic was washed with 10% Na$_2$CO$_3$ (5 ml, ×3), brine (5 ml) and dried over Na$_2$SO$_4$. Removal of the solvent in vacuo gave an orange oil which was purified by flash column chromatography (3:2 petrol/ethyl acetate) to afford the product as a pale yellow solid (0.65 g, 65%).

m.p 123-124° C. (CCl$_4$, dec.) $v_{max}$ (KBr)/cm$^{-1}$ 3354, 2103, 1739, 1686, 1635; $\delta_H$ (CDCl$_3$) 1.3 (3 H, t), 1.7, 1.9 and 2.3 (6 H, m), 4.2 (3 H, m), 4.4 (3 H, m), 5.2 (1 H, s), 5.4 (1 H, d), 7.3 (4 H, m, ArH), 7.6 (2 H, ArH), 7.8 (2 H, m, ArH); $\delta_C$ (CDCl$_3$) 14.1, 20.6, 32.0, 40.1, 47.1, 53.5, 54.5, 61.6, 67.0, 120.0, 125.1, 127.0, 127.7, 141.2, 143.8, 155.9, 172.2, 192.4.

(b) L-2-amino-7-diazo-6-oxoheptanoic Acid

The diazoketone (0.5 g, 1.15 mmol) was deprotected with piperidine as previously described to give the amino acid as a pale yellow solid (57.2 mg, 54%).

m.p. 122-124° C. (Lit. m.p. 125-126° C.) $v_{max}$ (KBr)/cm$^{-1}$ 3436, 2108, 1630 (Weygand et al., Chem. Ber. 91, 1037-40).

(c) N-Benzyloxycarbonyl-L-phenylalanyl-7-bromo-6-oxo-heptanoic Acid

The dipeptide was prepared by the method previously described to give a colourless solid (93 mg, 66%).

m.p. 108-110° C. (ethyl acetate), $v_{max}$ (KBr)/cm$^{-1}$ 3296, 1715, 1700, 1661; $\delta_H$ (d$_3$ methanol) 1.6, 1.8 and 2.6 (6 H, m), 2.9-3.1 (2 H, m), 4.1 (2 H, s), 4.4 (2 H, m) 5.0 (2 H, s), 7.3 (10 H, ArH), 7.4 (1 H, d); $\delta_C$ (d$_3$ methanol) 21.0, 31.8, 39.7, 53.2, 57.7, 56.3, 67.5, 127.7, 128.6, 128.9, 129.4, 130.4, 138.1, 138.5, 158.2, 174.2, 174.8, 203.4. MS: m/z Calcd for $C_{24}H_{27}BrN_2O_6$: 518 (M–Br=439). Observed 519, 439.

(d) N-Benzyloxycarbonyl-L-phenylalanyl-7-dimethylsulfonium-6-oxo-heptanoic Acid Bromide Salt (Compound '288')

The sulfonium salt was prepared as previously described, to give a colourless hygroscopic solid (48 mg, 57%).

m.p. 94-96° C. (dec.), $v_{max}$ (KBr)/cm$^{-1}$ 3296, 1715, 1700, 1661; $\delta_H$ (d$_6$ acetone) 1.7, 1.9 and 2.7 (6 H, m), 2.8-3.1 (2 H, m), 2.9 (6 H, s), 4.4 (2 H, m), 4.9 (2 H, d), 5.0 (2 H, s), 7.3 (10 H, ArH); $\delta_C$ (d$_6$ acetone) 20.5, 25.3, 31.7, 39.0, 41.6, 53.1, 53.2, 57.7, 67.5, 127.7, 128.5, 128.9, 129.4, 129.5, 130.4, 138.2, 138.5, 158.2, 174.3, 174.7, 202.3. MS: m/z Calcd for C$_{26}$H$_{33}$BrN$_2$O$_6$S: 580 (M−Br=501). Observed 501.

Example 2

Inhibition of TGase Activity

The efficacy of exemplary compounds of the invention in the inhibition of transglutaminase was verified by studying the dose-dependency of their effects on the activity of purified guinea pig liver transglutaminase (gp1TGase), using an enzyme-linked sorbent assay (ELSA) based on biotinylated cadaverine (BTC) incorporation into N,N'-dimethyl casein (DMC).

Experiments were performed as follows:

Inhibition of guinea pig liver TG (TGase) was tested using an enzyme-linked sorbent assay (ELSA) based on the incorporation of biotin cadaverine (BTC) into N,N'-dimethyl-casein (DMC). Microtitre plates (96-well) were coated with 100 µl of 10 mg/ml DMC in 10 mM Tris pH 7.4 overnight at 4° C. The following day, plates were washed twice with TBS-Tween pH 7.4, once with TBS pH7.4, and a reaction mix was prepared that contained 5 mM CaCl$_2$, 5 mM DTT and 0.132 MM BTC in 50 mM Tris pH 7.4. The mix was prepared so that the appropriate final concentrations would be achieved upon addition of 10 µl of 200 µg/ml TGase to 990 µl of mix to start the reaction. TGase inhibitors were initially prepared as 100 mM stock solutions in H$_2$O and diluted to the appropriate final concentration in the same reaction solution. Negative control samples for TGase activity consisted of mixes that did not contain BTC, and where 10 mM EDTA was substituted for 5 mM CaCl$_2$.

Following addition of TGase, 100 µl of solution was pipetted into 8 replicate wells per sample, and the reaction was allowed to proceed for 1 hour at 37° C. The reaction was terminated by removal of the solution and the addition of 100 µl of 10 mM EDTA in PBS pH7.4. Plates were again washed twice with TBS-Tween pH 7.4, once with TBS pH 7.4, and blocked by incubation with 100 µl per well of 3% (w/v) bovine serum albumin (BSA) in PBS pH7.4 for 1 hour at room temperature. Incorporated BTC was detected by incubation with 100 µl per well of Extravidin peroxidase (XAP) solution, diluted 1 in 5000 in blocking buffer for 1 hour at 37° C. Plates were washed as before and prior to development, plates were preincubated for 5 minutes in 0.05M phosphate-citrate buffer pH5.0 containing 0.014% (v/v) H$_2$O$_2$. The solution was removed and replaced with 100 µl per well of the same buffer containing 75 µg/ml tetramethylbenzidine (TMB). The developing reaction was allowed to proceed at room temperature for 5-15 minutes and was terminated by the addition of 50 µl of 1N H$_2$SO$_4$. The absorbance of the resulting colour was measured on a microtitre plate reader at 450 nm.

The data shown indicate a representative experiment using eight replicate samples. The mean absorbance 450 nm±SD is shown.

The effect of exemplary compounds of the invention (and control compounds) on tissue transglutaminase activity in vitro are shown in FIGS. 2 to 21.

Example 3

Inhibition of TGase-Mediated Protein Cross-Linking

Assay method
1. Preactivate TGase in 3 mM DTT (where applicable) on ice for 1 hr.
2. Crosslink TGase with fibronectin in 40 mM Tris/100 mM NaCl at 50 µg/ml final concentration each, according to Table 1 below. Include non-activated Tgase/preactivated Tgase controls in the presence and absence of the inhibitors to investigate potential homodimer formation.
3. Incubate at 37° C. for 2 hr to allow crosslink formation to take place.
4. Solubilise crosslink in 2× Laemmli buffer. Vortex and spin down insoluble material.
5. Load 20 µg of total protein (Tgase+Fn) on a 7% acrylamide SDS PAGE gel. Run gel at 100 mV until dye escapes from the bottom of the gel.
6. Stain with coomassie brilliant blue for 1 hr at RT.
7. De-stain in 30% methanol/10% acetic acid at RT.

TABLE 1

| Component | Control 1 Non-activated TGase | Control 2 Pre-activated TGase | Control 3 Pre-activated TGase + Compound 285 | Control 4 Fibronectin | Control 5 TGase + Fibronectin | TGase + Fibronectin + Compound 281 | TGase + Fibronectin + Compound 283 | TGase + Fibronectin + Compound 285 |
|---|---|---|---|---|---|---|---|---|
| Tris pH 7.4 (mM) | 40 | 40 | 40 | 40 | 40 | 40 | 40 | 40 |
| NaCl (mM) | 100 | 100 | 100 | 100 | 100 | 100 | 100 | 100 |
| TGase (µg/ml) | 50 | 50 | 50 | 50 | 50 | 50 | 50 | 50 |
| Fibronectin (µg/ml) | | 50 | | 50 | 50 | 50 | 50 | 50 |
| Compound 281 (µM) | | | | | | 250 | | |
| Compound 283 (µM) | | | | | | | 250 | |
| Compound 285 (µM) | | | 250 | | | | | 250 |

Compound 281 = N-Benzyloxycarbonyl-L-phenylalanyl-6-dimethyl-sulfonium-5-oxo-L-norleucine bromide salt
Compound 283 = 1,3-dimethyl-2-(2-oxopropylsulfanyl)-3H-1,3-diazol-1-ium-chloride (as disclosed in U.S. Pat. No. 4,968,713)
Compound 285 = N-Benzyloxycarbonyl-L-glutaminyl-6-dimethylsulfonium-5-oxo-L-norleucine bromide salt SDS-PAGE data showing tTGase-mediated crosslinking of fibronectin following treatment with exemplary compounds of the invention is shown in FIG. 22.

Example 4

Inhibition of Kidney Fibrosis in Rats

Method for Inhibitor Delivery Using Osmotic Minipumps

Male Wistar rat of approximately 300 g weight was anaesthetised using 5% halothane and maintained at 3% for the duration of the surgical procedure. The rat was subjected to a ⅝th subtotal nephrectomy (SNx) by ligation of the left renal artery and vein followed by complete nephrectomy of the left kidney. The right kidney had both the upper and lower poles ligated followed by excision of both poles. A 9-cm cannula (0.32 mm bore) was sealed on one end and fenestrated between 3 and 12 mm from the sealed end. This was then inserted through the parenchyma (cut to cut/pole to pole) of the kidney so that the blunt end was just visible through one of the cut ends. This was then sealed in position using tissue glue on both ends of the kidney such that the fenestrated area was within the remnant kidney. The cannula was passed through the muscle wall, which was then stitched using reabsorbable sutures. The cannula was then attached to the regulator of a 2 ml osmotic minipump (Azlet osmotic minipump (2 ml4), Charles Rivers, UK) that was loaded (primed for 15 hrs at RT) with either PBS (SNx) or TGase inhibitor 281 or 283 (SNx+281 and SNx+283, respectively) at a concentration of 50 mM (delivery 1.5 µl per hour). The pump was then positioned subcutaneously on the right upper flank of the animal and the skin sutured. The animal was then switched onto oxygen and allowed to partially regain consciousness before being returned to the cage. The pump was changed every 28 days under halothane anaesthesia. After 83 days, the animal was placed in a metabolic cage to collect a 24-hour urine sample. The animal was then anaesthetised, the remnant kidney recovered and a terminal blood sample collected.

Tissue samples were sectioned and then underwent Masson's Trichrome staining (Johnson et al., 1997, 99:2950-2960) or collagen III staining.

For collagen III staining, paraffin embedded sections (4 µm) were first dewaxed and hydrated by standard protocol (xylene 10 min, 100% ethanol 5 min, 90% ethanol 5 min, 75% ethanol 5 min, 50% ethanol 5 min, water 10 min) washed in PBS for 10 min and any endogenous peroxides quenched by treatment with 3% H2O2 in methanol for 10 min. After washing in PBS for 10 min sections were treated with the epitope revealing agent TUF (ID Labs Inc. Cat no BP1122) on a water bath at 92 C for 10 min then allowed to cool to room temperature. Sections were washed with PBS for 10 min and then trypsin (Zymed Labs Cat No 00-3008) digested (trypsin diluted 1:3) for 10 min at 37 C followed by two washes in PBS for 5 min each. Sections were then blocked in goat serum (Vector Labs Cat No S1000) incubated at 37 C for 30 min. The primary collagen III antibody (Goat anti-human type m collagen, Southern Biotech Assocs diluted 1 in 10 in 0.1% bovine serum albumin [BSA] in PBS) is then added and incubated overnight at 4 C in a humidity chamber. The samples are then washed twice with 0.1% Nonidet in PBS for 5 min followed by two washes in PBS for 5 min. The secondary antibody (rabbit anti goat which is biotinylated from DAKO Cat No E0466) diluted 1 in 400 in 0.1% BSA/PBS is then added and incubated for 30 min at 37 C. The sections are then washed twice in 0.1% Nonidet in PBS and the sections then incubated with the Avidin Biotin Enzyme complex (ABC) kit (Vector Labs Cat No PK-6102) according to the manufacturers instructions for 30 min at T 37° C. The samples are then washed twice in PBS and the reagent substrate, 3-amino-9-ethyl carbozole (AEC [Vector Labs Cat No SK4200]) added to allow colour development (approx 5-30 min). After washing twice with water for 5 min and then twice with PBS for 5 min the samples are counterstained with haematoxylin (diluted 1 in 10 from Thermo Shandon, Gill-2 haematoxylin Cat No 6765007) for 5 min, washed twice with water for 5 min, washed with PBS once and then sections mounted using glycergel prior to viewing under a light microscope.

FIG. 23 shows (a) representative Masson's Trichrome stained sections and (b) collagen III stained sections from kidneys of animals in which inhibitor compound 281 (designated 'SNx+281') and compound 283 (designated 'SNx+283') were instilled (see Johnson et al., 1999, J. Am. Soc. Nephrol. 10:2146-2157 for method used to induce subtotal nephrectomy).

FIG. 24 shows quantative image analysis of (a) Masson's Trichrome stain and (b) collagen III stain in kidney sections from 90 day animals following treatment with inhibitor compounds 281 (designated 'SNx+281') and 283 (designated 'SNx+283'). Snc and SNx are referred to as above. For Masson's Trichrome staining, analysis was performed by systematically acquiring adjacent overlapping cortical fields at 100× magnification such that 5 fields encompassed more than 80% of the cortex. Each field was then subject to 3 phase analysis using image analysis and the area of blue (collagen), red (cytoplasm) and white (lumen) determined ensuring greater than 95% coverage. The scarring index was determined by expressing the blue phase as a fraction of the cytoplasmic. Five animals per group were used and data expressed a mean values+/−5 S.E.M. The composite diagram showing staining in FIG. 12(a) shows 1 field from each animal. For Collagen III staining the relative amounts of collagen III present (stained brown) were determined by systematically acquiring data from 10 overlapping cortical fields at 200× magnification and expressed as Mean values±SEM.

In situ TGase Activity in Kidney Cryostat Sections

Rat kidneys treated in vivo with TGase inhibitors were snap-frozen in liquid nitrogen and 14 µm sections were cut using a cryostat and allowed to air-dry. Sections were rehydrated for 10 minutes at room temperature in a solution of 5% (w/v) rabbit serum, 10 mM EDTA, 0.01% (v/v) Triton X-100 in 50 mM Tris pH7.4, containing EXAP (diluted 1 in 200) to block endogenous biotin. Following rehydration, slides were washed twice in PBS pH7.4, and sections were incubated for 1 hour at 37° C. with a reaction mix containing 5 mM CaCl2, 5 mM DTT and 0.5 mM BTC in 50 mM Tris pH 7.4. Negative controls consisted of mixes that did not contain BTC, and where 10 mM EDTA was substituted for 5 mM CaCl2. A positive control was also included that contained 20 µg/ml TGase. Following incubation, slides were washed once in PBS pH 7.4 containing 10 mM EDTA, fixed in ice-cold acetone for 5 minutes and allowed to air-dry. Dried sections were blocked in 3% (w/v) BSA in PBS pH7.4 overnight at 4° C., and incorporated BTC was revealed by incubation with Streptavidin-CyS, diluted 1 in 100 in the same buffer for 2 hours at 37° C. Slides were viewed on a Leica TCSNT confocal microscope equipped with excitation and emission filters for Cy5, and emitted fluorescence was quantified with the software supplied by the manufacturer. FIG. 25a shows semi-quantitative analysis of the emission from Leica confocal laser microscope from TRITC-extravidin bound to TGase incorporated biotin cadaverine in cryostat sections taken from kidneys of SNx rats treated for 28 days with the inhibitors 281 and 283. SNc refers to control kidneys obtained from animals undergoing a sham operation with subtotal nephrectomy. SNx refers to subtotal nephrectomy. Inhibitors were delivered to the kidney by mini pumps as outlined above. Data are mean values+/−SEM taken from 5 separate kidneys.

Analysis of 14C Putrescine Incorporation

A second method of assaying TGase activity, 14C putrescine incorporation into N,N'-dimethylcasein using tissue homogenates of kidneys from SNx rats treated with the inhibitors for 84 days, confirmed the effect of treatment with compounds 281 and 283 on Tgase activity (see FIG. 25b).

Putrescine incorporation experiments were performed as described in Skill et al., 2001, *Lab. Invest* 81:705-716 and Lorand et al., 1972, *Anal Biochem* 50:623-631

Analysis of Proteinurea, Creatinine Clearance, Serum Creatinine, Urine Creatinine and Urine Urea Table 3 shows levels of proteinurea, creatinine clearance, serum creatinine, urine creatinine and urine urea in 90 day SNx rats in which inhibitor compounds 283 and 281 were instilled into the kidneys.

TABLE 3

| Experiment Group | Proteinuria (mg/24 h) | | Creatinine clearance (ml/min) | | Serum creatinine (mM/L) | |
|---|---|---|---|---|---|---|
| | Mean | SE | Mean | SE | Mean | SE |
| Control (SNc) | 129 | 14 | 1.72 | 0.18 | 46 | 0.6 |
| SNx | 672 | 140 | 0.44 | 0.2 | 224 | 36 |
| SNx + 283 | 835 | 93 | 0.86 | 0.05 | 114 | 16 |
| SNx + 281 | 503 | 63 | 0.94 | 0.09 | 208 | 106 |

| | Urine creatinine (mM/L) | | Serum urea (mM/L) | | Urine urea (mM/L) | |
|---|---|---|---|---|---|---|
| | Mean | SE | Mean | SE | Mean | SE |
| Control (SNc) | 12399 | 2538 | 6.22 | 1.1 | 1160 | 226 |
| SNx | 2551 | 695 | 31.4 | 4.6 | 244 | 29 |
| SNx + 283 | 3138 | 185 | 16.3 | 2.2 | 272 | 20 |
| SNx + 281 | 3999 | 560 | 22.32 | 4.5 | 372 | 50 |

Proteinuria, creatinine clearance, serum clearance, urine creatinine and urine urea were carried out by standard clinical chemistry techniques (Johnson et al., 1997, *J. Clin. Invest.* 99:2950-2960). Creatinine and urea were measured by the standard autoanalyser technique and proteinura by the Biuret method (Johnson et al., supra). Data represent mean values ±SE, taken from 5 animals per group.

Proteinuria and creatinine clearance data are shown in histogram form in FIGS. 26(a) and (b), respectively.

Example 5

Exemplary Pharmaceutical Formulations

The following examples illustrate pharmaceutical formulations according to the invention in which the active ingredient is a compound of the invention.

Example A

Tablet

| Active ingredient | 100 mg |
|---|---|
| Lactose | 200 mg |
| Starch | 50 mg |
| Polyvinylpyrrolidone | 5 mg |
| Magnesium stearate | 4 mg |
| | 359 mg |

Tablets are prepared from the foregoing ingredients by wet granulation followed by compression.

Example B

Ophthalmic Solution

| Active ingredient | 0.5 g |
|---|---|
| Sodium chloride, analytical grade | 0.9 g |
| Thiomersal | 0.001 g |
| Purified water to | 100 ml |
| pH adjusted to | 7.5 |

Example C

Tablet Formulations

The following formulations A and B are prepared by wet granulation of the ingredients with a solution of povidone, followed by addition of magnesium stearate and compression.

Formulation A

| | mg/tablet | mg/tablet |
|---|---|---|
| Active ingredient | 250 | 250 |
| Lactose B.P. | 210 | 26 |
| Povidone B.P. | 15 | 9 |
| Sodium Starch Glycolate | 20 | 12 |
| Magnesium Stearate | 5 | 3 |
| | 500 | 300 |

Formulation B

| | mg/tablet | mg/tablet |
|---|---|---|
| Active ingredient | 250 | 250 |
| Lactose | 150 | — |
| Avicel PH 101 ® | 60 | 26 |
| Povidone B.P. | 15 | 9 |
| Sodium Starch Glycolate | 20 | 12 |
| Magnesium Stearate | 5 | 3 |
| | 500 | 300 |

Formulation C

| | mg/tablet |
|---|---|
| Active ingredient | 100 |
| Lactose | 200 |
| Starch | 50 |
| Povidone | 5 |
| Magnesium stearate | 4 |
| | 359 |

The following formulations, D and E, are prepared by direct compression of the admixed ingredients. The lactose used in formulation E is of the direction compression type.

Formulation D

|  | mg/capsule |
| --- | --- |
| Active Ingredient | 250 |
| Pre-gelatinised Starch NF15 | 150 |
|  | 400 |

Formulation E

|  | mg/capsule |
| --- | --- |
| Active Ingredient | 250 |
| Lactose | 150 |
| Avicel ® | 100 |

Formulation F (Controlled Release Formulation)

The formulation is prepared by wet granulation of the ingredients (below) with a solution of povidone followed by the addition of magnesium stearate and compression.

|  | mg/tablet |
| --- | --- |
| Active Ingredient | 500 |
| Hydroxypropylmethylcellulose (Methocel K4M Premium) ® | 112 |
| Lactose B.P. | 53 |
| Povidone B.P.C. | 28 |
| Magnesium Stearate | 7 |
|  | 700 |

Drug release takes place over a period of about 6-8 hours and was complete after 12 hours.

Example D

Capsule Formulations

Formulation A

A capsule formulation is prepared by admixing the ingredients of Formulation D in Example C above and filling into a two-part hard gelatin capsule. Formulation B (infra) is prepared in a similar manner.

Formulation B

|  | mg/capsule |
| --- | --- |
| (a) Active ingredient | 250 |
| (b) Lactose B.P. | 143 |
| (c) Sodium Starch Glycolate | 25 |
| (d) Magnesium Stearate | 2 |
|  | 420 |

Formulation C

|  | mg/capsule |
| --- | --- |
| (a) Active ingredient | 250 |
| (b) Macrogol 4000 BP | 350 |
|  | 600 |

Capsules are prepared by melting the Macrogel 4000 BP, dispersing the active ingredient in the melt and filling the melt into a two-part hard gelatin capsule.

Formulation D

|  | mg/capsule |
| --- | --- |
| Active ingredient | 250 |
| Lecithin | 100 |
| Arachis Oil | 100 |
|  | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

|  | mg/capsule |
| --- | --- |
| (a) Active ingredient | 250 |
| (b) Microcrystalline Cellulose | 125 |
| (c) Lactose BP | 125 |
| (d) Ethyl Cellulose | 13 |
|  | 513 |

Example E

Injectable Formulation

|  |  |
| --- | --- |
| Active ingredient | 0.200 g |
| Sterile, pyrogen free phosphate buffer (pH7.0) | to 10 ml |

The active ingredient is dissolved in most of the phosphate buffer (35-40° C.), then made up to volume and filtered through a sterile micropore filter into a sterile 10 ml amber glass vial (type 1) and sealed with sterile closures and overseals.

Example F

Intramuscular Injection

| | |
|---|---|
| Active ingredient | 0.20 g |
| Benzyl Alcohol | 0.10 g |
| Glucofurol 75 ® | 1.45 g |
| Water for Injection | q.s. to 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

Example G

Syrup Suspension

| | |
|---|---|
| Active ingredient | 0.2500 g |
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

Example H

Suppository

| | mg/suppository |
|---|---|
| Active ingredient (63 μm) | 250 |
| Hard Fat, BP (Witepsol H15-Dynamit Nobel) | 1770 |
| | 2020 |

One fifth of the Witepsol H15 is melted in a steam-jacketed pan at 45□ C maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

Example 1

Pessaries

| | mg/pessary |
|---|---|
| Active ingredient | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

The invention claimed is:

1. A compound having the following formula I:

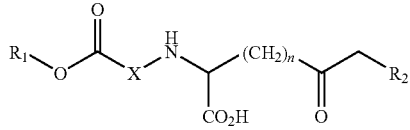

wherein:
'X' represents an α-amino acid group wherein the α-amino group of the amino acid is bound to the $R_1$—O—CO— group and the carboxy group of the amino acid is bound to the $R_2$—$CH_2$—CO—$(CH_2)_n$—$CH(CO_2H)$—NH— group;
'n' is an integer between 1 and 4;
'$R_1$' represents benzyl, t-butyl or 9-fluorenylmethyl; and
'$R_2$' represents

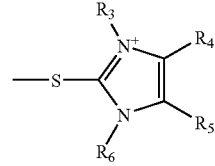

wherein $R_3$, $R_4$, $R_5$ and $R_6$ each independently represent lower alkyl
or —$S^+R_7R_8$, wherein $R_7$ and $R_8$ each independently represent lower alkyl or a pharmaceutically and/or veterinarily acceptable salt or solvate thereof.

2. A compound according to claim 1 wherein X is an L-amino acid group.

3. A compound according to claim 1 wherein X is selected from the group consisting of phenylalanine, glutamine, isoleucine, alanine, glycine, tyrosine, proline, serine, lysine and glutamic acid.

4. A compound according to claim 1 wherein 'n' is 2.

5. A compound according to claim 1 wherein $R_1$ is benzyl.

6. A compound according to claim 1 wherein $R_2$ represents

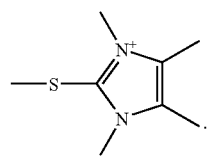

7. A compound according to claim 1 wherein $R_2$ represents $-S^+R_7R_8$, wherein $R_7$ and $R_8$ each independently represent lower alkyl.

8. A compound according to claim 1 wherein $R_3$, $R_4$, $R_5$, $R_6$, $R_7$ and/or $R_8$ are $C_1$ to $C_3$ alkyl.

9. A compound according to claim 1 having the following formula:

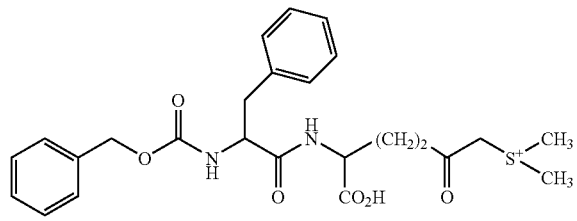

or a pharmaceutically and/or veterinarily acceptable salt or solvate thereof.

10. A compound according to claim 1 having the following formula:

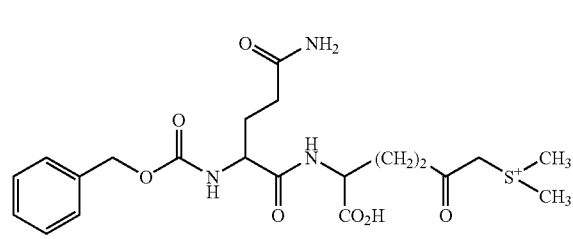

or a pharmaceutically and/or veterinarily acceptable salt or solvate thereof.

11. A compound according to claim 1 having the following formula:

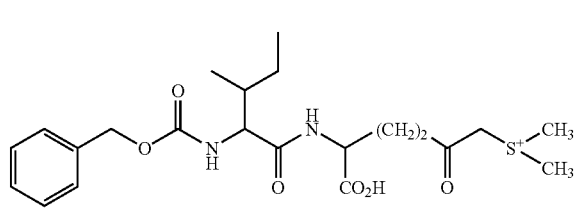

or a pharmaceutically and/or veterinarily acceptable salt or solvate thereof.

12. A compound according to claim 1 having the following formula:

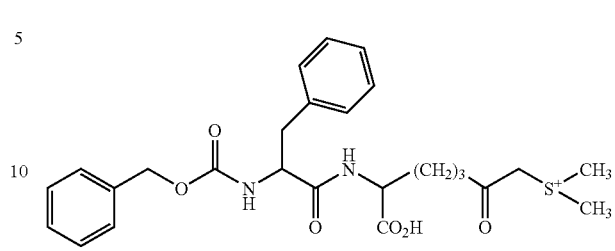

or a pharmaceutically and/or veterinarily acceptable salt or solvate thereof.

13. A compound according to claim 1 having the following formula:

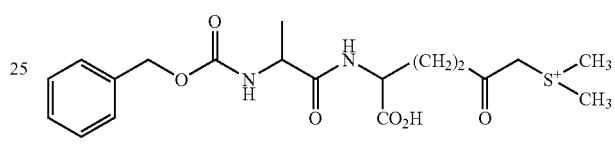

or a pharmaceutically and/or veterinarily acceptable salt or solvate thereof.

14. A compound according to claim 1 having the following formula:

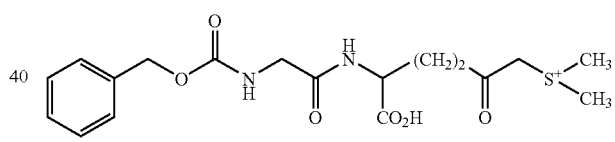

or a pharmaceutically and/or veterinarily acceptable salt or solvate thereof.

15. A compound according to claim 1 having the following formula:

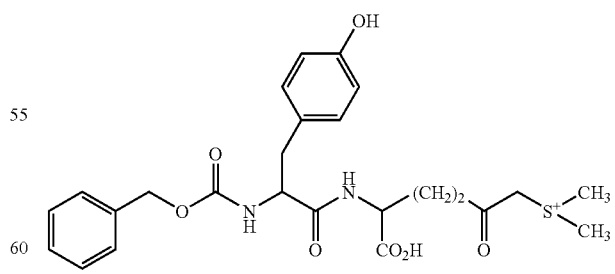

or a pharmaceutically and/or veterinarily acceptable salt or solvate thereof.

16. A compound according to claim 1 having the following formula:

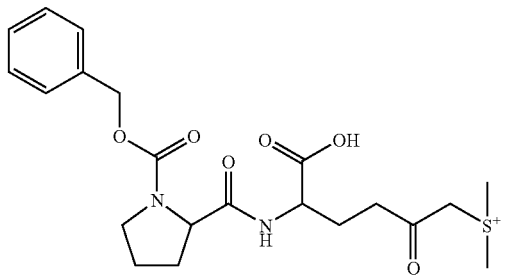

or a pharmaceutically and/or veterinarily acceptable salt or solvate thereof.

17. A compound according to claim 1 having the following formula:

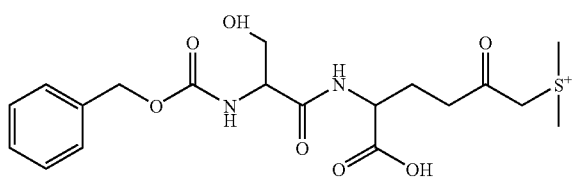

or a pharmaceutically and/or veterinarily acceptable salt or solvate thereof.

18. A compound according to claim 1 having the following formula:

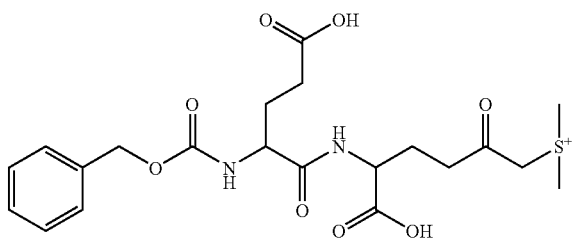

or a pharmaceutically and/or veterinarily acceptable salt or solvate thereof.

19. A compound according to claim 1, wherein the compound is N-α-Benzyloxycarbonyl-N-ε-trifluoroacetate-L-lysinyl-6-dimethylsulfonium-5-oxo-L-norleucine or a pharmaceutically and/or veterinarily acceptable salt or solvate thereof.

20. A compound according to claim 1 having the following formula:

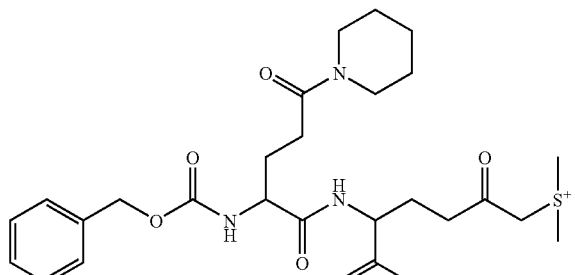

or a pharmaceutically and/or veterinarily acceptable salt or solvate thereof.

21. A compound according to claim 1 having the following formula:

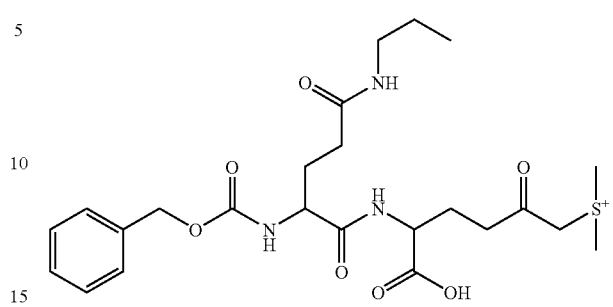

or a pharmaceutically and/or veterinarily acceptable salt or solvate thereof.

22. A compound according to claim 1 having the following formula:

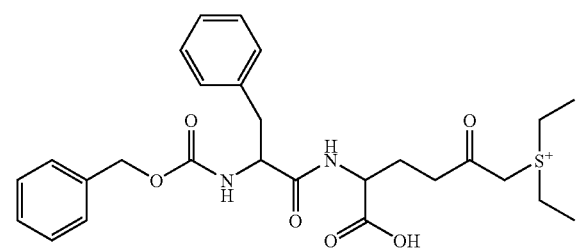

or a pharmaceutically and/or veterinarily acceptable salt or solvate thereof.

23. A compound according to claim 1 having the following formula:

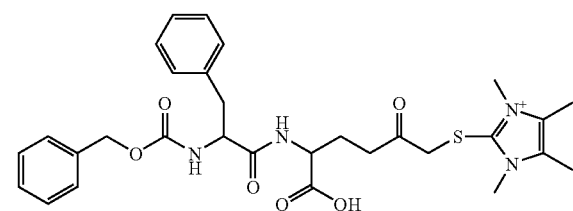

or a pharmaceutically and/or veterinarily acceptable salt or solvate thereof.

24. A compound according to claim 1 having the following formula:

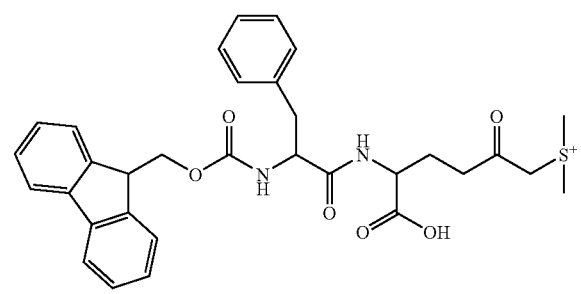

or a pharmaceutically and/or veterinarily acceptable salt or solvate thereof.

25. A compound according to claim 1 having the following formula:

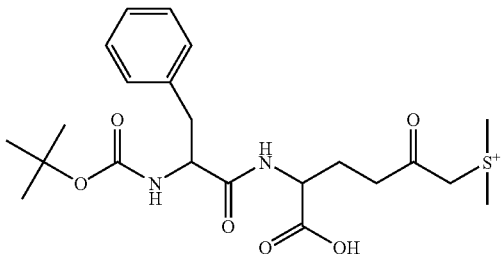

or a pharmaceutically and/or veterinarily acceptable salt or solvate thereof.

26. A compound according to claim 1 having the following formula:

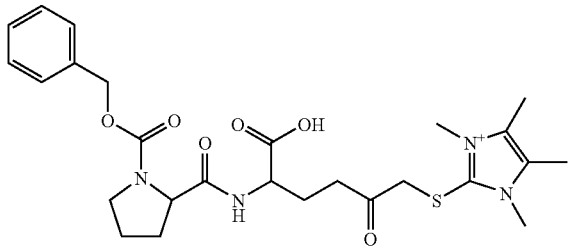

or a pharmaceutically and/or veterinarily acceptable salt or solvate thereof.

27. A compound according to claim 1 in the form of a bromide salt.

28. A pharmaceutical formulation comprising a compound according to claim 1 and a pharmaceutically acceptable carrier.

29. A method for making a compound according to claim 1 comprising the following steps:
 (a) reacting an N-α-protected amino acid N-hydroxy-succinimide or para-nitrophenyl ester with 6-diazo-5-oxo-L-norleucine, and treating the resulting coupled product with hydrogen bromide; and
 (b) reacting the bromomethyl ketone produced in step (a) with dimethyl sulphide, diethyl sulphide or 1,3,4,5-tetra-methyl mercapto-imidazoline-2-thione.

30. A method according to claim 29 wherein the N-α-protected amino acid N-hydroxysuccinimide ester is CBZ, FMOC or BOC protected.

31. A method according to claim 29 wherein step (a) comprises reacting an N-α-protected amino acid N-hydroxy-succinimide or para-nitrophenyl ester with 6-diazo-5-oxo-L-norleucine in the presence of tetrahydrofuran (THF), water and triethylamine followed by reacting the products thereof with hydrogen bromide in the presence of ethyl acetate.

32. A method according to claim 29 wherein the N-α-CBZ-protected amino acid N-hydroxy-succinimide ester is selected from the group consisting of N-α-CBZ-L-phenylalanine N-hydroxy-succinimide ester, N-α-CBZ-L-glutamine N-hydroxy-succinimide ester, N-α-CBZ-L-isoleucine N-hydroxy-succinimide ester, N-α-CBZ-L-alanine N-hydroxy-succinimide ester, N-α-CBZ-L-glycine N-hydroxysuccinimide ester, N-α-CBZ-L-proline N-hydroxy-succinimide ester, N-α-CBZ-L-serine N-hydroxysuccinimide ester, N-α-CBZ-L-tyrosine N-hydroxysuccinimide ester, N-α-CBZ-L-glutamic acid N-hydroxysuccinimide ester, and N-α-CBZ-L-lysine N-hydroxysuccinimide ester.

33. A method for treating a patient suffering from a disease/disorder selected from the group consisting of fibrosis, scarring, neurodegenerative diseases, autoimmune diseases, thrombosis, proliferative disorders, AIDS, psoriasis, cancer, and inflammation, the method comprising administering to the patient a composition comprising the compound of claim 1.

34. The method according to claim 33 wherein the disease/disorder is cancer.

35. A method for treating a patient to prevent or treat rejection of a transplanted organ, the method comprising administering to the patient a composition comprising a compound of claim 1.

36. The method of claim 35 wherein the organ is a heart, lung, kidney or liver.

37. The method of claim 35 wherein the organ is treated prior to transplantation.

38. The method of claim 35 wherein the organ is treated during and/or after transplantation into a patient.

39. The method of claim 33, wherein the disease is a chronic inflammatory disease.

* * * * *